(12) United States Patent
Hussey et al.

(10) Patent No.: US 12,091,698 B2
(45) Date of Patent: Sep. 17, 2024

(54) COMPOSITIONS AND METHODS FOR RNA SYNTHESIS

(71) Applicant: LineaRx, Inc., Stony Brook, NY (US)

(72) Inventors: Brendan Hussey, Toronto (CA); Lai Him Chung, Toronto (CA)

(73) Assignee: LineaRx, Inc., Stony Brook, NY (US)

( * ) Notice: Subject to any disclaimer, the term of this patent is extended or adjusted under 35 U.S.C. 154(b) by 0 days.

(21) Appl. No.: 18/302,247

(22) Filed: Apr. 18, 2023

(65) Prior Publication Data
US 2023/0279458 A1    Sep. 7, 2023

Related U.S. Application Data

(63) Continuation of application No. PCT/IB2021/000727, filed on Oct. 22, 2021.

(60) Provisional application No. 63/104,735, filed on Oct. 23, 2020.

(51) Int. Cl.
*C12P 19/34* (2006.01)
*C12N 9/12* (2006.01)
*C12N 15/11* (2006.01)

(52) U.S. Cl.
CPC .......... *C12P 19/34* (2013.01); *C12N 9/1247* (2013.01); *C12N 15/11* (2013.01); *C12N 2310/20* (2017.05)

(58) Field of Classification Search
CPC ....... C12P 19/34; C12N 9/1247; C12N 15/11; C12N 2310/20; C12N 11/06; C12N 11/14; C12N 15/1093; C12N 2330/30; C12N 15/113; C12N 15/10; C12N 2310/14; C12N 2310/141; C12Y 207/07006; C40B 40/06
See application file for complete search history.

(56) References Cited

U.S. PATENT DOCUMENTS

| | | | |
|---|---|---|---|
| 5,700,667 A | 12/1997 | Marble et al. | |
| 9,512,456 B2 | 12/2016 | Wang et al. | |
| 11,578,348 B2 | 2/2023 | Martin et al. | |
| 2004/0091854 A1* | 5/2004 | Guillerez | C12N 9/1247 435/5 |
| 2012/0052069 A1* | 3/2012 | Belouski | A61P 3/00 514/6.9 |
| 2013/0040365 A1* | 2/2013 | Vander Horn | C12N 9/1252 435/194 |
| 2020/0340028 A1 | 10/2020 | Martin et al. | |

FOREIGN PATENT DOCUMENTS

| | | |
|---|---|---|
| EP | 2377928 A2 | 10/2011 |
| EP | 3521456 A1 | 8/2019 |
| WO | WO-2004039953 A2 | 5/2004 |
| WO | WO-2007075987 A2 | 7/2007 |
| WO | WO-2012104399 A2 | 8/2012 |
| WO | WO-2017049129 A2 | 3/2017 |
| WO | WO-2017212400 A2 | 12/2017 |
| WO | WO-2020002598 A1 | 1/2020 |

OTHER PUBLICATIONS

Hussey, Brendan J., and David R. McMillen. "Programmable T7-based synthetic transcription factors." Nucleic Acids Research 46.18 (2018): 9842-9854 (Year: 2018).*
Davanloo, Parichehre, et al. "Cloning and expression of the gene for bacteriophage T7 RNA polymerase." Proceedings of the National Academy of Sciences 81.7 (1984): 2035-2039 (Year: 1984).*
Tovkach, Andriy, Vardit Zeevi, and Tzvi Tzfira. "Expression, purification and characterization of cloning-grade zinc finger nuclease." Journal of biotechnology 151.1 (2011): 1-8 (Year: 2011).*
Jain, Akshay, and Kun Cheng. "The principles and applications of avidin-based nanoparticles in drug delivery and diagnosis." Journal of controlled release 245 (2017): 27-40 (Year: 2017).*
Bandwar, R.P. et al., "The Energetics of Consensus Promoter Opening by T7 RNA Polymerase," J. Mol. Biol., 2002, vol. 324, 63-72.
Chelliserrykattil J. et al., "A combined in vitro/in vivo selection for polymerases with novel promoter specificities," BMC Biotechnol., 2001, vol. 1, No. 13, pp. 1-7.
Cook, P.R. et al., "Transcription by an immobilized RNA polymerase from bacteriophage T7 and the topology of transcription," Nucleic Acid Research, 1992, vol. 20, No. 14, pp. 3591-3598.
Dang, Y. et al., "Optimizing sgRNA structure to improve CRISPR-Cas9 knockout efficiency" Genome Biology, 2015, vol. 16, No. 280, pp. 1-10.
Deltcheva, E. et al., "CRISPR RNA maturation by trans-encoded small RNA and host factor RNase III." Nature, 2011, vol. 471, No. 7340, pp. 602-607.
Dickinson, B.C. et al., "Experimental Interrogation of the Path Dependence and Stochasticity of Protein Evolution Using Phage-Assisted Continuous Evolution." PNAS, 2013, vol. 110, No. 22, pp. 9007-9012.
Ducker, R.E. et al., "A comparative investigation of methods for protein immobilization on self-assembled monolayers using glutaraldehyde, carbodiimide, and anhydride reagents," Biointerphases, 2008, vol. 3, No. 3, pp. 59-65.
Esvelt, K. et al., "A System for the Continuous Directed Evolution of Biomolecules," Nature, 2011, vol. 472, No. 7344, pp. 499-503.
Ferretti, J.J. et al., "Complete genome sequence of an M1 strain of *Streptococcus pyogenes*," PNAS, 2001, vol. 98, pp. 4658-4663.
Friedland, A.E. et al., "Characterization of *Staphylococcus aureus* Cas9: a smaller Cas9 for all-in-one adeno-associated virus delivery and paired nickase applications" Genome Biology, 2015, vol. 16, No. 257, pp. 1-11.

(Continued)

*Primary Examiner* — Nancy J Leith
*Assistant Examiner* — Kyle T Rega
(74) *Attorney, Agent, or Firm* — Wilson Sonsini Goodrich & Rosati

(57) ABSTRACT

Provided herein are compositions, methods, devices, and systems for highly accurate and pure RNA synthesis. Also provided herein are nucleic acid libraries comprising RNAs generated by using devices, compositions and methods disclosed herein.

15 Claims, 12 Drawing Sheets

Specification includes a Sequence Listing.

(56) References Cited

OTHER PUBLICATIONS

Germini, D. et al., "A Comparison of Techniques to Evaluate the Effectiveness of Genome Editing" Trends in Biotechnology, 2018, vol. 36, No. 2, pp. 147-159.

Guillerez, J. et al., "A mutation in T7 RNA polymerase that facilitates promoter clearance," PNAS Apr. 26, 2005, vol. 102, No. 17, pp. 5958-5963.

Han, C.M. et al., "Simultaneous RNA purification and size selection using on-chip isotachophoresis with an ionic spacer," Lab Chip., 2019, vol. 19, pp. 2741-2749.

Hussey, B.J. et al., "Programmable T7-based synthetic transcription factors," Nucleic Acids Research, 2018, vol. 46, No. 18, pp. 9842-9854.

Hussey, B.J., "Towards Engineering a Programmable Universal Transcription Activation Systems," Department of Cell and Systems Biology University of Toronto, 2017, pp. 1-184.

Jinek, M. et al., "Programmable dual-RNA-guided DNA endonuclease in adaptive bacterial immunity." Science, 2012, vol. 337, No. 6096, pp. 816-821.

Korenčić, D. et al., "A one-step method for in vitro production of tRNA transcripts," Nucleic Acids Res., 2002, vol. 30, No. 20, e105.

"Small RNA Assay User Guide—For LabChip GX Touch/GXII Touch" PerkinElmer, 2020, pp. 1-37.

Meyer, A.J. et al., "Transcription Yield of Fully 2'-Modified RNA Can be Increased by the Addition of Thermostabilizing Mutations to T7 RNA Polymerase Mutants," Nucleic Acids Research, 2015, vol. 43, No. 15, pp. 7480-7488.

Meyer, A.J. et al., "Directed evolution of a panel of orthogonal T7 RNA polymerase variants for in vivo or in vitro synthetic circuitry," ACS Synth. Biol., 2015, vol. 4, pp. 1070-1076.

Milligan, J.F. et al., "Synthesis of small RNAs using T7 RNA polymerase," Methods Enzymol., 1989, vol. 180, pp. 51-62.

Mullaly, G. et al., "5' modifications to CRISPR-Cas9 gRNA can change the dynamics and size of R-loops and inhibit DNA cleavage," Nucleic Acids Research, 2020, vol. 48, No. 12, pp. 6811-6823.

Murovec, J. et al., "New variants of CRISPR RNA-guided genome editing enzymes," Plant Biotechnology Journal, 2017, vol. 15, No. 8, pp. 917-926.

Padmanabhan, R. et al., "Promoter Length Affects the Initiation of T7 RNA Polymerase In Vitro: New Insights into Promoter/Polymerase Co-evolution," J Mol Evol, 2020, vol. 88, pp. 179-193.

Park, H.M. et al., "Extension of the crRNA enhances Cpf1 gene editing in vitro and in vivo," Nat Commun., 2018, vol. 9, 3313.

Raskin, C.A. et al., "T7 RNA polymerase mutants with altered promoter specificities," PNAS, 1993, vol. 90, pp. 3147-3151.

Safari, F. et al., "CRISPR Cpf1 proteins: structure, function and implications for genome editing" Cell & Bioscience, 2019, vol. 9, No. 36, pp. 1-21.

Yamano, T. et al., "Crystal structure of Cpf1 in complex with guide RNA and target DNA." Cell, 2016, vol. 165, No. 4, pp. 949-962.

Yang, Z. et al., "CRISPR-Cas12a/Cpf1-assisted precise, efficient and multiplexed genome-editing in Yarrowia lipolytica" Metabolic Engineering Communications, 2020, vol. 10, pp. 1-8.

Zhang, J.H. et al., "Optimization of genome editing through CRISPR-Cas9 engineering," Bioengineered, 2016, vol. 7, No. 3, pp. 166-174.

Cavac, E. et al., "High-salt transcription of DNA cotethered with T7 RNA polymerase to beads generates increased yields of highly pure RNA," JBC Research Article, 2021, vol. 297, No. 3, pp. 1-10.

International Search Report and Written Opinion issued in PCT/IB2021/000727, mailed Mar. 1, 2022.

International Preliminary Report on Patentability issued in PCT/IB2021/000727, dated Apr. 13, 2023.

Cavac, E. et al., High-salt transcription of DNA cotethered with T7 RNA polymerase to beads generates increased yields of highly pure RNA, JBC Research Article, vol. 297, 3 (2021):1-10.

Esposito, E.A. et al., Cross-linking of Promoter DNA to T7 RNA Polymerase Does Not Prevent Formation of a Stable Elongation Complex, The Journal of Biological Chemistry, vol. 279, 43 (2004):44270-44276.

Gholamalipour, Y. et al., 3' end addition by T7 RNA polymerase are RNA self-templated, distributive and diverse character—RNA-Seq analysis, Nucleic Acids Research, vol. 46, 18 (2018):9253-9263.

Gholamalipour, Y. et al., Efficient inhibition of RNA self-primed extension by addition of competing 3'-capture DNA-improved RNA synthesis by T7 RNA polymerase, Nucleic Acids Research, vol. 47, 19 (2019):e118.

Liu, C. et al., Promoter clearance by T7 RNA polymerase. Initial bubble collapse and transcript dissociation monitored by base analog fluorescence, The Journal of Biological Chemistry, vol. 277, 4 (2002):2725-2731.

Malagodapathiranage, K. et al., High-salt transcription from enzymatically gapped promoters nets higher yields and purity of transcribed RNAs, Nucleic Acids Research, vol. 51, 6 (2023):e36.

Martin, C.T. et al., Structure and function in promoter escape by T7 RNA polymerase, Progress in Nucleic Acid Research and Molecular Biology, vol. 80, (2005):1-25.

Turingan, R.S. et al., Structural confirmation of a bent and open model for the initiation complex of T7 RNA polymerase, Biochemistry, vol. 46, 7 (2007):1714-1723.

Zhou, Y. et al., Observed instability of T7 RNA polymerase elongation complexes can be dominated by collision-induced "Bumping", The Journal of Biological Chemistry, vol. 281, 34 (2006):24441-24448.

* cited by examiner

SEQUENCE LISTING

```
Sequence total quantity: 41
SEQ ID NO: 1            moltype = AA   length = 883
FEATURE                 Location/Qualifiers
source                  1..883
                        mol_type = protein
                        organism = Escherichia virus T7
SEQUENCE: 1
MNTINIAKND FSDIELAAIP FNTLADHYGE RLAREQLALE HESYEMGEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEDTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFA                     883

SEQ ID NO: 2            moltype = DNA  length = 2649
FEATURE                 Location/Qualifiers
source                  1..2649
                        mol_type = unassigned DNA
                        organism = Escherichia virus T7
SEQUENCE: 2
atgaacacga ttaacatcgc taagaacgac ttctctgaca tcgaactggc tgctatcccg     60
ttcaacactc tggctgacca ttacggtgag cgtttagctc gcgaacagtt ggccctgag    120
catgagtctt acgagatggg tgaagcacgc ttccgcaaga tgtttgagcg tcaacttaaa   180
gctggtgagg ttgcggataa cgctgccgcc aagcctctca tcactaccct actccctaag   240
atgattgcac gcatcaacga ctggtttgag gaagtgaaag ctaagcgcgg caagcgcccg   300
acagccttcc agttcctgca agaaatcaag ccggaagccg tagcgtacat caccattaag   360
accactctgg cttgcctaac cagtgctgac aatacaaccg ttcaggctgt agcaagcgca   420
atcggtcggg ccattgagga cgaggctcgc ttcggtcgta tccgtgacct tgaagctaag   480
cacttcaaga aaacgttga ggaacaactc aacaagcgcg tagggcacgt ctacaagaa    540
gcatttatgc aagttgtcga ggctgacatg ctctctaagg gtctactcgg tggcgaggcg   600
tggtcttcgt ggcataagga agactctatt catgtaggag tacgctgcat cgagatgctc   660
attgagtcaa ccggaatggt tagcttacac gccaaaatg ctggcgtagt aggtcaagac   720
tctgagacta tcgaactcgc acctgaatac gctgaggcta tcgcaacccg tgcaggtgcg   780
ctggctggca tctctccgat gttccaacct tgcgtagttc ctcctaagcc gtggactggc   840
attactggtg gtggctattg ggctaacggt cgtcgtcctc tggcgctggt gcgtactcac   900
agtaagaaag cactgatgcg ctacgaagac gtttacatgc ctgaggtgta caaagcgatt   960
aacattgcgc aaaacaccgc atggaaaatc aacaagaaag tcctagccgg cgccaacgta  1020
atcaccaagt ggaagcattg tccggtcgag gacatccctg cgattgagcg tgaagaactc  1080
ccgatgaaac cggaagacat cgacatgaat cctgaggctc taaccgcctg gaaacgtgct  1140
gccgctgctg tgtaccgcaa ggacaaggct cgcaagtctc gccgtatcag ccttgagttc  1200
atgcttgagc aagccaataa gtttgctaac cataaggcca tctggttccc ttacaacatg  1260
gactggcgcg gtcgtgttta cgctgtgtca atgttcaacc cgcaaggtaa cgatatgacc  1320
aaaggactgc ttacgctggc gaaaggtaaa ccaatcggta aggaaggtta ctactggctg  1380
aaaatccacg gtgcaaactg tgcgggtgtc gataaggttc cgttccctga gcgcatcaag  1440
```

```
ttcattgagg aaaaccacga gaacatcatg gcttgcgcta agtctccact ggagaacact   1500
tggtgggctg agcaagattc tccgttctgc ttccttgcgt tctgctttga gtacgctggg   1560
gtacagcacc acggcctgag ctataactgc tcccttccgc tggcgtttga cgggtcttgc   1620
tctggcatcc agcacttctc cgcgatgctc cgagatgagg taggtggtcg cgcggttaac   1680
ttgcttccta gtgaaaccgt tcaggacatc tacgggattg ttgctaagaa agtcaacgag   1740
attctacaag cagacgcaat caatgggacc gataacgaag tagttaccgt gaccgatgag   1800
aacactggtg aaatctctga gaaagtcaag ctgggcacta aggcactggc tggtcaatgg   1860
ctggcttacg gtgttactcg cagtgtgact aagcgttcag tcatgacgct ggcttacggg   1920
tccaaagagt tcggcttccg tcaacaagtg ctggaagata ccattcagcc agctattgat   1980
tccggcaagg gtctgatgtt cactcagccg aatcaggctg ctggatacat ggctaagctg   2040
atttgggaat ctgtgagcgt gacggtggta gctgcggttg aagcaatgaa ctggcttaag   2100
tctgctgcta agctgctggc tgctgaggtc aaagataaga agactggaga gattcttcgc   2160
aagcgttgcg ctgtgcattg ggtaactcct gatggtttcc ctgtgtggca ggaatacaag   2220
aagcctattc agacgcgctt gaacctgatg ttcctccggtc agttccgcct acagcctacc   2280
attaacacca acaaagatag cgagattgat gcacacaaac aggagtctgg tatcgctcct   2340
aactttgtac acagccaaga cggtagccac cttcgtaaga ctgtagtgtg ggcacacgag   2400
aagtacgaaa tcgaatcttt tgcactgatt cacgactcct tcggtaccat tccggctgac   2460
gctgcgaacc tgttcaaagc agtgcgcgaa actatggttg aacacatatga gtcttgctgg   2520
gtactggctg atttctacga ccagttcgct gaccagttgc acgagtctca attggacaaa   2580
atgccagcac ttccggctaa aggtaacttg aacctccgtg acatcttaga gtcggacttc   2640
gcgttcgcg                                                           2649

SEQ ID NO: 3              moltype = DNA  length = 27
FEATURE                   Location/Qualifiers
misc_feature              1..27
                          note = Description of Unknown:T7 RNA polymerase promoter
                            sequence
source                    1..27
                          mol_type = other DNA
                          organism = unidentified
SEQUENCE: 3
ttaaattaat acgactcact atatata                                       27

SEQ ID NO: 4              moltype = DNA  length = 14
FEATURE                   Location/Qualifiers
misc_feature              1..14
                          note = Description of Artificial Sequence:
                            Syntheticoligonucleotide
source                    1..14
                          mol_type = other DNA
                          organism = synthetic construct
SEQUENCE: 4
tacgactcac tata                                                     14

SEQ ID NO: 5              moltype = DNA  length = 16
FEATURE                   Location/Qualifiers
misc_feature              1..16
                          note = Description of Artificial Sequence:
                            Syntheticoligonucleotide
source                    1..16
                          mol_type = other DNA
                          organism = synthetic construct
SEQUENCE: 5
aatacgactc actata                                                   16

SEQ ID NO: 6              moltype = DNA  length = 18
FEATURE                   Location/Qualifiers
misc_feature              1..18
                          note = Description of Artificial Sequence:
                            Syntheticoligonucleotide
source                    1..18
                          mol_type = other DNA
                          organism = synthetic construct
SEQUENCE: 6
ttaatacgac tcactata                                                 18

SEQ ID NO: 7              moltype = DNA  length = 43
FEATURE                   Location/Qualifiers
misc_feature              1..43
                          note = Description of Artificial Sequence:
                            Syntheticoligonucleotide
source                    1..43
                          mol_type = other DNA
                          organism = synthetic construct
SEQUENCE: 7
tatagtgagt cgtattaatt tacaacaaaa ttaatacgac tca                     43

SEQ ID NO: 8              moltype = AA  length = 329
FEATURE                   Location/Qualifiers
```

```
REGION                   1..329
                         note = Description of Artificial Sequence:
                              Syntheticpolypeptide
source                   1..329
                         mol_type = protein
                         organism = synthetic construct
SEQUENCE: 8
NLISLFSGAG GLDLGFQKAG FRIICANEYD KSIWKTYESN HSAKLIKGDI SKISSDEFPK    60
CDGIIGGPPC QSWSEGGSLR GIDDPRGKLF YEYIRILKQK KPIFFLAENV KGMMAQRHNK   120
AVQEFIQEFD NAGYDVHIIL LNANDYGVAQ DRKRVFYIGF RKELNINYLP PIPHLIKPTF   180
KDVIWDLKDN PIPALDKNKT NGNKCIYPNH EYFIGSYSTI FMSRNRVRQW NEPAFTVQAS   240
GRQCQLHPQA PVMLKVSKNL NKFVEGKEHL YRRLTVRECA RVQGFPDDFI FHYESLNDGY   300
KMIGNAVPVN LAYEIAKTIK SALEICKGN                                    329

SEQ ID NO: 9             moltype = AA  length = 128
FEATURE                  Location/Qualifiers
REGION                   1..128
                         note = Description of Artificial Sequence:
                              Syntheticpolypeptide
source                   1..128
                         mol_type = protein
                         organism = synthetic construct
SEQUENCE: 9
FDASNFKDFS SIASASSSWQ NQHGSTMIIQ VDSFGNVSGQ YVNRAEGTGC QNSPYPLTGR    60
VNGTFIDFSV KWNNSTENCN SNTQWTGYAQ VNGNNTEIVT RWNLKYEGGS GPAIWQGQDT   120
FQYVPTTE                                                           128

SEQ ID NO: 10            moltype = AA  length = 17
FEATURE                  Location/Qualifiers
REGION                   1..17
                         note = Description of Artificial Sequence: Syntheticpeptide
source                   1..17
                         mol_type = protein
                         organism = synthetic construct
SEQUENCE: 10
GSGGGGSGGG GSGGGGS                                                  17

SEQ ID NO: 11            moltype = AA  length = 12
FEATURE                  Location/Qualifiers
REGION                   1..12
                         note = Description of Artificial Sequence: Syntheticpeptide
source                   1..12
                         mol_type = protein
                         organism = synthetic construct
SEQUENCE: 11
GSGGGGSGGG GS                                                       12

SEQ ID NO: 12            moltype = AA  length = 22
FEATURE                  Location/Qualifiers
REGION                   1..22
                         note = Description of Artificial Sequence: Syntheticpeptide
source                   1..22
                         mol_type = protein
                         organism = synthetic construct
SEQUENCE: 12
GSGGGGSGGG GSGGGGSGGG GS                                            22

SEQ ID NO: 13            moltype = AA  length = 16
FEATURE                  Location/Qualifiers
REGION                   1..16
                         note = Description of Artificial Sequence: Syntheticpeptide
source                   1..16
                         mol_type = protein
                         organism = synthetic construct
SEQUENCE: 13
SGSETPGTSE SATPES                                                   16

SEQ ID NO: 14            moltype = DNA  length = 49
FEATURE                  Location/Qualifiers
misc_feature             1..49
                         note = Description of Artificial Sequence:
                              Syntheticoligonucleotide
source                   1..49
                         mol_type = other DNA
                         organism = synthetic construct
SEQUENCE: 14
gagcccacac tctactcgac agatacgaat atctggaccc gaccgtctc                49

SEQ ID NO: 15            moltype = DNA  length = 11
```

```
                        -continued

FEATURE                 Location/Qualifiers
misc_feature            1..11
                        note = Description of Artificial Sequence:
                        Syntheticoligonucleotide
source                  1..11
                        mol_type = other DNA
                        organism = synthetic construct
SEQUENCE: 15
tatagtgagt c                                                              11

SEQ ID NO: 16           moltype = DNA  length = 10
FEATURE                 Location/Qualifiers
misc_feature            1..10
                        note = Description of Artificial Sequence:
                        Syntheticoligonucleotide
source                  1..10
                        mol_type = other DNA
                        organism = synthetic construct
SEQUENCE: 16
gtattaattt                                                                10

SEQ ID NO: 17           moltype = DNA  length = 77
FEATURE                 Location/Qualifiers
misc_feature            1..77
                        note = Description of Artificial Sequence:
                        Syntheticoligonucleotide
source                  1..77
                        mol_type = other DNA
                        organism = synthetic construct
SEQUENCE: 17
aagagcccac actctactcg acagatacga atatctggac ccgaccgtct cgatcctata         60
gtgagtcgta ttaattt                                                        77

SEQ ID NO: 18           moltype = DNA  length = 77
FEATURE                 Location/Qualifiers
misc_feature            1..77
                        note = Description of Artificial Sequence:
                        Syntheticoligonucleotide
source                  1..77
                        mol_type = other DNA
                        organism = synthetic construct
SEQUENCE: 18
aagagcccac actctactcg acagatacga atatctggac ccgaccgtct cgatcctata         60
gtgagtcgta ttaatgg                                                        77

SEQ ID NO: 19           moltype = DNA  length = 77
FEATURE                 Location/Qualifiers
misc_feature            1..77
                        note = Description of Artificial Sequence:
                        Syntheticoligonucleotide
source                  1..77
                        mol_type = other DNA
                        organism = synthetic construct
SEQUENCE: 19
aagagcccac actctactcg acagatacga atatctggac ccgaccgtct cgatcctata         60
gtgagtcgta ttaggct                                                        77

SEQ ID NO: 20           moltype = DNA  length = 77
FEATURE                 Location/Qualifiers
misc_feature            1..77
                        note = Description of Artificial Sequence:
                        Syntheticoligonucleotide
source                  1..77
                        mol_type = other DNA
                        organism = synthetic construct
SEQUENCE: 20
aagagcccac actctactcg acagatacga atatctggac ccgaccgtct cgatcctata         60
gtgagtcgta tggctag                                                        77

SEQ ID NO: 21           moltype = DNA  length = 77
FEATURE                 Location/Qualifiers
misc_feature            1..77
                        note = Description of Artificial Sequence:
                        Syntheticoligonucleotide
source                  1..77
                        mol_type = other DNA
                        organism = synthetic construct
SEQUENCE: 21
aagagcccac actctactcg acagatacga atatctggac ccgaccgtct cgatcctata         60
```

```
gtgagtcgtg gctagcg                                              77

SEQ ID NO: 22          moltype = DNA  length = 77
FEATURE                Location/Qualifiers
misc_feature           1..77
                       note = Description of Artificial Sequence:
                       Syntheticoligonucleotide
source                 1..77
                       mol_type = other DNA
                       organism = synthetic construct
SEQUENCE: 22
aagagcccac actctactcg acagatacga atatctggac ccgaccgtct cgatcctata  60
gtgagtcggc tagcgat                                                77

SEQ ID NO: 23          moltype = AA  length = 4
FEATURE                Location/Qualifiers
REGION                 1..4
                       note = Description of Artificial Sequence: Syntheticpeptide
source                 1..4
                       mol_type = protein
                       organism = synthetic construct
SEQUENCE: 23
SGGS                                                               4

SEQ ID NO: 24          moltype = AA  length = 120
FEATURE                Location/Qualifiers
REGION                 1..120
                       note = Description of Artificial Sequence:
                       Syntheticpolypeptide
SITE                   1..120
                       note = This sequence may encompass 1-30 "Ser Gly Gly
                       Ser"repeating units
source                 1..120
                       mol_type = protein
                       organism = synthetic construct
SEQUENCE: 24
SGGSSGGSSG GSSGGSSGGS SGGSSGGSSG GSSGGSSGGS SGGSSGGSSG GSSGGSSGGS   60
SGGSSGGSSG GSSGGSSGGS SGGSSGGSSG GSSGGSSGGS SGGSSGGSSG GSSGGSSGGS  120

SEQ ID NO: 25          moltype = AA  length = 120
FEATURE                Location/Qualifiers
REGION                 1..120
                       note = Description of Artificial Sequence:
                       Syntheticpolypeptide
SITE                   1..120
                       note = This sequence may encompass 1-30 "Gly Gly Gly
                       Ser"repeating units
source                 1..120
                       mol_type = protein
                       organism = synthetic construct
SEQUENCE: 25
GGGSGGGSGG GSGGGSGGGS GGGSGGGSGG GSGGGSGGGS GGGSGGGSGG GSGGGSGGGS   60
GGGSGGGSGG GSGGGSGGGS GGGSGGGSGG GSGGGSGGGS GGGSGGGSGG GSGGGSGGGS  120

SEQ ID NO: 26          moltype = AA  length = 150
FEATURE                Location/Qualifiers
REGION                 1..150
                       note = Description of Artificial Sequence:
                       Syntheticpolypeptide
SITE                   1..150
                       note = This sequence may encompass 1-30 "Gly Gly Gly Gly
                       Ser"repeating units
source                 1..150
                       mol_type = protein
                       organism = synthetic construct
SEQUENCE: 26
GGGGSGGGGS GGGGSGGGGS GGGGSGGGGS GGGGSGGGGS GGGGSGGGGS GGGGSGGGGS   60
GGGGSGGGGS GGGGSGGGGS GGGGSGGGGS GGGGSGGGGS GGGGSGGGGS GGGGSGGGGS  120
GGGGSGGGGS GGGGSGGGGS GGGGSGGGGS                                  150

SEQ ID NO: 27          moltype = AA  length = 30
FEATURE                Location/Qualifiers
REGION                 1..30
                       note = Description of Artificial Sequence:
                       Syntheticpolypeptide
SITE                   1..30
                       note = This sequence may encompass 1-30 residues
source                 1..30
                       mol_type = protein
```

```
                        organism = synthetic construct
SEQUENCE: 27
GGGGGGGGGG GGGGGGGGGG GGGGGGGGGG                                    30

SEQ ID NO: 28           moltype = AA   length = 150
FEATURE                 Location/Qualifiers
REGION                  1..150
                        note = Description of Artificial Sequence:
                        Syntheticpolypeptide
SITE                    1..150
                        note = This sequence may encompass 1-30 "Glu Ala Ala Ala
                        Lys"repeating units
source                  1..150
                        mol_type = protein
                        organism = synthetic construct
SEQUENCE: 28
EAAAKEAAAK EAAAKEAAAK EAAAKEAAAK EAAAKEAAAK EAAAKEAAAK EAAAKEAAAK    60
EAAAKEAAAK EAAAKEAAAK EAAAKEAAAK EAAAKEAAAK EAAAKEAAAK EAAAKEAAAK   120
EAAAKEAAAK EAAAKEAAAK EAAAKEAAAK                                   150

SEQ ID NO: 29           moltype = AA   length = 90
FEATURE                 Location/Qualifiers
REGION                  1..90
                        note = Description of Artificial Sequence:
                        Syntheticpolypeptide
SITE                    1..90
                        note = This sequence may encompass 1-30 "Gly Gly
                        Ser"repeating units
source                  1..90
                        mol_type = protein
                        organism = synthetic construct
SEQUENCE: 29
GGSGGSGGSG GSGGSGGSGG SGGSGGSGGS GGSGGSGGSG GSGGSGGSGG SGGSGGSGGS    60
GGSGGSGGSG GSGGSGGSGG SGGSGGSGGS                                    90

SEQ ID NO: 30           moltype = AA   length = 122
FEATURE                 Location/Qualifiers
REGION                  1..122
                        note = Description of Artificial Sequence:
                        Syntheticpolypeptide
SITE                    3..122
                        note = This sequence may encompass 1-30 "Gly Gly Gly
                        Ser"repeating units
source                  1..122
                        mol_type = protein
                        organism = synthetic construct
SEQUENCE: 30
GSGGGSGGGS GGGSGGGSGG GSGGGSGGGS GGGSGGGSGG GSGGGSGGGS GGGSGGGSGG    60
GSGGGSGGGS GGGSGGGSGG GSGGGSGGGS GGGSGGGSGG GSGGGSGGGS GGGSGGGSGG   120
GS                                                                 122

SEQ ID NO: 31           moltype = AA   length = 152
FEATURE                 Location/Qualifiers
REGION                  1..152
                        note = Description of Artificial Sequence:
                        Syntheticpolypeptide
SITE                    3..152
                        note = This sequence may encompass 1-30 "Gly Gly Gly Gly
                        Ser"repeating units
source                  1..152
                        mol_type = protein
                        organism = synthetic construct
SEQUENCE: 31
GSGGGGSGGG GSGGGGSGGG GSGGGGSGGG GSGGGGSGGG GSGGGGSGGG GSGGGGSGGG    60
GSGGGGSGGG GSGGGGSGGG GSGGGGSGGG GSGGGGSGGG GSGGGGSGGG GSGGGGSGGG   120
GSGGGGSGGG GSGGGGSGGG GSGGGGSGGG GS                                152

SEQ ID NO: 32           moltype = AA   length = 60
FEATURE                 Location/Qualifiers
REGION                  1..60
                        note = Description of Artificial Sequence:
                        Syntheticpolypeptide
MOD_RES                 1
                        note = Any amino acid
MOD_RES                 3
                        note = Any amino acid
MOD_RES                 5
                        note = Any amino acid
MOD_RES                 7
```

|  |  |
|---|---|
|  | note = Any amino acid |
| MOD_RES | 9 |
|  | note = Any amino acid |
| MOD_RES | 11 |
|  | note = Any amino acid |
| MOD_RES | 13 |
|  | note = Any amino acid |
| MOD_RES | 15 |
|  | note = Any amino acid |
| MOD_RES | 17 |
|  | note = Any amino acid |
| MOD_RES | 19 |
|  | note = Any amino acid |
| MOD_RES | 21 |
|  | note = Any amino acid |
| MOD_RES | 23 |
|  | note = Any amino acid |
| MOD_RES | 25 |
|  | note = Any amino acid |
| MOD_RES | 27 |
|  | note = Any amino acid |
| MOD_RES | 29 |
|  | note = Any amino acid |
| MOD_RES | 31 |
|  | note = Any amino acid |
| MOD_RES | 33 |
|  | note = Any amino acid |
| MOD_RES | 35 |
|  | note = Any amino acid |
| MOD_RES | 37 |
|  | note = Any amino acid |
| MOD_RES | 39 |
|  | note = Any amino acid |
| MOD_RES | 41 |
|  | note = Any amino acid |
| MOD_RES | 43 |
|  | note = Any amino acid |
| MOD_RES | 45 |
|  | note = Any amino acid |
| MOD_RES | 47 |
|  | note = Any amino acid |
| MOD_RES | 49 |
|  | note = Any amino acid |
| MOD_RES | 51 |
|  | note = Any amino acid |
| MOD_RES | 53 |
|  | note = Any amino acid |
| MOD_RES | 55 |
|  | note = Any amino acid |
| MOD_RES | 57 |
|  | note = Any amino acid |
| MOD_RES | 59 |
|  | note = Any amino acid |
| SITE | 1..60 |
|  | note = This sequence may encompass 1-30 "Xaa Pro"repeating units |
| source | 1..60 |
|  | mol_type = protein |
|  | organism = synthetic construct |
| SEQUENCE: 32 |  |
| XPXPXPXPXP XPXPXPXPXP XPXPXPXPXP XPXPXPXPXP XPXPXPXPXP XPXPXPXPXP   60 |  |
|  |  |
| SEQ ID NO: 33 | moltype = AA   length = 5 |
| FEATURE | Location/Qualifiers |
| REGION | 1..5 |
|  | note = Description of Artificial Sequence: Syntheticpeptide |
| source | 1..5 |
|  | mol_type = protein |
|  | organism = synthetic construct |
| SEQUENCE: 33 |  |
| PAPAP                                                                5 |  |
|  |  |
| SEQ ID NO: 34 | moltype = AA   length = 6 |
| FEATURE | Location/Qualifiers |
| REGION | 1..6 |
|  | note = Description of Artificial Sequence: Syntheticpeptide |
| source | 1..6 |
|  | mol_type = protein |
|  | organism = synthetic construct |

```
SEQUENCE: 34
PAPAPA                                                                       6

SEQ ID NO: 35           moltype = AA  length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 35
PAPAPAP                                                                      7

SEQ ID NO: 36           moltype = AA  length = 8
FEATURE                 Location/Qualifiers
REGION                  1..8
                        note = Description of Artificial Sequence: Syntheticpeptide
source                  1..8
                        mol_type = protein
                        organism = synthetic construct
SEQUENCE: 36
PAPAPAPA                                                                     8

SEQ ID NO: 37           moltype = AA  length = 21
FEATURE                 Location/Qualifiers
REGION                  1..21
                        note = Description of Artificial Sequence: Syntheticpeptide
SITE                    2..21
                        note = This sequence may encompass 1-10 "Ala Pro"repeating
                         units
source                  1..21
                        mol_type = protein
                        organism = synthetic construct
SEQUENCE: 37
PAPAPAPAPA PAPAPAPAPA P                                                     21

SEQ ID NO: 38           moltype = AA  length = 52
FEATURE                 Location/Qualifiers
REGION                  1..52
                        note = Description of Artificial Sequence:
                         Syntheticpolypeptide
SITE                    3..52
                        note = This sequence may encompass 1-10 "Gly Gly Gly Gly
                         Ser"repeating units
source                  1..52
                        mol_type = protein
                        organism = synthetic construct
SEQUENCE: 38
GSGGGGSGGG GSGGGGSGGG GSGGGGSGGG GSGGGGSGGG GSGGGGSGGG GS                   52

SEQ ID NO: 39           moltype = RNA  length = 21
FEATURE                 Location/Qualifiers
misc_feature            1..21
                        note = Description of Artificial Sequence:
                         Syntheticoligonucleotide
source                  1..21
                        mol_type = other RNA
                        organism = synthetic construct
SEQUENCE: 39
ggtagtaata tacacccaat g                                                     21

SEQ ID NO: 40           moltype = DNA  length = 21
FEATURE                 Location/Qualifiers
misc_feature            1..21
                        note = Description of Unknown:Target DNA sequence
source                  1..21
                        mol_type = other DNA
                        organism = unidentified
SEQUENCE: 40
cattgggtgt atattactaa t                                                     21

SEQ ID NO: 41           moltype = RNA  length = 19
FEATURE                 Location/Qualifiers
misc_feature            1..19
                        note = Description of Artificial Sequence:
                         Syntheticoligonucleotide
source                  1..19
                        mol_type = other RNA
                        organism = synthetic construct
```

| SEQUENCE: 41 | |
|---|---|
| tagtaatata cacccaatg | 19 |

COMPOSITIONS AND METHODS FOR RNA SYNTHESIS

CROSS-REFERENCE

This application is a continuation of International Application No. PCT/IB2021/000727, filed on Oct. 22, 2021, which claims the benefit of U.S. Provisional Application No. 63/104,735, filed on Oct. 23, 2020, each of which is incorporated by reference herein in its entirety.

SEQUENCE LISTING

The instant application contains a Sequence Listing which has been submitted electronically in XML format and is hereby incorporated by reference in its entirety. Said XML copy, created on Mar. 2, 2023, is named 59306-701_301_SL.xml and is 74,186 bytes in size.

BACKGROUND

As RNA molecules play important and diverse roles in the cell, RNA-based therapeutics have been attractive classes of drugs for treating a variety of diseases. There have been significant advances in RNA therapeutics to regulate gene expression by delivering messenger RNAs (mRNA) of a gene of an interest, or non-coding RNAs such as micro RNAs (miRNAs), short interfering RNAs (siRNAs), and antisense oligonucleotides (ASOs). In addition, guide RNAs (gRNAs) for Clustered Regularly Interspaced Short Palindromic Repeats (CRISPR)-CRISPR associated (Cas) protein system plays an essential role in guiding CRISPR-Cas system to the target site for genome editing. The use of synthetic RNAs in place of plasmid DNA provides a more reliable approach with minimized off-target activity due to the relatively short half-life of RNA molecules.

Currently available RNA synthesis methodologies include chemical synthesis for short RNA molecules and enzymatic synthesis such as in vitro transcription (IVT) for long RNA molecules. While chemical synthesis provides pure, high-quality RNA molecules and offers wide variety of position-specific custom modifications, it suffers from expensive scale up cost and low speed. IVT offers a less expensive solution, however, it tends to be error-prone, labor-intensive, and allows limited sequence edits. There remains a need to develop an RNA synthesis platform that is fast, accurate, automated, scalable, and cost-effective.

SUMMARY

In one aspect, provided herein, is a method for synthesizing RNAs, comprising providing an RNA polymerase immobilized on a surface, and synthesizing a plurality of gRNAs at a rate of extension of at least 50 nucleotides per hour, wherein each of the gRNAs has a preselected sequence, and wherein the synthesizing comprises extending by a single base in an extension reaction. In another aspect, provided herein, is a method for synthesizing RNAs, comprising providing a fusion RNA polymerase or a functional fragment or a variant thereof, and synthesizing a plurality of gRNAs at a rate of extension of at least 50 nucleotides per hour, wherein each of the gRNAs has a preselected sequence, and wherein the synthesizing comprises extending by a single base in an extension reaction. In some embodiments, the rate of extension is at least 50 nucleotides per minute. In some embodiments, the rate of extension is at least 50 nucleotides per second.

In another aspect, provided herein, is a nucleic acid library, comprising a plurality of purified RNAs and at least one single-stranded DNA (ssDNA) encoding a truncated RNA polymerase promoter region. Also provided herein is a nucleic acid library, comprising a plurality of purified guide RNAs (gRNAs) of at least 80 nucleotides in length, and at least one oligonucleotide of 2 to 10 nucleotides in length. In some aspects, provided herein, is a method for making a nucleic acid library comprising at least 50 guide RNAs (gRNAs), the method comprising synthesizing at least 50 gRNAs using an RNA polymerase, wherein at least one of the at least 50 gRNAs comprises a spacer sequence complementary to a target sequence in a target gene, and wherein a 5' terminal nucleotide of the spacer sequence is complementary to a 3' terminal nucleotide of the target sequence. In some aspects, provided herein, is a nucleic acid library comprising at least 50 purified guide RNAs (gRNAs), wherein the at least 50 purified gRNAs comprise gRNA sequences comprising a 5' terminal guanine (G) analog.

In some aspects, provided herein, is a nucleic acid library, wherein the nucleic acid library comprises at least 50 RNAs, wherein each of the at least 50 RNAs encodes a different guide RNA (gRNA) sequence, and wherein at least about 90% of the at least 50 RNAs are each present in the nucleic acid library in an amount within 1.5× of a mean frequency for the at least 50 RNAs in the library. In some embodiments, at least about 95% of the at least 50 RNAs are each present in the nucleic acid library in an amount within 1.5× of a mean frequency for the at least 50 RNAs in the library. In some embodiments, at least about 99% of the at least 50 RNAs are each present in the nucleic acid library in an amount within 1.5× of a mean frequency for the at least 50 RNAs in the library.

In one aspect, provided herein, is a modified polypeptide composition, wherein the modified polypeptide composition comprises a purified RNA polymerase or a functional fragment or variant thereof and a purified nucleic acid binding protein, optionally a zinc finger containing protein, or a functional fragment or variant thereof, wherein the purified RNA polymerase and the nucleic acid binding protein are heterologous, and wherein the purified RNA polymerase and the purified nucleic acid binding protein are linked. In another aspect, provided herein, is a composition, comprising a fusion RNA polymerase or a functional fragment or variant thereof, wherein the fusion RNA polymerase comprises (i) an RNA polymerase or fragment thereof; and (ii) a DNA binding protein, wherein the RNA polymerase and the DNA binding protein are heterologous; and a DNA polynucleotide.

In one aspect, provided herein, is a modified polypeptide, wherein the modified polypeptide comprises a variant T7 RNA polymerase or a functional fragment thereof, wherein the variant T7 RNA polymerase comprises at least four variations selected from the group consisting of K172L, P266L, H772R, N748X, R756M, Q758X, and E775V, wherein the position is determined by alignment with SEQ ID NO: 1. In another aspect, provided herein, is a modified polypeptide, wherein the modified polypeptide comprises a variant T7 RNA polymerase or a functional fragment thereof, wherein the variant T7 RNA polymerase comprises at least one variation selected from the group consisting of K172L, P266L, H772R, N748X, R756M, Q758X, and E775V, wherein the position is determined by alignment with SEQ ID NO: 1, and wherein the modified polypeptide is immobilized on a surface.

In one aspect, provided herein, is a device comprising a surface; a nucleic acid binding protein, or a functional fragment or a variant thereof linked to the surface; a T7 RNA polymerase or a variant thereof linked to the DNA binding protein; and a DNA template, wherein the DNA template comprises a truncated T7 promoter sequence.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The features of the present disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 5 discloses SEQ ID NOs: 39 and 40, respectively, in order of appearance.

FIG. 6 discloses SEQ ID NOs: 41 and 40, respectively, in order of appearance.

DETAILED DESCRIPTION

Figure 1:
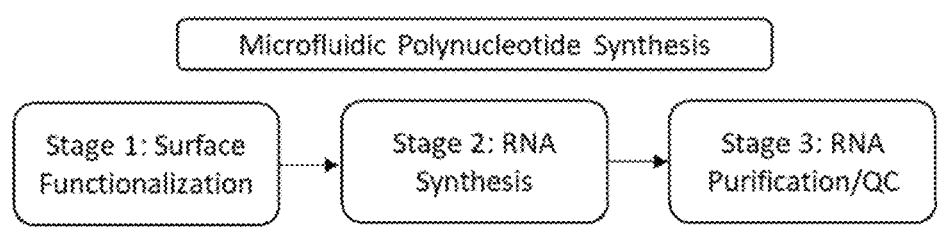
FIG. 1 depicts a schematic of an exemplary workflow for microfluidic polynucleotide synthesis.

Provided herein are methods, compositions, and devices for producing polynucleotides using microfluidic workflow that allows rapid, highly efficient, accurate, and pure RNA generation. The methods, compositions, and devices described herein provide means to synthesize polynucleotides using efficient RNA polymerase enzyme, microfluidics, enhanced kinetics, reduced off-target effects. In some aspects, the methods, compositions, and devices described herein provide single unit cartridge-based portable systems for polynucleotide synthesis.

Definitions

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise. The terms "and/or" and "any combination thereof" and their grammatical equivalents as used herein, can be used interchangeably. These terms can convey that any combination is specifically contemplated. Solely for illustrative purposes, the following phrases "A, B, and/or C" or "A, B, C, or any combination thereof" can mean "A individually; B individually; C individually; A and B; B and C; A and C; and A, B, and C." The term "or" can be used conjunctively or disjunctively, unless the context specifically refers to a disjunctive use.

The term "about" or "approximately" can mean within an acceptable error range for the particular value as determined by one of ordinary skill in the art, which will depend in part on how the value is measured or determined, i.e. the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, within 5-fold, and more preferably within 2-fold, of a value. Where particular values are described in the application and claims, unless otherwise stated the term "about" meaning within an acceptable error range for the particular value should be assumed.

Throughout this disclosure, numerical features are presented in a range format. It should be understood that the description in range format is merely for convenience and brevity and should not be construed as an inflexible limitation on the scope of any embodiments. Accordingly, the description of a range should be considered to have specifically disclosed all the possible subranges as well as individual numerical values within that range to the tenth of the unit of the lower limit unless the context clearly dictates otherwise. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual values within that range, for example, 1.1, 2, 2.3, 5, and 5.9. This applies regardless of the breadth of the range. The upper and lower limits of these intervening ranges may independently be included in the smaller ranges, and are also encompassed within the invention, subject to any specifically excluded limit in the stated range. Where the stated range includes one or both of the limits, ranges excluding either or both of those included limits are also included in the invention, unless the context clearly dictates otherwise.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. It is contemplated that any embodiment discussed in this specification can be implemented with respect to any method or composition of the present disclosure, and vice versa. Furthermore, compositions of the present disclosure can be used to achieve methods of the present disclosure.

Reference in the specification to "some embodiments," "an embodiment," "one embodiment" or "other embodiments" means that a particular feature, structure, or characteristic described in connection with the embodiments is included in at least some embodiments, but not necessarily all embodiments, of the present disclosures. To facilitate an understanding of the present disclosure, a number of terms and phrases are defined below.

As used herein, the terms "preselected sequence," "predefined sequence," or "predetermined sequence" are used interchangeably. The terms mean that the sequence of the polynucleic acid is known and chosen before synthesis or assembly of the polynucleic acid. In particular, various aspects of the invention described herein primarily are with regard to the preparation of nucleic acid molecules, and the sequence of the polynucleic acid are known and chosen before the synthesis or assembly of the nucleic acid molecules.

The nomenclature used to describe polypeptides or proteins follows the conventional practice wherein the amino group is presented to the left (the amino- or N-terminus) and the carboxyl group to the right (the carboxy- or C-terminus) of each amino acid residue. When amino acid residue positions are referred to in a polypeptide or a protein, they are numbered in an amino to carboxyl direction with position one being the residue located at the amino terminal end of the polypeptide or the protein of which it can be a part. The amino acid sequences of peptides set forth herein are generally designated using the standard single letter symbol. (A, Alanine; C, Cysteine; D, Aspartic Acid; E, Glutamic Acid; F, Phenylalanine; G, Glycine; H, Histidine; I, Isoleucine; K, Lysine; L, Leucine; M, Methionine; N, Asparagine; P, Proline; Q, Glutamine; R, Arginine; S, Serine; T, Threonine; V, Valine; W, Tryptophan; and Y, Tyrosine).

Certain specific details of this description are set forth in order to provide a thorough understanding of various embodiments. However, one skilled in the art will understand that the present disclosure may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed disclosure.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods, and materials are described below.

Microfluidic Polynucleotide Synthesis, Device, and Systems

Provided herein are methods, compositions, devices, and systems for producing polynucleotides in a fast, pure, and accurate way. Also provided herein are devices and systems for producing polynucleotide using microfluidics enhanced kinetics and single unit cartridge-based systems that allow highly accurate and efficient polynucleotide synthesis with reduced off-target effects. The terms oligonucleotide, oligo, and polynucleotide are defined to be synonymous throughout. Libraries of nucleic acids (e.g., DNAs or RNAs), described herein, may comprise a plurality of polynucleotides collectively encoding coding or non-coding RNA sequences. In some instances, coding sequences can comprise messenger RNAs (mRNAs). In some instances, non-coding sequences can comprise guide RNAs (gRNAs), microRNAs (miRNAs), small interfering RNAs (siRNAs), short hairpin RNAs (shRNAs), piwi-interacting RNA (piRNA), RNA aptamers, transfer RNA (tRNA), or anti-sense oligonucleotides (ASOs). In some instances, the nucleic acid library comprises a plurality of polynucleotides and each polynucleotide may encode a different sequence.

Provided herein are methods, compositions, devices, and systems for production of polynucleotides using microfluidic workflow. Microfluidics utilizes the science of controlling and manipulating fluids, in the range of µL to pL, in networks of channels that are geometrically constrained to a small scale (10 s-100 s µm) at which capillary penetration directs mass transport. Microfluidics offer many advantages including decreased sample and reagent consumptions, shorter time of experiments, and reduced overall cost of application. In addition, microfluidics allows automation and miniaturization of the polynucleotide synthesis, which can improve the precision and accuracy of the synthesis and permit highly rapid synthesis by simultaneously operating multiple chambers in one microfluidic chip or cartridge.

Figure 2:
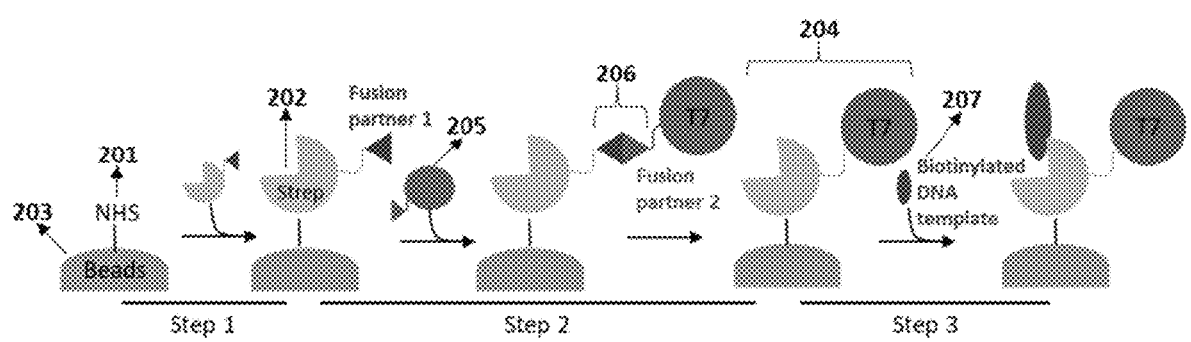
FIG. 2 depicts a schematic of an exemplary process of the surface functionalization for microfluidic polynucleotide synthesis.
Figure 4:
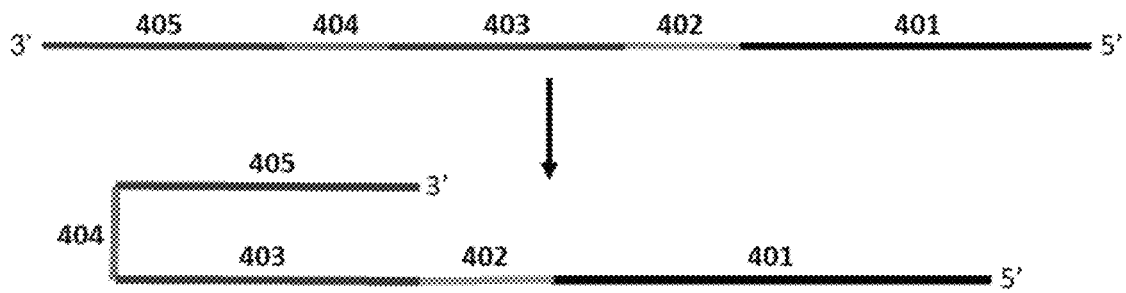
FIG. 4 depicts a schematic representation of the DNA template for RNA transcription (top) and its predicted secondary hairpin structure (bottom). V: template for RNA transcription, W: DNA melting region, X: a sequence that is reverse complement to the polymerase promoter sequence Z and hybridizes with Z, Y: a loop region connecting X and Z, and Z: polymerase promoter sequence that hybridizes with X.

In an exemplary workflow, microfluidic polynucleotide synthesis in a cartridge described herein can comprise 3 Stages: Surface functionalization, RNA synthesis, and RNA purification and quality control (FIG. 1). In Stage 1, a surface is functionalized to set up a transcription system in a microfluidic cartridge. A surface may be functionalized by activating the surface with a functional group including, but not limited to, N-hydroxysuccinimide esters (NHS) functional group, trifluoracetic anhydride (TFAA) functional group, or glutaraldehyde (GA) functional group. For example, a surface, such as magnetic or agarose beads that are activated with standard N-hydroxy-succinimide (NHS) functional groups is provided in each reaction chamber of a microfluidic cartridge to support the attachment and synthesis of polynucleotides (FIGS. 1 and 2). The NHS functional group 201 may react with primary amines on a target protein, for example, a DNA binding protein or functional fragment thereof such as streptavidin (strep) 202, forming stable amide linkages (Step 1 in FIG. 2). NHS reaction can then be quenched before other necessary elements (e.g., transcription proteins) required for microfluidic polynucleotide synthesis are added. This two-step reaction may protect other transcription complex proteins, including polymerases, from NHS reaction chemistry. The resulting immobilized proteins, that are covalently conjugated to the beads 203, may be highly resistant to leaching from the bead surface. Each bead represents one chamber from which one synthesis reaction can occur in FIG. 2; however, more than one bead may be provided in each chamber. The transcription complex 204 is then assembled (Step 2 in FIG. 2). As examples of polymerases, T7 RNA polymerases 205 are added and bind to the DNA binding proteins or functional fragments thereof (e.g., strep, or zinc finger array protein) through fusion partner interactions 206 (blue and purple triangles in Step 2 in FIG. 2) to form a stable transcription complex 204, optionally with linkers to connect the DNA binding protein with the fusion partner 1 and the polymerase with the fusion partner 2. DNA templates are then added and bind to the DNA binding protein or functional fragment thereof (Step 3 in FIG. 2). For example, DNA templates can be biotinylated 207 for interaction with Strep as shown in FIG. 2. In another example, DNA templates can comprise a DNA binding target sequence (e.g., zinc finger array (ZFA) binding sequence) for interaction with a polymerase through a DNA binding protein (e.g., ZFA) fused with the polymerase. DNA templates as described herein can include double-stranded DNA (dsDNA), partially double-stranded DNA, or single-stranded DNA (ssDNA). DNA templates can be ssDNA comprising a secondary structure e.g., a hairpin (FIG. 4). DNA templates described herein may comprise a promoter region where RNA polymerase binds and initiates RNA synthesis. In some embodiments, a promoter region described herein may comprise an essential promoter region and/or a non-essential promoter region. RNA polymerases described herein can include a bacteriophage RNA polymerase, a bacterial RNA polymerase, or a eukaryotic RNA polymerase. Non-limiting examples of the phage RNA polymerase include T3 RNA polymerase, a T7 RNA polymerase, a KP34 RNA polymerase, a N4 RNA polymerase, and a SP6 RNA polymerase. For example, RNA polymerases can be a T7 RNA polymerase as shown in FIG. 2. RNA polymerases described herein can include a wild type RNA polymerase or a variant RNA polymerase comprising one or more amino acid substitutions that may affect DNA recognition, DNA binding affinity, polymerase activity, or stability of the polymerases. As described herein, RNA polymerases can be provided as fusion proteins comprising an RNA polymerase (e.g., T7 RNA polymerase or the variant thereof) and a heterologous DNA binding protein or domain (e.g., Strep or ZFA) that can recognize and bind a DNA template for microfluidic RNA synthesis, as shown in FIG. 2. In some instances, polymerases may be dried in biomatrix in a cartridge. In this instance, polymerases can be rehydrated before using the cartridge for microfluidic polynucleotide synthesis. In some instances, a cartridge comprising polymerases can be shipped in dry ice, wet ice, or room temperature to preserve polymerases in the cartridge. In some instances, a DNA template may be directly linked to the surface such as beads. In some instances, the surface may comprise a magnetic bead, an agarose bead, fused silica, sol-gel, silica polymer, silica monolith, cellulose, agar, acrylamide, a gold bead, or a gel matrix. In some instances, a solid surface may comprise a gel matrix for encapsulation or entrapment of an RNA polymerase, a DNA template, or a nucleic acid binding protein. In some instances, an RNA polymerase may bind a DNA template linked to a surface.

Figure 3A:
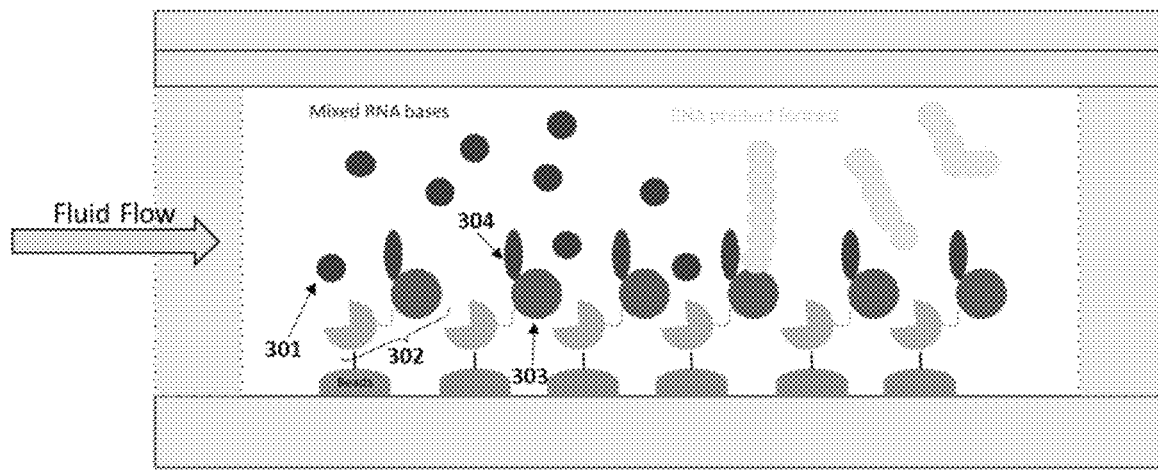
FIG. 3A depicts a schematic of an exemplary microfluidic polynucleotide synthesis.
Figure 3B:
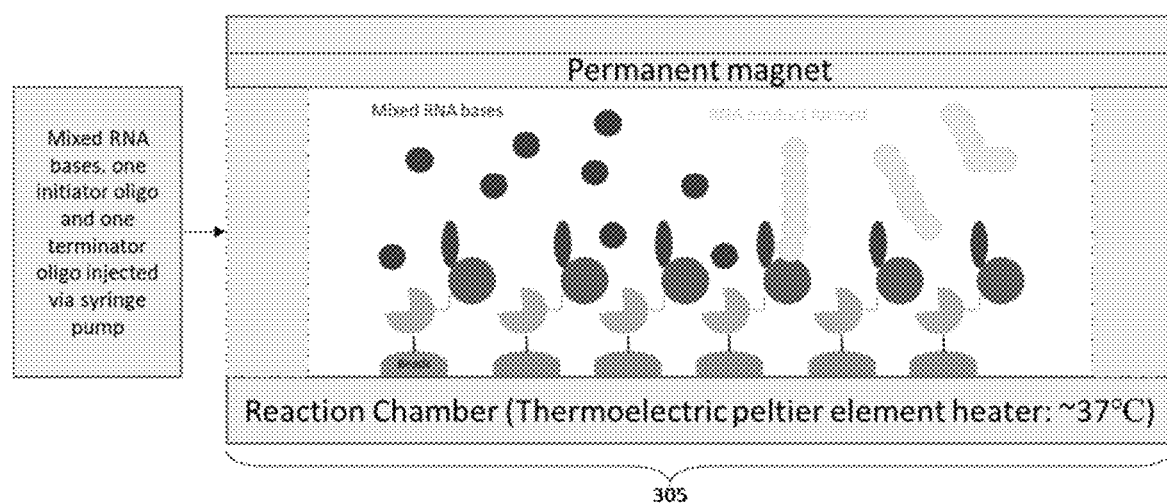
FIG. 3B depicts a schematic of an exemplary microfluidic polynucleotide synthesis.

In Stage 2, transcription reaction reagents 301 are injected to the microfluidic cartridge through a syringe pump and flowed over transcription complex 302 comprising immobilized RNA polymerase 303 and immobilized DNA template 304 in each reaction chamber for microfluidic RNA synthesis (FIG. 3A). Transcription reaction reagents include, but are not limited to, mixed bases, 5' initiator oligos, and 3' terminator oligos. In some instances, modified nucleobases can be used to synthesize RNAs comprising one or more modifications. For example, mixed bases can include natural nucleosides, nucleoside analogs, chemically modified bases, biologically modified bases, intercalated bases, modified sugars, and/or modified phosphate groups. For microfluidic RNA synthesis, a thermoelectric Peltier element heater 305 can be utilized to keep the temperature of the reaction chamber to 37° C. (FIG. 3B). As the transcription reaction reagents are flowed through each reaction chamber in one direction RNAs are produced and removed from the reaction chamber on the order of seconds as controlled by flow rate (FIG. 3B).

In Stage 3, newly synthesized polynucleotides (e.g., RNAs) are extracted and purified using micropillar array and/or Isotachophoresis (ITP) purification process or any known purification methods known to one skilled in the art, and then UV spectroscopically quantified using UV LED and UV detectors (FIG. 1). ITP is a robust electrophoretic separation and preconcentration technique that generates strong electric field gradients and enables selective focusing and separation of charged species based on their electrophoretic mobilities. ITP electrolyte chemistry can be controlled to purify RNAs within the target size range. Alternatively, Capillary electrophoresis (CE), a separation technique in which charged species are separated, based on charge and size, by their different rates of migration in an electric field, can be used for purification. Finished polynucleotide products are preserved and nucleic acid libraries may be synthesized. Synthesized polynucleotides can be also purified using micropillar array. An array of micropillars can capture or trap synthesized polynucleotides while other components of microfluidic polynucleotide synthesis continuously flow through micropillars in washing buffer. Polynucleotides captured or trapped in micropillars can be extracted using elution buffer.

Provided herein are methods of preserving polynucleotides synthesized using microfluidic polynucleotide synthesis methods, compositions, and/or devices described herein. Synthesized polynucleotides may be used immediately after synthesis or stored for later use. In some embodiments, synthesized polynucleotides may be stored in a fridge or a freezer. For example, synthesized polynucleotides may be stored in any temperature known to be suitable for polynucleotide storage. In some embodiments, synthesized polynucleotides may be stored in 4° C., −20° C., or −80° C. In some embodiments, synthesized polynucleotides may be dried in biomatrix using a vacuum pump. In this embodiment, dried polynucleotide products may be rehydrated before use.

In some embodiments, devices for microfluidic polynucleotide synthesis further comprises a piezoelectric vibrator, a turning valve, a Peltier heater, a voltage controller, a syringe pump, a UV LED and sensor, or a vacuum pump. In some embodiments, a piezoelectric vibrator may be used to improve mixing components for microfluidic polynucleotide synthesis such as transcription reaction reagents. In some embodiments, one or more turning valves may be used to select initiator oligos. In some embodiments, a Peltier heater may be used to maintain an optimal temperature for microfluidic polynucleotide synthesis. In some embodiments, a voltage controller may be used to apply power for ITP purification. In some embodiments, a UV LED and sensors can be used to detect and quantify synthesized polynucleotides. In some embodiments, a vacuum pump can be used to dry synthesized polynucleotides.

Provided herein are compositions, methods, devices, and systems for synthesizing RNAs that allow for rapid synthesis of RNAs. Provided herein are methods for synthesizing a plurality of RNAs at a rate of extendsion of at least 50 nucleotides per hour. Also provided herein are compositions, methods, devices, and systems for synthesizing RNAs with preselected sequences. Further provided herein are compositions, methods, devices, and systems for synthesizing RNAs, wherein the synthesizing comprises extending by a single base in an extension reaction. RNAs as described herein can comprise a guide RNA (gRNA), a messenger RNA (mRNA), a small interference RNA (siRNA), a microRNA (miRNA), piwi-interacting RNA (piRNA), RNA aptamers, transfer RNA (tRNA), or antisense oligonucleotide (ASO).

Provided herein are compositions, methods, devices, and systems for synthesizing a plurality of RNAs at a rate of extension of at least 50 nucleotides per hour. For example, the rate of extension is at least 10, 20, 30, 40, 50, 60, 70, 80, 90, 100, 150, 200, 250, 300, 350, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, or 4000 nucleotides per hour. In some embodiments, the rate of extension is at least 10, 20, 30, 40, 50, 60, 70, 80, 90, 100, 150, 200, 250, 300, 350, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, or 4000 nucleotides per minute. In some embodiments, the rate of extension is at least 50 nucleotides per minute. In some embodiments, the rate of extension is at least 3000 nucleotides per minute. In some embodiments, the rate of extension is at least 10, 20, 30, 40, 50, 60, 70, 80, 90, or 100 nucleotides per second. In some embodiments, the rate of extension is at least 50 nucleotides per second.

Provided herein are devices having a surface with a plurality of features for microfluidic polynucleotide synthesis with technical advantages for polynucleotide synthesis such as improved enzyme kinetics and accuracy. The devices provided herein can comprise a pneumatic peristaltic pumping system for programmable fluid manipulation. The peristaltic pumping system may run continuously or deliver smaller amounts of fluid. In some instances, it is desired to minimize the circulating fluid volume. In some instances, the peristaltic pumping system may integrate a micropumping structure into a microfluidic circuit. Provided herein are devices comprising a microfluidic cartridge, a fluid inlet, a fluid outlet, a membrane, a pneumatic microvalve, a pneumatic micropump, or one or more holes for the pneumatic microvalve and the pneumatic micropump. Channels and holes in the devices described herein can be made by laser ablation technique.

Further provided herein are devices comprising a microfluidic cartridge comprising a flow cell or a chamber. Microfluidic cartridges described herein may comprise at least 1, 2, 3, 4, 5, 6, 7, 8, 9, or at least 10 flow cells or chambers. In some instances, the microfluidic cartridge may comprise at least 3 flow cells or chambers. In some instances, the microfluidic cartridge may comprise a reaction chamber, a collection chamber, or an ITP chamber. In some embodiments, the microfluidic cartridge comprises a reaction chamber, a collection chamber, and an ITP chamber. Reaction chambers and collection chambers described herein may utilize a glass wafer or a silicon wafer. In some instances, the reaction chamber and collection chambers may utilize a glass wafer and a silicon wafer. ITP chambers as described herein may utilize a glass wafer. In some instances, the ITP chamber may utilize a glass wafer only due to voltage applied for ITP.

A silicon wafer, as described herein, may have a diameter of 25 to 450 mm. For example, a silicon wafer may have a diameter of 25, 30, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, or 450 mm. In some embodiments, the silicon wafer may have a diameter of 200 mm. A silicon wafer, as described herein, may have a thickness or height of 100 μm to 15 mm. For example, a silicon wafer may have a thickness or height of 100, 150, 200, 250, 300, 350, 400, 450, 500, 550, 600, 650, 700, 750, 800, 850, 900, 950, or 1,000 μm. In some embodiments, the silicon wafer may have a thickness or height of 1, 2, 3, 4, 5, 6, 7, 8, 9, 10, 11, 12, 13, 14, or 15 mm.

A glass wafer, as described herein, may have a diameter of 25 to 450 mm. For example, a glass wafer may have a diameter of 25, 30, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, or 450 mm. In some embodiments, the glass wafer may have a diameter of 200 mm. A glass wafer, as described herein, may have a thickness or height of 0.1 to 1.3 mm. For example, a glass wafer may have a thickness or height of 0.1, 0.2, 0.3, 0.4, 0.5, 0.6, 0.7, 0.8, 0.9, 1.0, 1.1, 1.2, or 1.3 mm.

Silicon wafers or glass wafers, as described herein, may comprise one or more dies. In some instances, each of the one or more dies has a width of 0.5 to 70 mm. For example, each of the one or more dies can have a width of 0.5, 0.6, 0.7, 0.8, 0.9, 1, 5, 10, 15, 20, 25, 30, 35, 40, 45, 50, 55, 60, 65, 70 mm. In some embodiments, each of the one or more dies has a width of 25 mm. In some instances, each of the one or more dies has a height of 0.5 to 70 mm. For example, each of the one or more dies can have a height of 0.5, 0.6, 0.7, 0.8, 0.9, 1, 5, 10, 15, 20, 25, 30, 35, 40, 45, 50, 55, 60, 65, 70 mm. In some embodiments, each of the one or more dies has a height of 37 mm. In some embodiments, each of the one or more dies has a height of 75 mm. In some instances, silicon wafers or glass wafers may have a number of die per wafer (DPW) of 1 to 30. For example, the number of DPW can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 50, 100, 200, 300, 400, 500, 600, 700, 800, 900, or 1000. In some embodiments, the number of DPW is 8. In some embodiments, the number of DPW is 20.

Provided herein are devices comprising a plurality of microchambers, wherein the height or the depth of the chamber is from 100 nm to 100 μm. For example, the height or the depth of the chamber can be 100, 150, 200, 250, 300, 350, 400, 450, 500, 550, 600, 650, 700, 750, 800, 850, 900, 950, or 1,000 nm. For example, the height or the depth of the chamber can be 1, 5, 10, 15, 20, 25, 30, 35, 40, 45, 50, 55, 60, 65, 70, 75, 80, 85, 90, 95, or 100 μm. Further provided herein are devices comprising a plurality of microchambers, wherein the width of the chamber is from 100 nm to 100 μm. For example, the width of the chamber can be 100, 150, 200, 250, 300, 350, 400, 450, 500, 550, 600, 650, 700, 750, 800, 850, 900, 950, or 1,000 nm. For example, the width of the chamber can be 1, 5, 10, 15, 20, 25, 30, 35, 40, 45, 50, 55, 60, 65, 70, 75, 80, 85, 90, 95, or 100 μm.

Provided herein are devices comprising one or more reaction chambers, wherein each reaction chamber comprises one DNA template. DNA templates can be added to reaction chambers after assembly of the microfluidic cartridge. In some instances, microfluidic cartridges can comprise two or more reaction chambers and each of the two or more reaction chambers comprise the same DNA template, thus, producing a plurality of RNAs (e.g., gRNAs, miRNAs, siRNAs, mRNAs, etc.) with the same RNA sequence. In some instances, microfluidic cartridges comprise two or more reaction chambers and each of the two or more reaction chambers comprises a different DNA template, thus producing a plurality of two or more groups of RNAs, wherein each of the two or more groups of RNAs comprise a different RNA sequence. For example, the microfluidic cartridge may comprise three reaction chambers and each of the three reaction chambers comprises a different DNA template, thus producing a plurality of RNAs with three different sequences.

Provided herein are devices for microfluidic polynucleotide synthesis, wherein fluid may flow from the inlet to the outlet of the devices described herein for microfluidic polynucleotide synthesis. As fluid flows from the inlet to the outlet, various rates of flow are used herein for transcription reaction reagents for microfluidic polynucleotide synthesis or purification of synthesized polynucleotides. In some instances, the flow rate is about 0.001 to 1000 nL/second (nL/s). In some instances, the flow rate is about 0.001, 0.005, 0.01, 0.05, 0.1, 0.2, 0.3, 0.4, 0.5, 0.6, 0.7, 0.8, 0.9, 1, 5, 10, 15, 20, 50, 75, 100, 125, 150, 200, 250, 300, 350, 400, 500, 800, or about 1000 nL/second (nL/s). In some instances, the flow rate is at least 0.001, 0.005, 0.01, 0.05, 0.1, 0.2, 0.3, 0.4, 0.5, 0.6, 0.7, 0.8, 0.9, 1, 5, 10, 15, 20, 50, 75, 100, 125, 150, 200, 250, 300, 350, 400, 500, or at least 800 nL/second (nL/s). In some instances, the flow rate is no more than 0.005, 0.01, 0.05, 0.1, 0.2, 0.3, 0.4, 0.5, 0.6, 0.7, 0.8, 0.9, 1, 5, 10, 15, 20, 50, 75, 100, 125, 150, 200, 250, 300, 350, 400, 500, 800, or no more than 1000 nL/second (nL/s). In some instances, the flow rate is about 1, 5, 10, 15, 20, 50, 75, 100, 125, 150, 200, 250, 300, 350, 400, or about 500 μL/second (μL/s). In some instances, the flow rate is at least 1, 5, 10, 15, 20, 50, 75, 100, 125, 150, 200, 250, 300, 350, 400, or at least 500 μL/s. In some instances, the flow rate is no more than 5, 10, 15, 20, 50, 75, 100, 125, 150, 200, 250, 300, 350, 400, or no more than 500 μL/s. In some instances, the flow rate is about 1 to 500 μL/s, about 5 to 500 μL/s, about 10 to 400 μL/s, about 20 to 300 μL/s, about 50 to 500 μL/s, about 50 to 400 μL/s, about 50 to 300 μL/s, about 75 to 300 μL/s, about 100 to 400 μL/s, about 200 to 500 μL/s, or about 40 to 350 μL/s. In some instances, the flow rate is about 40 to 350 μL/s. In some instances, the flow rate is about 75 to 250 μL/s. In some instances, the flow rate is about 50 to 400 μL/s.

Provided herein are devices for microfluidic polynucleotide synthesis, wherein devices may comprise channels having a width, height, or diameter of 1 μm to 1 cm. For example, a channel on microfluidic polynucleotide synthesis devices may have a width, height, or diameter of at least 1, 5, 10, 15, 20, 50, 75, 100, 125, 150, 200, 250, 300, 350, 400, 450, 500, 550, 600, 650, 700, 750, 800, 850, 900 or at least 950 μm. For example, a channel on microfluidic polynucleotide synthesis devices may have a width, height, or diameter of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 mm. In some embodiments, a channel on microfluidic polynucleotide synthesis devices may have a total volume of about 1 μL to 100 mL. For example, a channel on microfluidic polynucleotide synthesis devices may have a total volume of at least about 1, 5, 10, 15, 20, 50, 75, 100, 125, 150, 200, 250, 300, 350, 400, 450, 500, 550, 600, 650, 700, 750, 800, 850, 900, or at least about 950 μL. In some embodiments, a channel on microfluidic polynucleotide synthesis devices may have a total volume of 1, 2, 3, 4, 5, 6, 7, 8, 9, 10, 15, 20, 25, 30, 35, 40, 45, 50, 55, 60, 65, 70, 75, 80, 85, 90, 95 or 100 mL.

Provided herein are devices for microfluidic polynucleotide synthesis, wherein synthesized polynucleotides may be purified using ITP purification process. Voltage used for ITP purification process may depend on the length of a column or channel used for ITP purification process. For example, voltage can be from 10 to 500 V. for example, voltage can be 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 V.

Provided herein are devices for microfluidic polynucleotide synthesis, wherein synthesized polynucleotides may be purified using an array of micropillars. A micropillar can be of from 0.1 to 10.0 μm in diameter. For example, a micropillar can be of 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 4.0, 4.5, 5.0, 5.5, 6.0, 7.0, 8.0, 9.0, 9.5, or 10.0 μm in diameter. In some embodiments, the height of a micropillar can be from 10 to 50 μm. For example, the height of a micropillar can be 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 μm. In some embodiments, an array of micropillars may comprise micropillars spaced from 100 to 1500 nm apart. For example, micropillars may be spaced 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, or 1500 nm apart.

Provided herein are devices for microfluidic polynucleotide synthesis wherein surface chemistry and fluid dynamics for microfluidic polynucleotide synthesis can increase enzyme kinetics, enhance purity, allow RNA modifications including 5' end, 3' end, and internal chemical modifications. Provided herein are devices for microfluidic polynucleotide synthesis allowing for integrated RNA purification and quality control, which can reduce production cost.

DNA Template

Provided herein are methods, compositions, devices, and systems for producing of polynucleotides using DNA templates. The DNA templates described herein can be double-stranded DNA (dsDNA), partially double-stranded DNA, or single-stranded DNA (ssDNA). DNA templates can include, but are not limited to, linearized plasmid constructs engineered by cloning, e.g., plasmid vectors, PCR products, oligonucleotides, e.g., two complementary oligonucleotides annealed together, or complementary DNA (cDNA) templates generated by first- and second-strand synthesis from an RNA precursor. DNA templates may comprise a promoter region where RNA polymerase binds and initiates RNA synthesis. For example, T7 RNA polymerase requires a dsDNA promoter to initiate transcription. ssDNA templates are more desirable for transcription than dsDNA templates as ssDNA requires less energy because unwinding process of double-stranded template is not necessary, is less likely to dissociate from the template, allowing for faster initiation, and elongation does not require a dsDNA template. ssDNA templates described herein can comprise a secondary structure to create a partially double-stranded promoter region for recognition by RNA polymerases. Examples of the secondary structure include, but are not limited to, a stem, a pseudoknot, a hairpin loop, an internal loop, a multi-branch loop, and a bulge loop. In some embodiments, a promoter region described herein may comprise an essential promoter region and/or a non-essential promoter region. An exemplary ssDNA template is shown in FIG. 4 and comprises, in 5' to 3' direction, a template sequence for RNA transcription 401, a DNA melting region 402, the promoter sequence 403, a loop 404 connecting 403 and 405, and the reverse-complement counterpart of the promoter sequence 405. As 405 hybridizes to 403, the ssDNA template forms a secondary structure, for example, a hairpin, resulting in a partially double-stranded region that can be recognized by an RNA polymerase. In some embodiments, the secondary structure comprises a hairpin. In some embodiments, an exemplary sequence of the hairpin structure can comprise a sequence comprising SEQ ID NO: 7.

Provided herein are DNA templates for microfluidic polynucleotide synthesis, as described herein, comprising a promoter sequence. DNA templates, described herein, may comprise a promoter sequence corresponding to an RNA polymerase selected for RNA synthesis. For example, DNA templates may comprise a phage promoter sequence, for example, T3 promoter sequence, a T7 promoter sequence, a KP34 promoter sequence, a N4 promoter sequence, or a SP6 promoter sequence depending on the choice of RNA polymerase for RNA synthesis. Provided herein are DNA templates comprising a T7 promoter sequence. DNA templates provided herein may comprise an essential T7 promoter and/or an non-essential T7 promoter. In some embodiments, the T7 promoter sequence comprises an essential T7 promoter sequence. In some embodiments, the T7 promoter sequence comprises a non-essential T7 promoter sequence. In some embodiments, the T7 promoter sequence comprises an essential T7 promoter sequence and a non-essential T7 promoter sequence. In some embodiments, an essential T7 promoter sequence comprises a sequence comprising SEQ ID NO: 15. In some embodiments, a non-essential T7 promoter sequence comprises a sequence comprising SEQ ID NO: 16. Further provided herein are DNA templates comprising a truncated promoter sequence. In some instances, DNA templates described herein can comprise a truncated T7 promoter sequence. In one example, a truncation may be on the 5' end of the T7 promoter sequence. In another example, a truncation may be on the 3' end of the T7 promoter sequence. In some embodiments, the T7 promoter sequence comprises a sequence comprising SEQ ID NO: 3. In some embodiments, the T7 promoter sequence comprises a sequence comprising SEQ ID NO: 4. In some embodiments, the T7 promoter sequence comprises a sequence comprising SEQ ID NO: 5. In some embodiments, the T7 promoter sequence comprises a sequence comprising SEQ ID NO: 6. In some embodiments, a truncation may be in a non-essential T7 promoter sequence.

Provided herein are DNA templates for microfluidic polynucleotide synthesis further comprising a DNA binding target sequence that is recognized by a DNA binding protein or a DNA binding domain. In some instances, the DNA binding target sequence that is recognized by a DNA binding protein or a DNA binding domain may comprise a zinc finger array (ZFA) binding sequence. In some embodiments, DNA templates may comprise one or more copies of the ZFA binding sequence. For example, DNA templates may comprise 1, 2, 3, 4, 5, 6, 7, 8, 9, or 10 or more copies of the ZFA binding sequence. DNA templates, as described herein, may comprise the one or more copies of the ZFA binding sequence, wherein the one or more copies of the ZFA binding sequence can be arranged in tandem with a nucleotide linker or insert between each of the one or more copies of the ZFA binding sequence (e.g., 5'-ZFA-nucleotide linker-ZFA-nucleotide linker- . . . -3'). In some instances, the nucleotide linker or insert may comprise 2-30 nucleotides in length. For example, the nucleotide linker or insert may comprise 2, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides in length. In some embodiments, the nucleotide linker or insert comprises 8, 9, or 10 nucleotides in length. Provided herein, are DNA templates comprising one or more copies of the ZFA binding sequence upstream of or 5' to the promoter sequence (e.g., 5'-(ZFA-nucleotide linker)$_n$-promoter sequence –3,' wherein n is an integer from 1 to 10). In some embodiments, the promoter sequence is a truncated promoter sequence.

Provided herein are DNA templates for programmable RNA synthesis, comprising one or more DNA binding target sequences (e.g., one or more copies of the ZFA binding sequence) and a truncated promoter sequence. DNA templates, described herein, can be used in a programmable RNA synthesis system that utilizes a fusion protein comprising a DNA binding domain (e.g., ZFA) and an RNA polymerase (e.g., T7 RNA polymerase). In this system, RNA synthesis can be programmed by manipulating the copies of the DNA binding target sequences such as ZFA binding sequence to adjust the binding affinity of the fusion protein to DNA templates as the binding affinity is an important factor for RNA transcription.

DNA templates, as described herein, can be of different lengths. For example, DNA templates may comprise at least 40, at least 50, at least 60, at least 70, at least 80, at least 90, at least 100, at least 150, at least 200, or at least 300 nucleotides in length. In some instances, the DNA template comprises at most 70, at most 80, at most 90, at most 100, at most 120, at most 140, at most 160, at most 180, or at most 200 nucleotides in length. In some instances, the DNA template comprises about 40, about 50, about 60, about 70, about 80, about 90, about 100, about 120, about 140, about 160, about 180, about 200, about 250, or about 300 nucleotides in length. In some instances, the DNA template comprises at least 60 nucleotides in length. In some embodiments, the DNA template comprises at least 120 nucleotides in length. In some embodiments, the DNA template comprises at most 80 nucleotides in length.

DNA templates as described herein may comprise a sequence to synthesize a coding RNA or a non-coding RNA. Non-limiting examples of coding RNA include mRNAs and non-limiting examples of non-coding RNAs include gRNAs, miRNAs, siRNAs, shRNAs, and ASOs. For example, the DNA templates may comprise a sequence to synthesize gRNAs that can be used to target certain genes involved in a disease or a condition for CRISPR-Cas9 mediated gene editing. In some instances, target genes can include genes involved in a cancer, for example, genes involved in acute lymphocytic cancer, acute myeloid leukemia, alveolar rhabdomyosarcoma, bladder cancer, bone cancer, brain cancer, breast cancer, cancer of the anus, anal canal, rectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, fibrosarcoma, gastrointestinal carcinoid tumor, Hodgkin lymphoma, hypopharynx cancer, kidney cancer, larynx cancer, leukemia, liquid tumors, liver cancer, lung cancer, lymphoma, malignant mesothelioma, mastocytoma, melanoma, multiple myeloma, nasopharynx cancer, non-Hodgkin lymphoma, ovarian cancer, pancreatic cancer, peritoneum, omentum, and mesentery cancer, pharynx cancer, prostate cancer, rectal cancer, renal cancer, skin cancer, small intestine cancer, soft tissue cancer, solid tumors, stomach cancer, testicular cancer, thyroid cancer, ureter cancer, and/or urinary bladder cancer. In some instances, target genes can include MAGE-1, MAGE-2, MAGE-3, CEA, Tyrosinase, midkine, BAGE, CASP-8, β-catenin, CA-125, CDK-1, ESO-1, gp75, gpl00, MART-1, MUC-1, MUM-1, p53, PAP, PSA, PSMA, ras, trp-1, HER-2, TRP-1, TRP-2, IL13Ralpha, IL13Ralpha2, AIM-2, AIM-3, NY-ESO-1, C9orfl12, SART1, SART2, SART3, BRAP, RTN4, GLEA2, T KS2, KIAA0376, ING4, HSPH1, C13orf24, REIC, RBPSUH, C6orfl53, KTR, NSEP1, U2AF1L, CY L2, TPR, SOX2, GOLGA, BMI1, COX-2, EGFRvIII, EZH2, LICAM, Livin, MRP-3, Nestin, OLIG2, ART1, ART4, B-cyclin, Gli1, Cav-1, cathepsin B, CD74, E-cadherin, EphA2/Eck, Fra-l/Fosll, GAGE-1, Ganglioside/GD2, GnT-V, β1,6-N, Ki67, Ku70/80, PROX1, PSCA, SOX10, SOX11, Survivin, UPAR, Mesothelin, WT-1, RET, ERBB2 or HER2, PDGF-Rβ, SRC, PRAD1/cyclin D1, C-Myc, BCL2, ABL, MDM2, p110α, B-RAF, IDH1, IDH2, JAK2, KIT, MET, FLT-3, VEGF, VEGFR, SKY, p53, RB, BCL2, SWI/SNF, RAP1A, DCC, K-REV, WT1, TBR-11, INK4A/ARF, SMAD2, SMAD3, SMAD4/DPC4, E-CADHERIN, APC, VHL, PTEN/MMAC1, NF1, NF2, BRCA1, BRCA2, MSH2, MLH1, PMS1, PMS2, REIC, SDHB, SDHD, and/or GP43/Merlin. In some instances, target genes can include genes involved in an immune disorder, for example, PTPN22, TRAF1-C5, PADI4, STAT4, TNF, IL-1, IL-6, IL-4, IL-5, OPN, PRF1, IFIH1, TRAF3IP2, IL12A, IL12RB2, AIRE, Fas, FasL, caspase 10, caspase 8, PRKCD, NRAS, CTLA-4, FOXP3, LRBA, HLA-DQ8, INS, IL2RA, SH2B3, ERBB3, PTPN2, CLEC16A, IL18RAP, CTSH, CD226, IL2RA, PRKCQ, IL2, BACH2, UBASH3A, RGS1, IL17RA, CIQTNF6, TNFAIP3, TYK2, and/or TAGAP. In some instances, target genes can include genes that need to be knocked down, knocked out, modified, or edited. In some instances, target genes can include genes that need to be transcriptionally regulated, for example, upregulated or downregulated.

In some embodiments, the amount of RNA transcribed using DNA templates described herein may be increased compared to the amount of RNA transcribed using traditional DNA templates i.e., DNA templates without features described herein. For example, the amount of RNA transcribed using DNA templates described herein may be increased at least by 1.1 fold, 1.2 fold, 1.3 fold, 1.4 fold, 1.5 fold, 1.6 fold, 1.7 fold, 1.8 fold, 1.9 fold, 2.0 fold, 2.1 fold, 2.2 fold, 2.3 fold, 2.4 fold, 2.5 fold, 2.6 fold, 2.7 fold, 2.8 fold, 2.9 fold, 3.0 fold, 3.1 fold, 3.2 fold, 3.3 fold, 3.4 fold, 3.5 fold, 4.0 fold, 4.5 fold, 5.0 fold, 5.5 fold, 6.0 fold, 7.0 fold, 8.0 fold, 9.0 fold, 9.5 fold, 10.0 fold, 10.5 fold, 11.0 fold, 11.5 fold, 12.0 fold, 12.5 fold, 13.0 fold, 14.5 fold, 15.0 fold, 15.5 fold, 16.0 fold, 16.5 fold, 17.0 fold, 17.5 fold, 18.0 fold, 18.5 fold, 19.0 fold, 19.5 fold, 20 fold, 21 fold, 22 fold, 23 fold, 24 fold, 25 fold, 26 fold, 27 fold, 28 fold, 29 fold, 30 fold, 31 fold, 32 fold, 33 fold, 34 fold, 35 fold, 36 fold, 37 fold, 38 fold, 39 fold, 40 fold, 41 fold, 42 fold, 43 fold, 44 fold, 45 fold, 46 fold, 47 fold, 48 fold, 49 fold, 50 fold, 60 fold, 70 fold, 80 fold, 90 fold, 100 fold, 110 fold, 120 fold, 130 fold, 140 fold, 150 fold, 160 fold, 170 fold, 180 fold, 190 fold, 200 fold, 210 fold, 220 fold, 230 fold, 240 fold, 250 fold, 260 fold, 270 fold, 280 fold, 290 fold, 300 fold, 310 fold, 320 fold, 330 fold, 340 fold, 350 fold, 360 fold, 370 fold, 380 fold, 390 fold, 400 fold, 410 fold, 420 fold, 430 fold, 440 fold, 450 fold, 460 fold, 470 fold, 480 fold, 490 fold, 500 fold, 610 fold, 620 fold, 630 fold, 640 fold, 650 fold, 660 fold, 670 fold, 680 fold, 690 fold, 700 fold, 710 fold, 720 fold, 730 fold, 740 fold, 750 fold, 760 fold, 770 fold, 780 fold, 790 fold, 800 fold, 810 fold, 820 fold, 830 fold, 840 fold, 850 fold, 860 fold, 870 fold, 880 fold, 890 fold, 900 fold, 910 fold, 920 fold, 930 fold, 940 fold, 950 fold, 960 fold, 970 fold, 980 fold, 990 fold, 1000 fold, 1100 fold, 1200 fold, 1300 fold, 1400 fold, 1500 fold, 1600 fold, 1700 fold, 1800 fold, 1900 fold, 2000 fold, 2100 fold, 2200 fold, 2300 fold, 2400 fold, 2500 fold, 2600 fold, 2700 fold, 2800 fold, 2900 fold, 3000 fold, 3100 fold, 3200 fold, 3300 fold, 3400 fold, 3500 fold, 3600 fold, 3700 fold, 3800 fold, 3900 fold, 4000 fold, 4100 fold, 4200 fold, 4300 fold, 4400 fold, 4500 fold, 4600 fold, 4700 fold, 4800 fold, 4900 fold, 5000 fold, 5100 fold, 5200 fold, 5300 fold, 5400 fold, 5500 fold, 5600 fold, 5700 fold, 5800 fold, 5900 fold, 6000 fold, 6100 fold, 6200 fold, 6300 fold, 6400 fold, 6500 fold, 6600 fold, 6700 fold, 6800 fold, 6900 fold, 7000 fold, 7100 fold, 7200 fold, 7300 fold, 7400 fold, 7500 fold, 7600 fold, 7700 fold, 7800 fold, 7900 fold, 8000 fold, 8100 fold, 8200 fold, 8300 fold, 8400 fold, 8500 fold, 8600 fold, 8700 fold, 8800 fold, 8900 fold, 9000 fold, 9100 fold, 9200 fold, 9300 fold, 9400 fold, 9500 fold, 9600 fold, 9700 fold, 9800 fold, 9900 fold, or at least by 10000 fold, compared to the amount of RNA transcribed using traditional DNA templates i.e., DNA templates without features described herein.

In some embodiments, the amount of DNA template required for RNA synthesis using DNA templates described herein may be lower than the amount of DNA template required for RNA synthesis using traditional DNA templates i.e., DNA templates without features described herein. For example, the amount of DNA template required for RNA synthesis using DNA templates described herein may be at least 1.1 fold, 1.2 fold, 1.3 fold, 1.4 fold, 1.5 fold, 1.6 fold, 1.7 fold, 1.8 fold, 1.9 fold, 2.0 fold, 2.1 fold, 2.2 fold, 2.3 fold, 2.4 fold, 2.5 fold, 2.6 fold, 2.7 fold, 2.8 fold, 2.9 fold, 3.0 fold, 3.1 fold, 3.2 fold, 3.3 fold, 3.4 fold, 3.5 fold, 4.0 fold, 4.5 fold, 5.0 fold, 5.5 fold, 6.0 fold, 7.0 fold, 8.0 fold, 9.0 fold, 9.5 fold, or at least 10.0 fold lower than the amount of DNA template required for RNA synthesis using traditional DNA templates i.e., DNA templates without features described herein.

In some embodiments, the amount of nucleoside triphosphates (NTPs) required for RNA synthesis using DNA templates described herein may be lower than the amount of NTPs required for RNA synthesis using traditional DNA templates i.e., DNA templates without features described herein. For example, the amount of nucleoside triphosphates (NTPs) required for RNA synthesis using DNA templates described herein may be at least 1.1 fold, 1.2 fold, 1.3 fold, 1.4 fold, 1.5 fold, 1.6 fold, 1.7 fold, 1.8 fold, 1.9 fold, 2.0 fold, 2.1 fold, 2.2 fold, 2.3 fold, 2.4 fold, 2.5 fold, 2.6 fold, 2.7 fold, 2.8 fold, 2.9 fold, 3.0 fold, 3.1 fold, 3.2 fold, 3.3 fold, 3.4 fold, 3.5 fold, 4.0 fold, 4.5 fold, 5.0 fold, 5.5 fold, 6.0 fold, 7.0 fold, 8.0 fold, 9.0 fold, 9.5 fold, or at least 10.0 fold lower than the amount of NTPs required for RNA synthesis using traditional DNA templates i.e., DNA templates without features described herein.

RNA Polymerase

Provided herein are RNA polymerases for microfluidic RNA synthesis. For example, an RNA polymerase can comprise a phage RNA polymerase, a bacterial RNA polymerase, or a eukaryote RNA polymerase. In some instances, the bacterial RNA polymerase can comprise an RNA polymerase from any bacterial species, including, but not limited to, E. coli. In some instances, the eukaryote RNA polymerase may comprise an RNA polymerase I, an RNA polymerase II, an RNA polymerase III, an RNA polymerase IV, or an RNA polymerase V from any eukaryotes. Non-limiting examples of the phage RNA polymerase include T3 RNA polymerase, a T7 RNA polymerase, a KP34 RNA polymerase, a N4 RNA polymerase, and a SP6 RNA polymerase. In some embodiments, the RNA polymerase used for microfluidic RNA synthesis described herein is a T7 RNA polymerase. In some embodiments, the T7 RNA polymerase comprises a sequence comprising SEQ ID NO: 1.

Further provided herein are RNA polymerases comprising one or more variations or substitutions in amino acid sequence, for example, a variation related to stability, DNA recognition, DNA binding affinity, and/or enzyme activity such as RNA polymerase activity. In some instances, the one or more variations may enhance the stability of the variant RNA polymerase during a transcription initiation and/or elongation process compared to an RNA polymerase without the one or more variations. In some instances, the one or more variations may enhance the DNA recognition ability of the RNA polymerase compared to an RNA polymerase without the one or more variations. In some instances, the one or more variations may enhance the DNA binding affinity of the RNA polymerase compared to an RNA polymerase without the one or more variations. In some instances, the one or more variations may reduce the DNA binding affinity of the RNA polymerase compared to an RNA polymerase without the one or more variations. In some instances, the one or more variations may enhance the RNA polymerase activity compared to an RNA polymerase without the one or more variations.

Provided herein are T7 RNA polymerase variants for microfluidic RNA synthesis. Non-limiting examples of the variations or amino acid substitutions in the T7 RNA polymerase include I4M, I119V, N165S, K172L, G175R, E222K, G225S, Q239K, Q239R, Q239L, A255T, P266L, K333N, D366N, F400L, V426L, V426I, V426F, S430P, N433T, G542V, V574A, E593G, V625L, S633V, S633M, S633P, Y639F, Y639L, Y639V, E643K, V650L, T654L, S661G, G675R, V685A, A702V, R756C, Q758K, Q758R, V783I, V795I, H772R, N748X, R756M, Q758X, E775K, E775V, H784A, H784G, H784S, F849I, and F880Y, wherein the position is determined by alignment with SEQ ID NO: 1 and wherein X is any amino acid different from the wild type amino acid. Provided herein are T7 RNA polymerase variants for microfluidic RNA synthesis, wherein T7 RNA polymerase variants comprise at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 40, or at least 41 amino acid variations or amino acid substitutions. For example, T7 RNA polymerase variants described herein may comprise at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 40, or at least 41 variations or amino acid substitutions in the DNA recognition or binding domain (e.g., AT-recognition loop). For example, T7 RNA polymerase variants described herein may comprise at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 40, or at least 41 variations or amino acid substitutions in the RNA polymerase domain (e.g., thumb sub-domain, palm domain, or finger sub-domain). For example, T7 RNA polymerase variants described herein may comprise at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 40, or at least 41 variations or amino acid substitutions in the specificity loop.

Provided herein are T7 RNA polymerase variants comprising at least one, at least two, at least three, or at least four or more of variations described herein, e.g., K172L, P266L, H772R, N748X, R756M, Q758X, and E775V, wherein the position is determined by alignment with SEQ ID NO: 1 and wherein X is any amino acid different from the wild type amino acid. Also provided herein are T7 RNA polymerase variants comprising at least one variation selected from the group consisting of K172L, P266L, H772R, N748X, R756M, Q758X, and E775V, wherein the position is determined by alignment with SEQ ID NO: 1 and wherein X is any amino acid different from the wild type amino acid. Further provided herein are T7 RNA polymerase variants comprising at least four variations selected from the group consisting of K172L, P266L, H772R, N748X, R756M, Q758X, and E775V, wherein the position is determined by alignment with SEQ ID NO: 1 and wherein X is any amino acid different from the wild type amino acid. In some instances, the variant T7 RNA polymerase or a functional fragment thereof comprises a sequence that has at least 90% identity to SEQ ID NO: 1. In some embodiments, the variant T7 RNA polymerase comprising at least one or at least four variations described herein may exhibit increased stability during a transcription initiation and/or elongation process compared to a T7 RNA polymerase without the at least one variation, for example, a T7 RNA polymerase comprising a sequence according to SEQ ID NO: 1. In some embodiments, the variant T7 RNA polymerase comprising at least one or at least four variations described herein may exhibit reduced DNA binding affinity, e.g., reduced binding affinity to a T7 promoter sequence, compared to a T7 RNA polymerase without the at least one variation, for example, a T7 RNA polymerase comprising a sequence according to SEQ ID NO: 1.

In some embodiments, the amount of RNA transcribed using RNA polymerases described herein (e.g., modified RNA polymerases) may be increased compared to the amount of RNA transcribed using traditional RNA polymerases i.e., RNA polymerases without features or modifications described herein. In some embodiments, the amount of RNA transcribed using RNA polymerases described herein (e.g., modified RNA polymerases) may be increased at least by 1.1 fold, 1.2 fold, 1.3 fold, 1.4 fold, 1.5 fold, 1.6 fold, 1.7 fold, 1.8 fold, 1.9 fold, 2.0 fold, 2.1 fold, 2.2 fold, 2.3 fold, 2.4 fold, 2.5 fold, 2.6 fold, 2.7 fold, 2.8 fold, 2.9 fold, 3.0 fold, 3.1 fold, 3.2 fold, 3.3 fold, 3.4 fold, 3.5 fold, 4.0 fold, 4.5 fold, 5.0 fold, 5.5 fold, 6.0 fold, 7.0 fold, 8.0 fold, 9.0 fold, 9.5 fold, 10.0 fold, 10.5 fold, 11.0 fold, 11.5 fold, 12.0 fold, 12.5 fold, 13.0 fold, 14.5 fold, 15.0 fold, 15.5 fold, 16.0 fold, 16.5 fold, 17.0 fold, 17.5 fold, 18.0 fold, 18.5 fold, 19.0 fold, 19.5 fold, 20 fold, 21 fold, 22 fold, 23 fold, 24 fold, 25 fold, 26 fold, 27 fold, 28 fold, 29 fold, 30 fold, 31 fold, 32 fold, 33 fold, 34 fold, 35 fold, 36 fold, 37 fold, 38 fold, 39 fold, 40 fold, 41 fold, 42 fold, 43 fold, 44 fold, 45 fold, 46 fold, 47 fold, 48 fold, 49 fold, 50 fold, 60 fold, 70 fold, 80 fold, 90 fold, 100 fold, 110 fold, 120 fold, 130 fold, 140 fold, 150 fold, 160 fold, 170 fold, 180 fold, 190 fold, 200 fold, 210 fold, 220 fold, 230 fold, 240 fold, 250 fold, 260 fold, 270 fold, 280 fold, 290 fold, 300 fold, 310 fold, 320 fold, 330 fold, 340 fold, 350 fold, 360 fold, 370 fold, 380 fold, 390 fold, 400 fold, 410 fold, 420 fold, 430 fold, 440 fold, 450 fold, 460 fold, 470 fold, 480 fold, 490 fold, 500 fold, 610 fold, 620 fold, 630 fold, 640 fold, 650 fold, 660 fold, 670 fold, 680 fold, 690 fold, 700 fold, 710 fold, 720 fold, 730 fold, 740 fold, 750 fold, 760 fold, 770 fold, 780 fold, 790 fold, 800 fold, 810 fold, 820 fold, 830 fold, 840 fold, 850 fold, 860 fold, 870 fold, 880 fold, 890 fold, 900 fold, 910 fold, 920 fold, 930 fold, 940 fold, 950 fold, 960 fold, 970 fold, 980 fold, 990 fold, 1000 fold, 1100 fold, 1200 fold, 1300 fold, 1400 fold, 1500 fold, 1600 fold, 1700 fold, 1800 fold, 1900 fold, 2000 fold, 2100 fold, 2200 fold, 2300 fold, 2400 fold, 2500 fold, 2600 fold, 2700 fold, 2800 fold, 2900 fold, 3000 fold, 3100 fold, 3200 fold, 3300 fold, 3400 fold, 3500 fold, 3600 fold, 3700 fold, 3800 fold, 3900 fold, 4000 fold, 4100 fold, 4200 fold, 4300 fold, 4400 fold, 4500 fold, 4600 fold, 4700 fold, 4800 fold, 4900 fold, 5000 fold, 5100 fold, 5200 fold, 5300 fold, 5400 fold, 5500 fold, 5600 fold, 5700 fold, 5800 fold, 5900 fold, 6000 fold, 6100 fold, 6200 fold, 6300 fold, 6400 fold, 6500 fold, 6600 fold, 6700 fold, 6800 fold, 6900 fold, 7000 fold, 7100 fold, 7200 fold, 7300 fold, 7400 fold, 7500 fold, 7600 fold, 7700 fold, 7800 fold, 7900 fold, 8000 fold, 8100 fold, 8200 fold, 8300 fold, 8400 fold, 8500 fold, 8600 fold, 8700 fold, 8800 fold, 8900 fold, 9000 fold, 9100 fold, 9200 fold, 9300 fold, 9400 fold, 9500 fold, 9600 fold, 9700 fold, 9800 fold, 9900 fold, or at least by 10000 fold, compared to the amount of RNA transcribed using traditional RNA polymerases i.e., RNA polymerases without features or modifications described herein.

In some embodiments, the amount of DNA template required for RNA synthesis using RNA polymerases described herein (e.g., modified RNA polymerases) may be lower than the amount of DNA template required for RNA synthesis using traditional RNA polymerases i.e., RNA polymerases without features or modifications described herein. In some embodiments, the amount of DNA template required for RNA synthesis using RNA polymerases described herein (e.g., modified RNA polymerases) described herein may be at least 1.1 fold, 1.2 fold, 1.3 fold, 1.4 fold, 1.5 fold, 1.6 fold, 1.7 fold, 1.8 fold, 1.9 fold, 2.0 fold, 2.1 fold, 2.2 fold, 2.3 fold, 2.4 fold, 2.5 fold, 2.6 fold, 2.7 fold, 2.8 fold, 2.9 fold, 3.0 fold, 3.1 fold, 3.2 fold, 3.3 fold, 3.4 fold, 3.5 fold, 4.0 fold, 4.5 fold, 5.0 fold, 5.5 fold, 6.0 fold, 7.0 fold, 8.0 fold, 9.0 fold, 9.5 fold, or at least 10.0 fold lower than the amount of DNA template required for RNA synthesis using traditional RNA polymerases i.e., RNA polymerases without features or modifications described herein.

In some embodiments, the amount of nucleoside triphosphates (NTPs) required for RNA synthesis using RNA polymerases described herein (e.g., modified RNA polymerases) may be lower than the amount of NTPs required for RNA synthesis using traditional RNA polymerases i.e., RNA polymerases without features or modifications described herein. For example, the amount of nucleoside triphosphates (NTPs) required for RNA synthesis using RNA polymerases described herein (e.g., modified RNA polymerases) may be at least 1.1 fold, 1.2 fold, 1.3 fold, 1.4 fold, 1.5 fold, 1.6 fold, 1.7 fold, 1.8 fold, 1.9 fold, 2.0 fold, 2.1 fold, 2.2 fold, 2.3 fold, 2.4 fold, 2.5 fold, 2.6 fold, 2.7 fold, 2.8 fold, 2.9 fold, 3.0 fold, 3.1 fold, 3.2 fold, 3.3 fold, 3.4 fold, 3.5 fold, 4.0 fold, 4.5 fold, 5.0 fold, 5.5 fold, 6.0 fold, 7.0 fold, 8.0 fold, 9.0 fold, 9.5 fold, or at least 10.0 fold lower than the amount of NTPs required for RNA synthesis using traditional RNA polymerases i.e., RNA polymerases without features or modifications described herein.

Fusion Protein

Provide herein are fusion proteins comprising an RNA polymerase or a functional fragment thereof and a DNA binding domain for use in RNA synthesis described herein, wherein the RNA polymerase or a functional fragment thereof and the DNA binding domain are heterologous. Fusion proteins or fusion polypeptides, as used herein, can comprise the RNA polymerase described herein, for example, the T7 RNA polymerase or the variant thereof, and a heterologous DNA binding domain that can recognize and bind the DNA template for RNA synthesis.

Exemplary DNA binding domains include, but are not limited to, a zinc-finger domain, a leucine zipper, a helix-turn-helix (HTH) motif, a helix-loop-helix (HLH) motif, a winged helix (WH), a winged HTH (WHTH) motif, a high mobility group (HMG)-box, a White-Opaque Regulator 3 (Wor3) domain, an oligonucleotide/oligosaccharide-binding (OB)-fold domain, an immunoglobulin fold, a B3 domain, a Transcription Activator-Like Effector (TALE), a TALE-like protein, and a Clustered Regularly Interspaced Short Palindromic Repeats (CRISPR)-associated (Cas) protein. In some instances, the DNA binding domain comprises an avidin. Non-limiting examples of an avidin include streptavidin, rhizavidin, and neutravidin, such as Extravidin, NeutrAvidin, NeutraLite. In some instances, the DNA binding domain used herein may not comprise a mutation or a variation. In some instances, the DNA binding domain may comprise a mutation or a variation. In some instances, the DNA binding domain comprises a DNA methyltransferase. In some instances, the DNA methyltransferase is a HaeIII Methyltransferase (HaeIIIM) from *Haemophilus aegyptius*. In some embodiments, a DNA methyltransferase may covalently bind DNA, e.g., the DNA template, in the presence of a modified base including, but not limited to, 5-bromo-cytidine, 5-iodo-cytidine, 5-fluoro-cytidine, 5-bromo-deoxyuracil, 5-iodo-deoxyuracil, or 5-fluoro-deoxyuracil. In some instances, the DNA binding domain is a zinc-finger domain. In some embodiments, the zinc-finger domain comprises a zinc finger array (ZFA). In some embodiments, the DNA binding domain comprises a sequence comprising SEQ ID NO: 8. In some instances, the DNA binding domain is a leucine zipper. In some embodiments, the DNA binding domain is a Streptavidin. In some embodiments, the DNA binding domain is a monomeric streptavidin. In some embodiments, the DNA binding domain is rhizavidin. In some embodiments, the DNA binding domain comprises a sequence comprising SEQ ID NO: 9.

Provided herein are RNA polymerases or the functional fragments thereof linked to a DNA binding domain. The general architecture of an exemplary RNA polymerase fusion protein with a DNA binding domain can comprise the following structure: $NH_2$-[DNA binding domain]-[linker]-[RNA polymerase]-COOH, wherein $NH_2$ is the N-terminus of the fusion protein and COOH is the C-terminus of the fusion protein. In some instances, the RNA polymerase or the functional fragment thereof is covalently attached to the DNA binding domain. For example, the RNA polymerase or the functional fragment thereof may be linked to the DNA binding domain via a linker. Non-limiting examples of the linker include a peptide linker, a non-peptide linker, a nucleotide linker, a chemical linker, and a flexible linker. In some embodiments, the linker is a peptide linker. In some embodiments, the linker is a non-peptide linker. In some embodiments, the linker comprises at least 7, at least 8, at least 9, at least 10, at least 11, at least 12, at least 13, at least 14, at least 15, at least 20, at least 25, at least 30, at least 35, or at least 40 amino acid residues in length. In some embodiments, a linker comprises the amino acid sequence SGGS (SEQ ID NO: 23). In some embodiments, a linker comprises $(SGGS)_n$(SEQ ID NO: 24), $(GGGS)_n$(SEQ ID NO: 25), $(GGGGS)_n$(SEQ ID NO: 26), $(G)_n$(SEQ ID NO: 27), $(EAAAK)_n$(SEQ ID NO: 28), $(GGS)_n$(SEQ ID NO: 29), $GS(GGGS)_n$(SEQ ID NO: 30), $GS(GGGGS)_n$(SEQ ID NO: 31) or $(XP)_n$(SEQ ID NO: 32) motif, or a combination of any of these, wherein n is independently an integer between 1 and 30, and wherein X is any amino acid. In some embodiments, n is 1, 2, 3, 4, 5, 6, 7, 8, 9, 10, 11, 12, 13, 14, or 15. A peptide linker may be a flexible linker or a rigid linker. In some embodiments, a linker comprises a plurality of proline residues and is 5-21, 5-14, 5-9, 5-7 amino acids in length, e.g., PAPAP (SEQ ID NO: 33), PAPAPA (SEQ ID NO: 34), PAPAPAP (SEQ ID NO: 35), PAPAPAPA (SEQ ID NO: 36), $P(AP)_n$(SEQ ID NO: 37), wherein n is an integer from 1 to 10. Such proline-rich linkers are also termed "rigid" linkers. In some embodiments, the linker comprises GS(GGGGS)$_n$ (SEQ ID NO: 38), wherein n is an integer from 1 to 10. In some embodiments, the linker comprises a sequence comprising SEQ ID NO: 10, SEQ ID NO: 11, or SEQ ID NO: 12. In some embodiments, the linker comprises an XTEN linker. In some embodiments, the linker comprises a sequence comprising SEQ ID NO: 13.

Provided herein are programmable RNA synthesis systems comprising a customizable DNA binding protein (e.g., ZFA), fused or bridged to a wild type or variant RNA polymerase (e.g., T7 RNA polymerase), along with DNA template comprising a truncated RNA promoter (e.g., T7 promoter) that displays recruitment-dependent activity when placed adjacent to the DNA binding target sequence recognized by the DNA binding protein. RNA transcription activity of the fusion protein can be programmed by directing the binding affinity of the fusion protein to the DNA template or stability of the fusion protein on the DNA template during initiation and/or elongation. For example, the binding affinity between the fusion protein and the DNA template can be adjusted by modifying any elements in the system such as the DNA binding domain, the RNA polymerase, the DNA binding target sequence in the DNA template recognized by the DNA binding protein, and/or a truncated promoter sequence. For example, a variant T7 RNA polymerase with reduced binding affinity to a truncated T7 promoter combined with a ZFA can be used in the system with a DNA template comprising one or more copies of ZFA binding sequence and the truncated T7 promoter, wherein the binding affinity of the fusion protein may depend on the number of copies of ZFA binding sequence in the DNA template.

In some embodiments, the amount of RNA transcribed using fusion proteins described herein (e.g., fusion proteins comprising an RNA polymerase or a functional fragment thereof and a DNA binding domain) may be increased compared to the amount of RNA transcribed using traditional RNA polymerases i.e., RNA polymerases without features or modifications described herein. In some embodiments, the amount of RNA transcribed using fusion proteins described herein (e.g., fusion proteins comprising an RNA polymerase or a functional fragment thereof and a DNA binding domain) may be increased at least by 1.1 fold, 1.2 fold, 1.3 fold, 1.4 fold, 1.5 fold, 1.6 fold, 1.7 fold, 1.8 fold, 1.9 fold, 2.0 fold, 2.1 fold, 2.2 fold, 2.3 fold, 2.4 fold, 2.5 fold, 2.6 fold, 2.7 fold, 2.8 fold, 2.9 fold, 3.0 fold, 3.1 fold, 3.2 fold, 3.3 fold, 3.4 fold, 3.5 fold, 4.0 fold, 4.5 fold, 5.0 fold, 5.5 fold, 6.0 fold, 7.0 fold, 8.0 fold, 9.0 fold, 9.5 fold, 10.0 fold, 10.5 fold, 11.0 fold, 11.5 fold, 12.0 fold, 12.5 fold, 13.0 fold, 14.5 fold, 15.0 fold, 15.5 fold, 16.0 fold, 16.5 fold, 17.0 fold, 17.5 fold, 18.0 fold, 18.5 fold, 19.0 fold, 19.5 fold, 20 fold, 21 fold, 22 fold, 23 fold, 24 fold, 25 fold, 26 fold, 27 fold, 28 fold, 29 fold, 30 fold, 31 fold, 32 fold, 33 fold, 34 fold, 35 fold, 36 fold, 37 fold, 38 fold, 39 fold, 40 fold, 41 fold, 42 fold, 43 fold, 44 fold, 45 fold, 46 fold, 47 fold, 48 fold, 49 fold, 50 fold, 60 fold, 70 fold, 80 fold, 90 fold, 100 fold, 110 fold, 120 fold, 130 fold, 140 fold, 150 fold, 160 fold, 170 fold, 180 fold, 190 fold, 200 fold, 210 fold, 220 fold, 230 fold, 240 fold, 250 fold, 260 fold, 270 fold, 280 fold, 290 fold, 300 fold, 310 fold, 320 fold, 330 fold, 340 fold, 350 fold, 360 fold, 370 fold, 380 fold, 390 fold, 400 fold, 410 fold, 420 fold, 430 fold, 440 fold, 450 fold, 460 fold, 470 fold, 480 fold, 490 fold, 500 fold, 610 fold, 620 fold, 630 fold, 640 fold, 650 fold, 660 fold, 670 fold, 680 fold, 690 fold, 700 fold, 710 fold, 720 fold, 730 fold, 740 fold, 750 fold, 760 fold, 770 fold, 780 fold, 790 fold, 800 fold, 810 fold, 820 fold, 830 fold, 840 fold, 850 fold, 860 fold, 870 fold, 880 fold, 890 fold, 900 fold, 910 fold, 920 fold, 930 fold, 940 fold, 950 fold, 960 fold, 970 fold, 980 fold, 990 fold, 1000 fold, 1100 fold, 1200 fold, 1300 fold, 1400 fold, 1500 fold, 1600 fold, 1700 fold, 1800 fold, 1900 fold, 2000 fold, 2100 fold, 2200 fold, 2300 fold, 2400 fold, 2500 fold, 2600 fold, 2700 fold, 2800 fold, 2900 fold, 3000 fold, 3100 fold, 3200 fold, 3300 fold, 3400 fold, 3500 fold, 3600 fold, 3700 fold, 3800 fold, 3900 fold, 4000 fold, 4100 fold, 4200 fold, 4300 fold, 4400 fold, 4500 fold, 4600 fold, 4700 fold, 4800 fold, 4900 fold, 5000 fold, 5100 fold, 5200 fold, 5300 fold, 5400 fold, 5500 fold, 5600 fold, 5700 fold, 5800 fold, 5900 fold, 6000 fold, 6100 fold, 6200 fold, 6300 fold, 6400 fold, 6500 fold, 6600 fold, 6700 fold, 6800 fold, 6900 fold, 7000 fold, 7100 fold, 7200 fold, 7300 fold, 7400 fold, 7500 fold, 7600 fold, 7700 fold, 7800 fold, 7900 fold, 8000 fold, 8100 fold, 8200 fold, 8300 fold, 8400 fold, 8500 fold, 8600 fold, 8700 fold, 8800 fold, 8900 fold, 9000 fold, 9100 fold, 9200 fold, 9300 fold, 9400 fold, 9500 fold, 9600 fold, 9700 fold, 9800 fold, 9900 fold, or at least by 10000 fold, compared to the amount of RNA transcribed using traditional RNA polymerases i.e., RNA polymerases without features or modifications described herein.

In some embodiments, the amount of DNA template required for RNA synthesis using fusion proteins described herein (e.g., fusion proteins comprising an RNA polymerase or a functional fragment thereof and a DNA binding domain) may be lower than the amount of DNA template required for RNA synthesis using traditional RNA polymerases i.e., RNA polymerases without features or modifications described herein. In some embodiments, the amount of DNA template required for RNA synthesis using fusion proteins described herein (e.g., fusion proteins comprising an RNA polymerase or a functional fragment thereof and a DNA binding domain) may be at least 1.1 fold, 1.2 fold, 1.3 fold, 1.4 fold, 1.5 fold, 1.6 fold, 1.7 fold, 1.8 fold, 1.9 fold, 2.0 fold, 2.1 fold, 2.2 fold, 2.3 fold, 2.4 fold, 2.5 fold, 2.6 fold, 2.7 fold, 2.8 fold, 2.9 fold, 3.0 fold, 3.1 fold, 3.2 fold, 3.3 fold, 3.4 fold, 3.5 fold, 4.0 fold, 4.5 fold, 5.0 fold, 5.5 fold, 6.0 fold, 7.0 fold, 8.0 fold, 9.0 fold, 9.5 fold, or at least 10.0 fold lower than the amount of DNA template required for RNA synthesis using traditional RNA polymerases i.e., RNA polymerases without features or modifications described herein.

In some embodiments, the amount of nucleoside triphosphates (NTPs) required for RNA synthesis using fusion proteins described herein (e.g., fusion proteins comprising an RNA polymerase or a functional fragment thereof and a DNA binding domain) may be lower than the amount of NTPs required for RNA synthesis using traditional RNA polymerases i.e., RNA polymerases without features or modifications described herein. For example, the amount of nucleoside triphosphates (NTPs) required for RNA synthesis using fusion proteins described herein (e.g., fusion proteins comprising an RNA polymerase or a functional fragment thereof and a DNA binding domain) may be at least 1.1 fold, 1.2 fold, 1.3 fold, 1.4 fold, 1.5 fold, 1.6 fold, 1.7 fold, 1.8 fold, 1.9 fold, 2.0 fold, 2.1 fold, 2.2 fold, 2.3 fold, 2.4 fold, 2.5 fold, 2.6 fold, 2.7 fold, 2.8 fold, 2.9 fold, 3.0 fold, 3.1 fold, 3.2 fold, 3.3 fold, 3.4 fold, 3.5 fold, 4.0 fold, 4.5 fold, 5.0 fold, 5.5 fold, 6.0 fold, 7.0 fold, 8.0 fold, 9.0 fold, 9.5 fold, or at least 10.0 fold lower than the amount of NTPs required for RNA synthesis using traditional RNA polymerases i.e., RNA polymerases without features or modifications described herein.

In some embodiments, the binding of the fusion proteins described herein (e.g., fusion proteins comprising an RNA polymerase or a functional fragment thereof and a DNA binding domain) to promoters described herein (e.g., promoter in DNA templates with DNA binding target sequence described herein) may be stronger than the binding of the fusion proteins described herein (e.g., fusion proteins comprising an RNA polymerase or a functional fragment thereof and a DNA binding domain) to traditional promoters or DNA templates without features or modifications described herein (e.g., promoters or DNA templates without DNA binding domains). For example, the binding of the fusion proteins described herein (e.g., fusion proteins comprising an RNA polymerase or a functional fragment thereof and a DNA binding domain) to promoters described herein (e.g., promoter in DNA templates with DNA binding target sequence described herein) may be at least by 100 fold, 200 fold, 300 fold, 400 fold, 500 fold, 600 fold, 700 fold, 800 fold, 900 fold, 1000 fold, 1100 fold, 1200 fold, 1300 fold, 1400 fold, 1500 fold, 1600 fold, 1700 fold, 1800 fold, 1900 fold, 2000 fold, 2100 fold, 2200 fold, 2300 fold, 2400 fold, 2500 fold, 2600 fold, 2700 fold, 2800 fold, 2900 fold, 3000 fold, 3100 fold, 3200 fold, 3300 fold, 3400 fold, 3500 fold, 3600 fold, 3700 fold, 3800 fold, 3900 fold, 4000 fold, 4100 fold, 4200 fold, 4300 fold, 4400 fold, 4500 fold, 4600 fold, 4700 fold, 4800 fold, 4900 fold, 5000 fold, 5100 fold, 5200 fold, 5300 fold, 5400 fold, 5500 fold, 5600 fold, 5700 fold, 5800 fold, 5900 fold, 6000 fold, 6100 fold, 6200 fold, 6300 fold, 6400 fold, 6500 fold, 6600 fold, 6700 fold, 6800 fold, 6900 fold, 7000 fold, 7100 fold, 7200 fold, 7300 fold, 7400 fold, 7500 fold, 7600 fold, 7700 fold, 7800 fold, 7900 fold, 8000 fold, 8100 fold, 8200 fold, 8300 fold, 8400 fold, 8500 fold, 8600 fold, 8700 fold, 8800 fold, 8900 fold, 9000 fold, 9100 fold, 9200 fold, 9300 fold, 9400 fold, 9500 fold, 9600 fold, 9700 fold, 9800 fold, 9900 fold, or at least by 10000 fold stronger than the binding of the fusion proteins described herein (e.g., fusion proteins comprising an RNA polymerase or a functional fragment thereof and a DNA binding domain) to traditional promoters or DNA templates without features or modifications described herein (e.g., promoters or DNA templates without DNA binding domains).

Synthesized RNA

Provided herein are RNAs synthesized by compositions, methods, devices, and systems for the microfluidic polynucleotide synthesis described herein. Synthesized RNAs provided herein comprise a coding RNA or a non-coding RNA. In one example, the coding RNA may comprise a messenger RNA (mRNA). In another example, the non-coding RNA may comprise a guide RNA (gRNA), a small interfering RNA (siRNA), a microRNA (miRNA), a short hairpin (shRNA), piwi-interacting RNA (piRNA), RNA aptamers, transfer RNA (tRNA), or an antisense oligonucleotide (ASO).

Provided herein are gRNAs synthesized by the microfluidic polynucleotide synthesis methods described herein. A gRNA may be used in guiding CRISPR-Cas system to a target sequence for genetic screening, targeted transcriptional regulation, targeted knock-in, and targeted genome editing, including base editing, epigenetic editing, and introducing double strand breaks (DSBs) for homologous recombination-mediated insertion of a nucleotide sequence. Genome editing can refer to the targeted modification of a DNA sequence, including but not limited to, adding, removing, replacing, or modifying existing DNA sequences, and inducing chromosomal rearrangements or modifying transcription regulation elements (e.g., methylation/demethylation of a promoter sequence of a gene) to alter gene expression. CRISPR-Cas system requires a guide system that can locate Cas protein to the target DNA site in the genome. In some instances, the guide system comprises a crispr RNA (crRNA) with a 17-20 nucleotide sequence that is complementary to a target DNA site and a trans-activating crRNA (tracrRNA) scaffold recognized by the Cas protein (e.g., Cas9). The 17-20 nucleotide sequence complementary to a target DNA site is referred to as a spacer while the 17-20 nucleotide target DNA sequence is referred to a protospacer. While crRNAs and tracrRNAs exist as two separate RNA molecules in nature, single guide RNA (sgRNA or gRNA) can be engineered to combine and fuse crRNA and tracrRNA elements into one single RNA molecule. Thus, in one embodiment, the gRNA comprises two or more RNAs, e.g., crRNA and tracrRNA. In another embodiment, the gRNA comprises a sgRNA comprising a spacer sequence for genomic targeting and a scaffold sequence for Cas protein binding. In some instances, the guide system naturally comprises a sgRNA. For example, Cas12a/Cpf1 utilizes a guide system lacking tracrRNA and comprising only a crRNA containing a spacer sequence and a scaffold for Cas12a/Cpf1 binding. While the spacer sequence can be varied depending on a target site in the genome, the scaffold sequence for Cas protein binding can be identical for all gRNAs.

CRISPR-Cas systems described herein can comprise different CRISPR enzymes. For example, the CRISPR-Cas system can comprise Cas9, Cas12a/Cpf1, Cas12b/C2c1, Cas12c/C2c3, Cas12d/CasY, Cas12e/CasX, Cas12g, Cas12h, or Cas12i. Non-limiting examples of Cas enzymes include, but are not limited to, Cas1, Cas1B, Cas2, Cas3, Cas4, Cas5, Cas5d, Cas5t, Cas5h, Cas5a, Cas6, Cas7, Cas8, Cas8a, Cas8b, Cas8c, Cas9 (also known as Csn1 or Csx12), Cas10, Cas10d, Cas12a/Cpf1, Cas12b/C2c1, Cas12c/C2c3, Cas12d/CasY, Cas12e/CasX, Cas12f/Cas14/C2c10, Cas12g, Cas12h, Cas12i, Cas12k/C2c5, Cas13a/C2c2, Cas13b, Cas13c, Cas13d, C2c4, C2c8, C2c9, Csy1, Csy2, Csy3, Csy4, Cse1, Cse2, Cse3, Cse4, Cse5e, Csc1, Csc2, Csa5, Csn1, Csn2, Csm1, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx1S, Csx11, Csf1, Csf2, CsO, Csf4, Csd1, Csd2, Cst1, Cst2, Csh1, Csh2, Csa1, Csa2, Csa3, Csa4, Csa5, GSU0054, Type II Cas effector proteins, Type V Cas effector proteins, Type VI Cas effector proteins, CARF, DinG, homologues thereof, or modified or engineered versions thereof such as dCas9 (endonuclease-dead Cas9) and nCas9 (Cas9 nickase that has inactive DNA cleavage domain). In some cases, the compositions, methods, devices, and systems, described herein, may use the Cas9 nuclease from *Streptococcus pyogenes*, of which amino acid sequences and structures are well known to those skilled in the art.

Binding of a Cas protein to its target DNA sequence (i.e. target dsDNA) requires the presence of a protospacer adjacent motif (PAM), i.e. a short sequence adjacent to the protospacer, on the non-targeted DNA strand, which limits the region in the genome that can be targeted by Cas proteins. Cas proteins from different bacterial species recognize different PAM sequences and make cuts 3-4 nucleotides upstream (e.g., Cas9) or 18-23 nucleotides downstream (e.g., Cas12a/Cpf1) of the PAM sequence. For example, Cas9 from *Streptococcus pyogene* recognizes the PAM sequence 5'-NGG-3' (wherein "N" can be any nucleotide) and cleaves 3 nucleotide upstream of the PAM sequence. In another example, Cas9 from *Staphylococcus aureus* recognizes the PAM sequence 5'-NNGRRN-3' (wherein "N" can be any nucleotide) and cleaves 4 nucleotide upstream of the PAM sequence. Although the PAM sequence is essential for Cas-mediated cleavage, in some instances, the gRNA sequence does not comprise a PAM sequence.

Provided herein are gRNAs comprising a target sequence comprising a spacer that is complementary to a sequence at a target site in the genome. A spacer, as described herein, can comprise about 10 to about 25 nucleotides in length. For example, a spacer sequence that is complementary to a target site sequence in the genome can be about 10, 11, 12, 13, 14, 15, 16, 17, 18, 19, 20, 22, 23, 24, 25, 26, 27, 27, 28, 30, or more nucleotides in length. A target site, as described herein, can comprise a sequence of about 20 nucleotides immediately upstream or 5' of the first nucleotide of the PAM.

Figure 5:
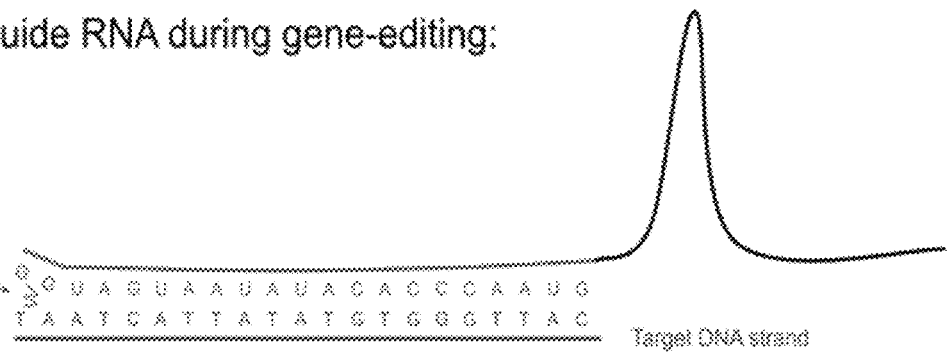
FIG. 5 depicts an exemplary guide RNA (gRNA) containing additional 5' guanine (G) nucleotides that do not match the target DNA sequence.
Figure 6:
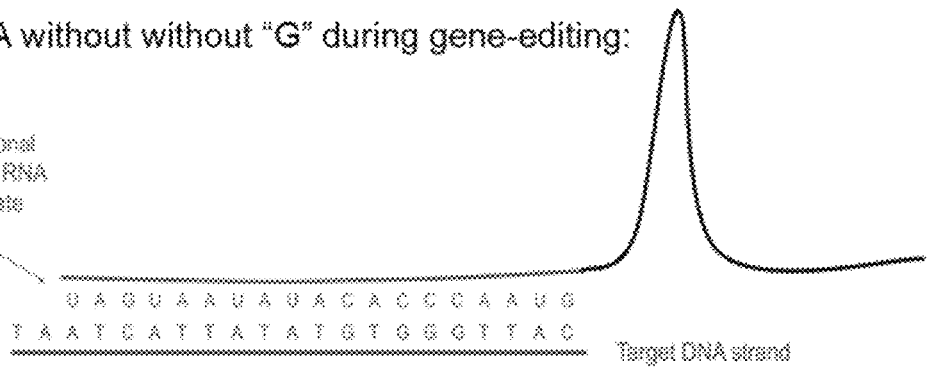
FIG. 6 depicts an exemplary guide RNA (gRNA) perfectly matching the target DNA sequence.

Commercial gRNAs currently produced by in vitro transcription (IVT) typically comprise 1-3 additional guanines (Gs) at the 5' terminus of the gRNA sequence (FIG. 5). T7 RNA polymerase with minimized T7 promoter is commonly used for IVT of gRNAs. As the minimal requirement for transcription initiation is one G in the +1 position, while a naturally occurring transcription initiation sequence can have up to 3 Gs in positions +1, +2 and +3 from 5' terminus of a gRNA. Such additional Gs in IVT synthesized gRNAs may result in extra Gs at the 5' terminus of the spacer sequence, for example, in Cas9 gRNAs, creating unpaired overhang or mismatches between a gRNA and its target sequence. This mispairing can decrease the efficiency of targeted genome editing (FIG. 5). Provided herein are gRNAs that do not comprise mismatched nucleotides at the 5' terminus of the spacer to improve 5' terminal pairing with the target site DNA sequence. gRNAs without the additional one or more Gs at the 5' terminus of the spacer can support highly accurate genome editing with reduced off-target effects (FIG. 6). Provided herein are gRNAs, wherein at least 1, at least 2, or at least 3 consecutive nucleotides at the 5' terminus of the gRNA sequences are 100% identical to the 3' terminus of the target sequence in a genome. gRNAs synthesized by the compositions, methods, devises, and systems, described herein, exhibit improved or enhanced pairing with a target sequence via complementary base pairing with the target sequence in a target gene compared to a gRNA comprising additional 5' terminal G nucleotide that is not present in the protospacer sequence or complementary to the 3' terminus of the target sequence.

Provided herein are gRNAs exhibiting enhanced editing efficiency of a target sequence when gRNAs are contacted with the target sequence in a complex with a CRISPR-Cas system (e.g., CRISPR-Cas9, CRISPR-Cas12a/Cpf1, etc.). For example, gRNAs provided herein (e.g., gRNAs not comprising additional one or more G nucleotides at the 5' terminus or gRNAs not comprising a G nucleotide in the 5' terminal codon) can exhibit enhanced editing efficiency of a target sequence when in complex with a CRISPR-Cas system compared to a gRNA comprising additional one or more 5' terminal G nucleotides, wherein the additional one or more 5' terminal G nucleotides are not present in the protospacer sequence or not complementary to one or more nucleotides at the 3' terminus of the target sequence in a genome. As used herein, the term "codon" generally refers to three consecutive nucleotides, which may or may not encode an amino acid. As used herein, the "efficiency of editing" or "editing efficiency" can refer to the ability of a gRNA directed effector protein (e.g., CRISPR-Cas protein) to modify a target DNA sequence. Non-limiting examples of modification of a target sequence can include introducing a double stranded break, modifying a nucleobase, inducing chromosomal rearrangements, and modifying methylation/demethylation of a promoter sequence of a gene. A target sequence may be located in a gene or in a promoter region in a genome. An effector protein may be a gRNA directed nuclease, e.g., Cas protein such as Cas9 or any other Cas protein described herein. The editing efficiency can be measured by using any methods well known to one skilled in the art. For example, the efficiency of genome editing or editing efficiency can be measured by using tracking of indels by decomposition (TIDE) analysis, surveyor nuclease assay, junction PCR, droplet digital PCR (ddPCR), denaturing high-performance liquid chromatography (DHPLC), PCR single-stranded conformational polymorphism (SSCP), high-resolution melting (HRM), restriction enzyme digestion-suppressed PCR (RE-PCR), engineered nuclease-induced translocations (ENIT), restriction enzyme digestion, Sanger DNA sequencing, deep sequencing such as next generation sequencing (NGS), or any combination thereof. The term "indel(s)", as used herein, refers to the insertion or deletion of a nucleotide base within a nucleic acid. In some embodiments, the efficiency of genome editing, e.g., generating a double-strand break, can be measured by TIDE analysis, a three-step method whereby the region targeted by the nuclease (e.g., Cas9) is PCR-amplified from DNA isolated from cells transfected with CRISPR-Cas system and gRNAs. Amplicons of 500-1500 bp generated around the target site are subject to conventional Sanger DNA sequencing followed by analysis using the web-based TIDE software. Any sequence modifications made by the nuclease are visualized in a graph of the sequence with the aberrant base signal. The software also provides precise localization of break sites and estimated statistical significance of each indel. In some embodiments, the editing efficiency e.g., the efficiency of generating a DNA break in the intended target site, is at least 30%, 35%, 40%, 45%, 50%, 55%, 60%, 65%, 70%, 75%, 80%, 85%, 90%, 95%, or 99%.

Further provided herein are gRNAs that exhibit reduced off-target editing (e.g., editing of a non-target sequence) when gRNAs are contacted with the target sequence in a complex with a CRISPR-Cas system (e.g., CRISPR-Cas9, CRISPR-Cas12a/Cpf1, etc.). For example, gRNAs provided herein (e.g., gRNAs not comprising additional one or more G nucleotides at the 5' terminus or gRNAs not comprising a G nucleotide in the 5' terminal codon) can exhibit reduced off-target editing when in complex with a CRISPR-Cas system compared to a gRNA comprising additional one or more 5' terminal G nucleotides, wherein the additional one or more 5' terminal G nucleotides are not present in the protospacer sequence or not complementary to one or more nucleotides at the 3' terminus of the target sequence in a genome. In some embodiments, the off-target editing can be reduced by at least 10%, 15%, 20%, 25%, 30%, 35%, 40%, 45%, 50%, 55%, 60%, 65%, 70%, 75%, 80%, 85%, 90%, 95%, or 99%.

Provided herein are gRNAs comprising a secondary structure. For example, the scaffold region of the gRNA recognized by the Cas protein may form a secondary structure such as a stem, a hairpin, and/or a loop. Stems or hairpins, described herein, can be about 3-10 nucleotides in length. Loops can be about 6-20 nucleotides in length. Stems may comprise one or more bulges of 1-10 nucleotides in length.

Further provided herein are gRNAs comprising a target sequence comprising one or more mismatched nucleotide, i.e. the spacer sequence may comprise one or more nucleotides that are not complementary to the target site sequence in the genome. Spacers described herein may harbor various number of mismatches, for example, 1, 2, 3, 4, 5, 6, 7, 8, 9, 10, 11, 12, 13, 14, or 15 mismatches. In some embodiments, a spacer comprises at most 1, 2, 3, 4, or 5 mismatches. In some embodiments, a spacer does not comprise any mismatch as compared to a protospacer sequence at the target site, i.e. the spacer hybridizes with the target sequence at 100%. Spacers described herein may comprise at least 1 to at least 5 mismatched nucleotides. For example, the spacer may comprise at least 1, at east 2, at least 3, at least 4, or at least 5 mismatched nucleotides. In some embodiments, the spacer may comprise at most 3, at most 4, at most 5, at most 6, or at most 7 mismatched nucleotides. In some embodiments, the one or more mismatched nucleotides may be located at the 5' terminus of the spacer sequence. In some embodiments, the one or more mismatched nucleotides may be located at the 3' terminus of the spacer sequence. In some embodiments, the one or more mismatched nucleotides may be internally located in the spacer sequence.

Provided herein are gRNAs comprising a sequence extension. A sequence extension can be on the 5' or 3' terminus or can be added internally. For example, the 5' terminus of the gRNA Cas12a/Cpf1 (e.g., crRNA) can be extended by 2-59 nucleotides. Extending the 5' terminus of the Cas12a/Cpf1 gRNA, which comprises a scaffold sequence for Cas12a/Cpf1 binding on the 5' terminus and a target sequence on the 3' terminus, can increase the editing efficiency and delivery of Cas12a/Cpf1 in vitro and in vivo. It can also increase tolerance of gRNAs to chemical modifications, leading to enhanced stability of gRNAs. In another example, a gRNA of Cas9 comprising an internal extension of 2-10 nucleotides to extend the stem region of the stem loop structure can increases gene knockout efficiency in CRISPR-Cas9-mediated genome editing. In some instances, a gRNA may comprise two or more of crRNA sequences and tracrRNA sequence and bind two or more Cas proteins and a target DNA sites at two or more distinct regions in the genome. In some embodiments, the gRNAs described herein may comprise a 5' sequence extension. In some embodiments, the gRNAs described herein may comprise a 3' sequence extension. In some embodiments, the gRNAs described herein may comprise an internal sequence extension. In some embodiments, the sequence extension can comprise about at least 1 to at least 70 nucleotides. In some embodiments, the sequence extension can comprise at least 1, at least 5, at least 10, at least 20, at least 30, at least 40, at least 50, at least 60, or at least 70 nucleotides.

Provided herein are gRNAs comprising a nucleotide analog, e.g., guanine (G) analog. A nucleotide analog comprises an alteration in a phosphate backbone, a sugar, and/or nucleobases. Non-limiting examples of nucleotide analog include 2-aminoadenosine, 2-thiothymidine, inosine, pyrrolo-pyrimidine, 3-methyl adenosine, 5-methylcytidine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, 2-thiocytidine, 2'-fluororibose, ribose, 2'-deoxyribose, arabinose, hexose, phosphorothioate linkages, 5'-N-phosphoramidite linkages, intercalated bases, and/or chemically modified bases. Provided herein are gRNAs comprising a 5' terminal G analog that can exhibit enhanced editing efficiency of a target sequence when in complex with a CRISPR-Cas system compared to a gRNA lacking 5' terminal G analog.

Further provided herein are RNAs comprising 10 to 100 nucleotides in length. In some embodiments, the synthesized RNA comprises 10, 20, 30, 40, 50, 60, 70, 80, 90, or 100 nucleotides in length. In some embodiments, the synthesized RNA comprises 10 to 20 nucleotides, 10 to 30 nucleotides, 10 to 40 nucleotides, 10 to 50 nucleotides, 10 to 60 nucleotides, 10 to 70 nucleotides, 10 to 80 nucleotides, 10 to 90 nucleotides, 10 to 100 nucleotides, 20 to 30 nucleotides, 20 to 40 nucleotides, 20 to 50 nucleotides, 20 to 60 nucleotides, 20 to 70 nucleotides, 20 to 80 nucleotides, 20 to 90 nucleotides, 20 to 100 nucleotides, 30 to 40 nucleotides, 30 to 50 nucleotides, 30 to 60 nucleotides, 30 to 70 nucleotides, 30 to 80 nucleotides, 30 to 90 nucleotides, 30 to 100 nucleotides, 40 to 50 nucleotides, 40 to 60 nucleotides, 40 to 70 nucleotides, 40 to 80 nucleotides, 40 to 90 nucleotides, 40 to 100 nucleotides, 50 to 60 nucleotides, 50 to 70 nucleotides, 50 to 80 nucleotides, 50 to 90 nucleotides, 50 to 100 nucleotides, 60 to 70 nucleotides, 60 to 80 nucleotides, 60 to 90 nucleotides, 60 to 100 nucleotides, 70 to 80 nucleotides, 70 to 90 nucleotides, 70 to 100 nucleotides, 80 to 90 nucleotides, 80 to 100 nucleotides, or 90 to 100 nucleotides in length. In some embodiments, the synthesized RNA comprises at least 10, at least 20, at least 30, at least 40, at least 50, at least 60, at least 70, at least 80, or at least 90 nucleotides in length. In some embodiments, the synthesized RNA comprises at most 20, at most 30, at most 40, at most 50, at most 60, at most 70, at most 80, at most 90, or at most 100 nucleotides in length. In some embodiments, the synthesized RNA comprises at least 20 nucleotides in length. In some embodiments, the synthesized RNA comprises at least 80 nucleotides in length. In some embodiments, the synthesized RNA comprises at most 30 nucleotides in length.

The synthesized RNA, as described herein, can comprise one or more modifications. For example, the synthesized RNA can comprise synthetic nucleotide, synthetic nucleotide analog, nucleotide derivatives, and/or modified nucleotides. In some embodiments, the one or more modification can increase stability of the synthesized RNAs. In some embodiments, the one or more modification can enhance biological activity of the synthesized RNAs. In some embodiments, a modification of internucleotide linkage using phosphorothioate (PS) bond substitutes can be introduced to inhibit exonuclease-mediated degradation of RNAs. In some embodiments, the one or more modifications can be made at any location of the synthesized RNA. The synthesized RNA, as described herein, can comprise natural nucleosides (e.g., adenosine, guanosine, cytidine, and uridine), nucleoside analogs (e.g., 2-aminoadenosine, 2-thiothymidine, inosine, pyrrolo-pyrimidine, 3-methyl adenosine, 5-methylcytidine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), and/or modified phosphate groups (e.g., phosphorothioates and 5'-N-phosphoramidite linkages).

Provided herein are RNAs comprising a chemical modification. Chemical modifications as described herein may comprise one or more 5' modifications selected from the group consisting of 5' triphosphate, 5' diphosphate, 5' monophosphate, and 5' hydroxyl. In another embodiment, the chemical modification comprises one or more ribose modifications selected from the group consisting of 2'-O-methylation (2'OMe), 2'-O-methoxy-ethyl (2'-MOE), 2'-fluoro (2'F), 2-deoxy-2'-thio, and 2'-azido. In some embodiments, the chemical modification comprises one or more internucleotide linkage modifications selected from the group consisting of phosphorothioate, methylphosphonate, phosphonocarboxylate, phosphonothiocarboxylate, boranophosphonate, alkylphosphonate, and alkylphosphonate.

Chemical modifications can further comprise modified nucleotides comprising one or more heterocyclic modifications selected from the group consisting of 2,6-Diaminopurine, 2-Aminopurine, inosine, 2-aminoadenosine, N6-methyladenosine, N6,2'-O-dimethyladenosine, N1-methyladenosine, 2-amino-6-chloropurineriboside, 5-methylcytidine, 5-hydroxymethylcytidine, 8-oxo-7,8-dihydroguanosine, pseudouridine, N4-acetylcytidine, 5-bromo-uridine, 5-methyluridine, and 5-nitroindole. In some embodiments, the chemical modification comprises, but is not limited to, modified nucleotides comprising one or more 5' cap modifications selected from the group consisting of GpppG, 7-methylguanylate (m7GpppG), m2,2,7GpppG, and m7-3'-OGpppG (ARCA).

In some instances, the chemical modification comprises modified nucleotides comprising one or more 5' cap modifications selected from the group consisting of an attachment chemistry (e.g., biotin), a dye, a cell targeting moiety, an active chemistry, and an amino modifier. In some embodiments, the attachment chemistry can comprise biotin. In some embodiments, the dye comprises fluorescein. In some embodiments, the cell targeting moiety comprises digoxigenin. In some embodiments, the active chemistry comprises azides, acrydite, thiols, or alkynes. In some embodiments, the amino modifier comprises aminoallyl.

Nucleic Acid Libraries

Provided herein are nucleic acid libraries comprising purified RNAs synthesized using the microfluidic polynucleotide synthesis described herein. The nucleic acid libraries provided herein comprise highly pure and uniform RNA molecules. Purified RNAs, as described herein, can comprise a guide RNA (gRNA), a messenger RNA (mRNA), a small interfering RNA (siRNA), a short hairpin RNA (shRNA), a microRNA (miRNA), piwi-interacting RNA (piRNA), RNA aptamers, transfer RNA (tRNA), or antisense oligonucleotide (ASO). As described herein, the purity of RNAs can be measured and analyzed using methods including, but not limited to, Isotachophoresis (ITP), capillary electrophoresis (CE), and/or ITP coupled with microchip-based CE. Further provided herein are nucleic acid libraries comprising RNAs with highly accurate sequence compared to the predetermined RNA sequence encoded by the DNA template. In some instances, for nucleic acid libraries wherein each RNA comprises at least 20, 30, 40, 50, 60, 70, 80, 90, 100 nucleotides, the percentage of full-length sequences is at least 40%, 45%, 50%, 52%, 55%, 58%, 60%, 62%, 65%, 68%, 70%, 72%, 75%, 78%, 80%, 82%, 85%, 88%, 90%, or 95%. In some instances, at least about 70%, 75%, 80%, 85%, 90%, 95%, 99%, or more RNAs in the nucleic acid library have no errors, e.g., nucleotide changes, in the sequence. In some instances, at least about 70%, 75%, 80%, 85%, 90%, 95%, 99%, or more RNAs in the nucleic acid library have insertions or deletions (indels) in the sequence. In some instances, the nucleic acid libraries described herein have an error rate of less than 1:100, 1:500, 1:1000, 1:1500, 1:2000, 1:3000, 1:5000, 1:10,000 or less when compared to the predetermined RNA sequence encoded by the DNA template.

Nucleic acid libraries described herein may be measured in terms of uniformity, a measure of RNA species representation. Uniformity may be measured on both a per cluster and per device basis.

In some instances, 99% of the RNAs have an abundance that is within about 0.05, 0.1, 0.2, 0.5, 0.7, 1, 1.2, 1.5, 1.7 or about within 2× of the mean abundance. In some instances, 97% of the polynucleotides have an abundance that is within about 0.05, 0.1, 0.2, 0.5, 0.7, 1, 1.2, 1.5, 1.7 or about within 2× of the mean abundance. In some instances, 60%, 75%, 80%, 85%, 90%, 95%, 97%, or 99% of the sequences have an abundance that is within 2× of the mean. In some instances, 60%, 75%, 80%, 85%, 90%, 95%, 97%, or 99% of the sequences have an abundance that is within 1.5× of the mean. In some instances, 60%, 75%, 80%, 85%, 90%, 95%, 97%, or 99% of the sequences have an abundance that is within 1× of the mean.

Provided herein are nucleic acid libraries comprising RNA molecules having high uniformity following microfluidic polynucleotide synthesis. For example, at least about 60%, 75%, 80%, 85%, 90%, 95%, 97%, or 99% of RNAs in the nucleic acid libraries described herein can be represented within 1.5× of the mean frequency for the entire library. In some embodiments, the nucleic acid library comprises at least 50 RNAs, wherein each of the at least 50 RNAs encodes a different guide RNA (gRNA) sequence, and at least about 90% of the at least 50 RNAs are each present in the nucleic acid library in an amount within 1.5× of a mean frequency for the at least 50 RNAs in the library. In some embodiments, the nucleic acid library comprises at least 50 RNAs, wherein each of the at least 50 RNAs encodes a different guide RNA (gRNA) sequence, and at least about 95% of the at least 50 RNAs are each present in the nucleic acid library in an amount within 1.5× of a mean frequency for the at least 50 RNAs in the library. In some embodiments, the nucleic acid library comprises at least 50 RNAs, wherein each of the at least 50 RNAs encodes a different guide RNA (gRNA) sequence, and at least about 99% of the at least 50 RNAs are each present in the nucleic acid library in an amount within 1.5× of a mean frequency for the at least 50 RNAs in the library.

Provided herein are nucleic acid libraries comprising at least 100,000 purified RNAs. For example, the nucleic acid libraries can comprise at least 100,000, 150,000, 200,000, 250,000, 300,000, 350,000, 400,000, 450,000, 500,000, 550,000, 600,000, 650,000, 700,000, 750,000, 800,000, 850,000, 900,000, 950,000, or 1000,000 purified RNAs. In some instances, the purified RNAs comprise RNA sequences and each of the RNA sequences comprises at least 20, at least 30, at least 40, at least 50, at least 60, at least 70, at least 80, at least 90, or at least 100 nucleotides in length. In some embodiments, each of the RNA sequences comprises 10 to 20 nucleotides, 10 to 30 nucleotides, 10 to 40 nucleotides, 10 to 50 nucleotides, 10 to 60 nucleotides, 10 to 70 nucleotides, 10 to 80 nucleotides, 10 to 90 nucleotides, 10 to 100 nucleotides, 20 to 30 nucleotides, 20 to 40 nucleotides, 20 to 50 nucleotides, 20 to 60 nucleotides, 20 to 70 nucleotides, 20 to 80 nucleotides, 20 to 90 nucleotides, 20 to 100 nucleotides, 30 to 40 nucleotides, 30 to 50 nucleotides, 30 to 60 nucleotides, 30 to 70 nucleotides, 30 to 80 nucleotides, 30 to 90 nucleotides, 30 to 100 nucleotides, 40 to 50 nucleotides, 40 to 60 nucleotides, 40 to 70 nucleotides, 40 to 80 nucleotides, 40 to 90 nucleotides, 40 to 100 nucleotides, 50 to 60 nucleotides, 50 to 70 nucleotides, 50 to 80 nucleotides, 50 to 90 nucleotides, 50 to 100 nucleotides, 60 to 70 nucleotides, 60 to 80 nucleotides, 60 to 90 nucleotides, 60 to 100 nucleotides, 70 to 80 nucleotides, 70 to 90 nucleotides, 70 to 100 nucleotides, 80 to 90 nucleotides, 80 to 100 nucleotides, or 90 to 100 nucleotides in length. In some embodiments, each of the RNA sequences comprises at most 20, at most 30, at most 40, at most 50, at most 60, at most 70, at most 80, at most 90, or at most 100 nucleotides in length. In some embodiments, each of the RNA sequences comprises at least 20 nucleotides in length. In some embodiments, each of the RNA sequences comprises at least 80 nucleotides in length. In some embodiments, each of the RNA sequences comprises at most 30 nucleotides in length.

Further provided herein, are nucleic acid libraries comprising a plurality of RNAs, wherein each of the RNAs comprises the same RNA (e.g., gRNA, miRNA, siRNA, mRNA, piRNA, shRNA, tRNA, RNA aptamer, or ASO) sequence. In some instances, the nucleic acid libraries comprise two or more groups of RNAs, wherein each of the two or more groups of RNAs comprise a different RNA sequence and each or the two or more groups of RNAs comprise a plurality of RNAs. In some instances, the nucleic acid libraries comprise least 50, at least 100, at least 200, at least 300, at least 400, or at least 500 different groups of RNAs, each comprising a different RNA sequence. In some embodiments, the nucleic acid libraries comprise at least 200 groups of RNAs, each comprising a different RNA sequence. For example, a nucleic acid library can comprise 200 groups of RNAs and each of the 200 groups of RNAs comprises a plurality of RNA molecules, and each of the 200 groups of RNAs comprises a different RNA sequence; thus, the nucleic acid library can comprise a plurality of RNAs with 200 different RNA sequences.

The nucleic acid libraries, described herein, can further comprise additional components. Additional components may comprise any elements included in the microfluidic polynucleotide synthesis described herein, e.g., NHS esters reaction products, dissociated transcription complex or fragments, transcription reaction components, nucleotide factors, ITP and/or CE buffers, microfluidic coating polymers, and UV adjuncts. For example, the nucleic acid libraries can comprise at least one single-stranded DNA (ssDNA) encoding a truncated RNA polymerase promoter, which is used as the template for microfluidic polynucleotide synthesis. Additional components can also include, but are not limited to, an RNA polymerase or a functional fragment or a variant thereof, a fusion protein comprising an RNA polymerase or a functional fragment or a variant thereof and a DNA binding protein or a functional fragment or a variant thereof, a plurality of oligonucleotides, a plurality of single nucleotides, a Tris-HCL, a MgCl2, Mn2+, spermidine, a dithiothreitol, a DNA template, a NaCl, a beta-mercaptoethanol (β-ME), an Ethylenediaminetetraacetic acid (EDTA), a glycerol, a pyrophosphatase, a Triton X-100, a Tween-20, a potassium glutamate, a tris(2-carboxyethyl)phosphine (TCEP), a bovine serum albumin (BSA), a polyethylene glycol (PEG) 8000, and an acetate.

Provided herein are nucleic acid libraries further comprising at least one oligonucleotide. For example, an oligonucleotide can be an RNA primer such as initiator oligos or terminator oligos. In some embodiments, the at least one oligonucleotide comprises 2 to 10 nucleotides in length. In some embodiments, the at least one oligonucleotide comprises 2, 3, 4, 5, 6, 7, 8, 9, or 10 nucleotides in length. In some embodiments, the at least one oligonucleotide comprises RNA. In some embodiments, the at least one oligonucleotide comprises DNA. In some embodiments, the at least one oligonucleotide is 80%, 85%, 90%, 95%, or 100% identical to 2, 3, 4, 5, 6, 7, 8, 9, or 10 consecutive nucleotides at or near the 5' end of a purified RNA, e.g., gRNA, miRNA, siRNA, or mRNA. In some embodiments, the at least one oligonucleotide is 80%, 85%, 90%, 95%, or 100% identical to 2, 3, 4, 5, 6, 7, 8, 9, or 10 consecutive nucleotides at or near the 3' end of a purified RNA, e.g., gRNA, miRNA, siRNA, or mRNA. In a preferred embodiment, the at least one oligonucleotide is 100% identical to 2, 3, 4, 5, 6, 7, 8, 9, or 10 consecutive nucleotides at or near the 5' end of a purified gRNA. In another embodiment, the at least one oligonucleotide is 100% identical to 2, 3, 4, 5, 6, 7, 8, 9, or 10 consecutive nucleotides at or near the 3' end of a purified gRNA. In some embodiments, the at least one oligonucleotide can comprise a chemical modification described herein (See, e.g., paragraphs [107]-[110]. Non-limiting examples of an initiator oligo include ApA, ApU, ApG, ApC, UpA, UpU, UpG, UpC, GpA, GpU, GpG, GpC, CpA, CpU, CpG, CpC, wherein p indicates the phosphodiester bond and remaining 5' phosphate group.

Provided herein are nucleic acid libraries comprising additional components described herein, wherein the additional components can be present in the nucleic acid libraries in the amount of less than 10 pM, 9 pM, 8 pM, 7 pM, 6 pM, 5 pM, 4 pM, 3 pM, 2 pM, 1 pM, 0.5 pM, 0.1 pM, 0.05 pM, or less than 0.01 pM. Further provided herein are nucleic acid libraries comprising additional components described herein, wherein the additional components can be present in the nucleic acid libraries in the amount of at least 0.01 pM, 0.05 pM, 0.1 pM, 0.5 pM, 1 pM, 2 pM, 3 pM, 4 pM, 5 pM, 6 pM, 7 pM, 8 pM, 9 pM, or at least 10 pM. Further provided herein are nucleic acid libraries comprising additional components described herein, wherein the additional components can be present in the nucleic acid libraries in the amount of at most 20 pM, 15 pM, 10 pM, 9 pM, 8 pM, 7 pM, 6 pM, 5 pM, 4 pM, 3 pM, 2 pM, 1 pM, 0.5 pM, 0.1 pM, 0.05 pM, or at most 0.01 pM. For example, the nucleic acid library comprising a plurality of purified RNAs can further comprise at least 1 pM of microfluidic coating polymers. In some embodiments, the at least 1 pM of microfluidic coating polymers comprises at most 10 pM of microfluidic coating polymers. For example, the nucleic acid library comprising a plurality of purified RNAs can further comprise at least 1 pM of UV adjuncts. In some embodiments, the at least 1 pM of UV adjuncts comprises at most 10 pM of UV adjuncts.

Computer Systems

Any of the systems described herein, may be operably linked to a computer and may be automated through a computer either locally or remotely. In various instances, the methods and systems of the invention may further comprise software programs on computer systems and uses thereof. Accordingly, computerized control for the synchronization of the dispense/vacuum/refill functions such as orchestrating and synchronizing the material deposition device movement, dispense action and vacuum actuation are within the bounds of the invention. The computer systems may be programmed to interface between the user specified template sequence and the position of a material deposition device to deliver the correct reagents to specified regions of the surface.

Figure 7:
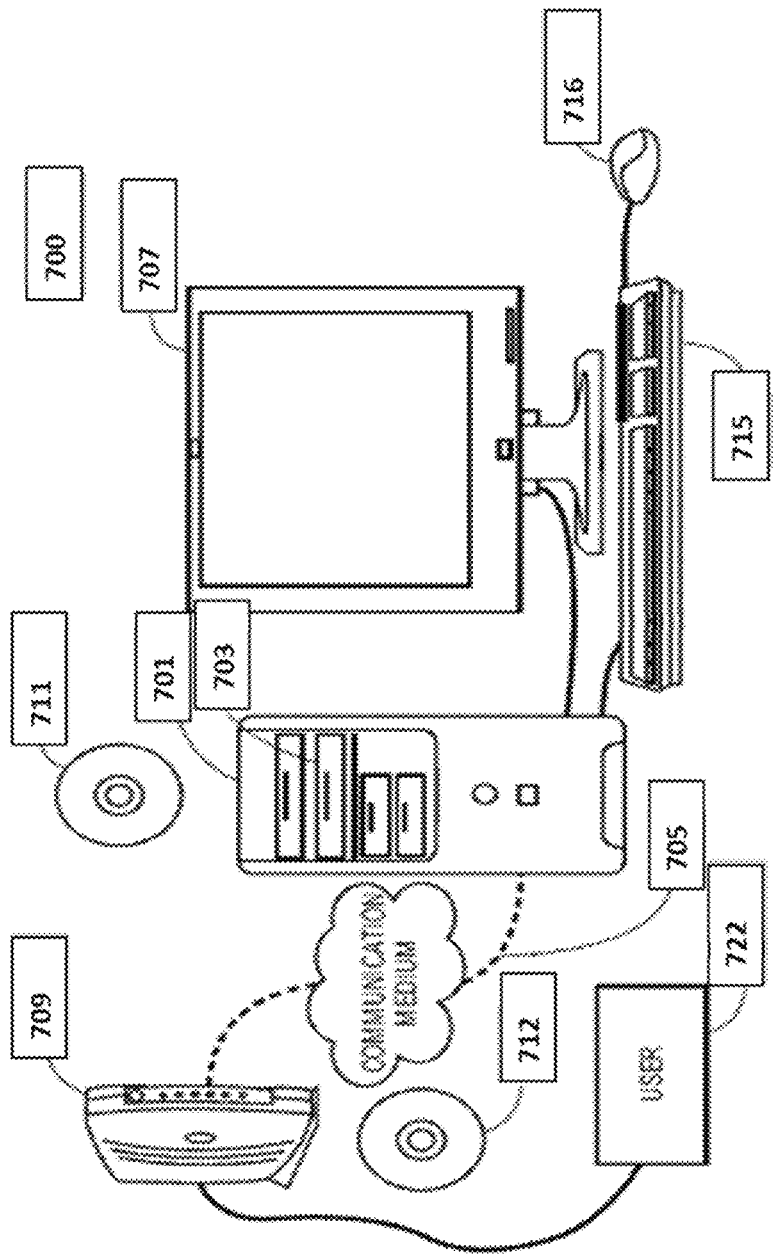
FIG. 7 illustrates a computer system.

The computer system 700 illustrated in FIG. 7 may be understood as a logical apparatus that can read instructions from media 711 and/or a network port 705, which can optionally be connected to server 709 having fixed media 712. The system, such as shown in FIG. 7 can include a CPU 701, disk drives 703, optional input devices such as keyboard 715 and/or mouse 716 and optional monitor 707. Data communication can be achieved through the indicated communication medium to a server at a local or a remote location. The communication medium can include any means of transmitting and/or receiving data. For example, the communication medium can be a network connection, a wireless connection or an interne connection. Such a connection can provide for communication over the World Wide Web. It is envisioned that data relating to the present disclosure can be transmitted over such networks or connections for reception and/or review by a party 722 as illustrated in FIG. 7.

Figure 8:
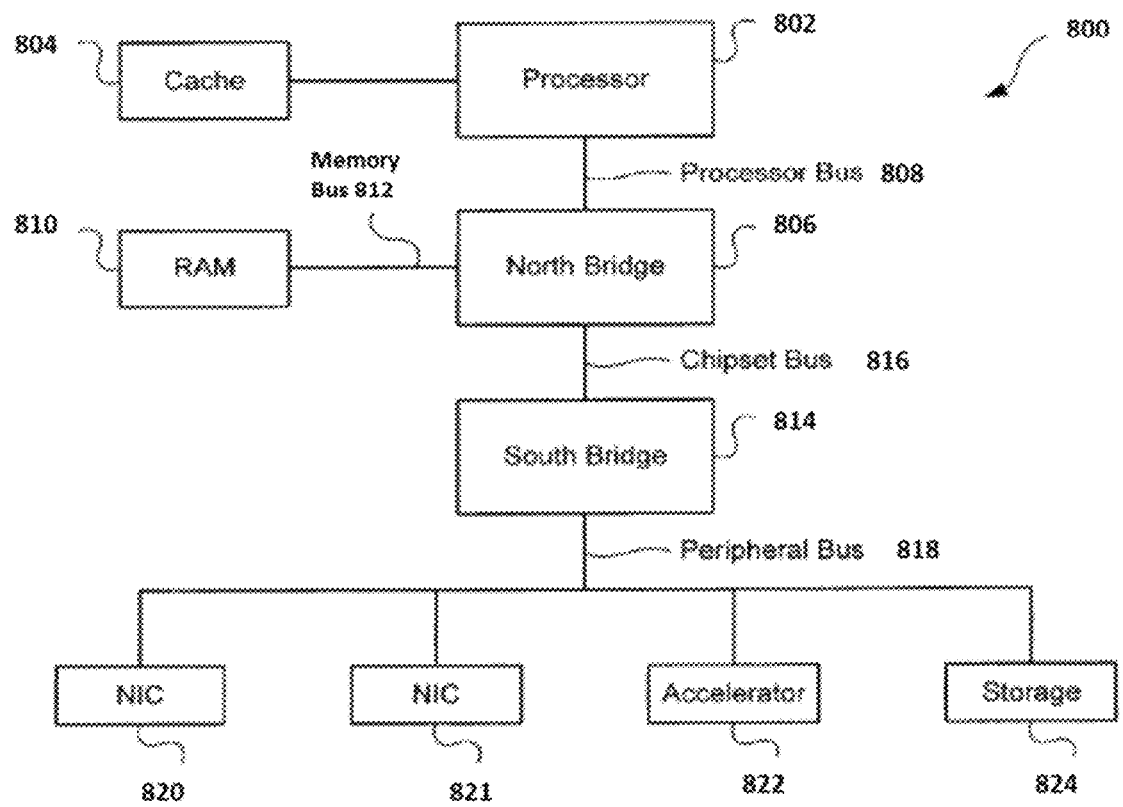
FIG. 8 is a block diagram illustrating architecture of a computer system.

Provided herein is a block diagram illustrating a first example architecture of a computer system 800 that can be used in connection with example instances of the present invention as shown in FIG. 8. As depicted in FIG. 8, the example computer system can include a processor 802 for processing instructions. Non-limiting examples of processors include: Intel Xeon™ processor, AMD Opteron™ processor, Samsung 8-bit RISC ARM 1176JZ(F)-S v1.0™ processor, ARM Cortex-A8 Samsung S5PC100™ processor, ARM Cortex-A8 Apple A4™ processor, Marvell PXA 930™ processor, or a functionally-equivalent processor. Multiple threads of execution can be used for parallel processing. In some instances, multiple processors or processors with multiple cores can also be used, whether in a single computer system, in a cluster, or distributed across systems over a network comprising a plurality of computers, cell phones, and/or personal data assistant devices.

As illustrated in FIG. 8, a high speed cache 804 can be connected to, or incorporated in, the processor 802 to provide a high speed memory for instructions or data that have been recently, or are frequently, used by processor 802. The processor 802 is connected to a north bridge 806 by a processor bus 808. The north bridge 806 is connected to random access memory (RAM) 810 by a memory bus 812 and manages access to the RAM 810 by the processor 802. The north bridge 806 is also connected to a south bridge 88 by a chipset bus 816. The south bridge 814 is, in turn, connected to a peripheral bus 818. The peripheral bus can be, for example, PCI, PCI-X, PCI Express, or other peripheral bus. The north bridge and south bridge are often referred to as a processor chipset and manage data transfer between the processor, RAM, and peripheral components on the peripheral bus 818. In some alternative architectures, the functionality of the north bridge can be incorporated into the processor instead of using a separate north bridge chip. In some instances, system 800 can include an accelerator card 822 attached to the peripheral bus 818. The accelerator can include field programmable gate arrays (FPGAs) or other hardware for accelerating certain processing. For example, an accelerator can be used for adaptive data restructuring or to evaluate algebraic expressions used in extended set processing.

Software and data are stored in external storage 824 and can be loaded into RAM 810 and/or cache 804 for use by the processor. The system 800 includes an operating system for managing system resources; non-limiting examples of operating systems include: Linux, Windows™, MACOS™, BlackBerry OS™, iOS™, and other functionally-equivalent operating systems, as well as application software running on top of the operating system for managing data storage and optimization in accordance with example instances of the present invention. In this example, system 800 also includes network interface cards (NICs) 820 and 821 connected to the peripheral bus for providing network interfaces to external storage, such as Network Attached Storage (NAS) and other computer systems that can be used for distributed parallel processing.

Figure 9:
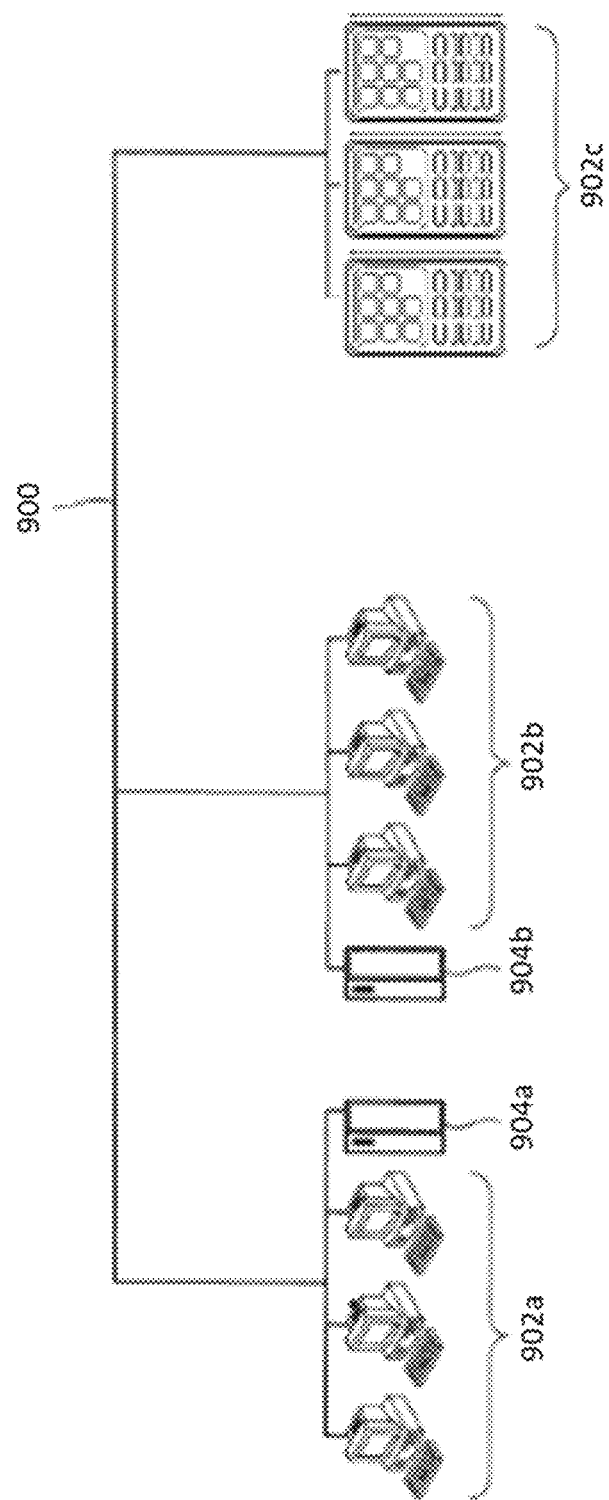
FIG. 9 is a diagram demonstrating a network configured to incorporate a plurality of computer systems, a plurality of cell phones and personal data assistants, and Network Attached Storage (NAS).

Provided herein is a diagram showing a network 900 with a plurality of computer systems 902a, and 902b, a plurality of cell phones and personal data assistants 902c, and Network Attached Storage (NAS) 904a, and 904b as shown in FIG. 9. In example instances, systems 902a, 902b, and 902c can manage data storage and optimize data access for data stored in Network Attached Storage (NAS) 904a and 904b. A mathematical model can be used for the data and be evaluated using distributed parallel processing across computer systems 902a, and 902b, and cell phone and personal data assistant systems 902c. Computer systems 902a, and 902b, and cell phone and personal data assistant systems 902c can also provide parallel processing for adaptive data restructuring of the data stored in Network Attached Storage (NAS) 904a and 904b. FIG. 9 illustrates an example only, and a wide variety of other computer architectures and systems can be used in conjunction with the various instances of the present invention. For example, a blade server can be used to provide parallel processing. Processor blades can be connected through a back plane to provide parallel processing. Storage can also be connected to the back plane or as Network Attached Storage (NAS) through a separate network interface.

In some example instances, processors can maintain separate memory spaces and transmit data through network interfaces, back plane, or other connectors for parallel processing by other processors. In other instances, some or all of the processors can use a shared virtual address memory space.

Figure 10:
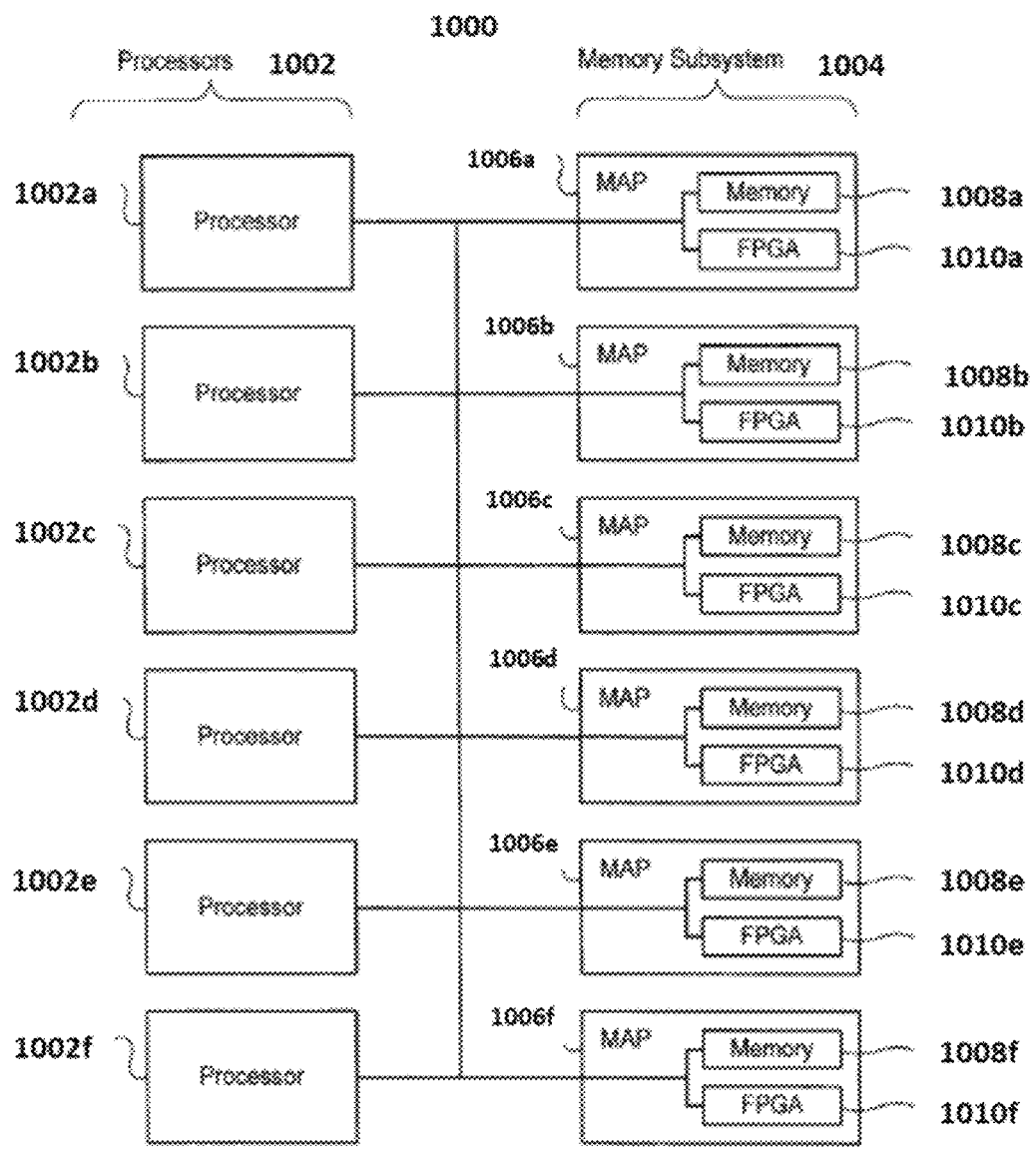
FIG. 10 is a block diagram of a multiprocessor computer system using a shared virtual address memory space.

Provided herein is a block diagram of a multiprocessor computer system 1000 using a shared virtual address memory space as illustrated in FIG. 10 in accordance with an example embodiment. The system includes a plurality of processors 1002 comprising 1002a-f that can access a shared memory subsystem 1004. The system incorporates a plurality of programmable hardware memory algorithm processors (MAPs) 1006a-f in the memory subsystem 1004. Each MAP 1006a-f can comprise a memory 1008a-f and one or more field programmable gate arrays (FPGAs) 1010a-f. The MAP provides a configurable functional unit and particular algorithms or portions of algorithms can be provided to the FPGAs 1010a-f for processing in close coordination with a respective processor. For example, the MAPs can be used to evaluate algebraic expressions regarding the data model and to perform adaptive data restructuring in example instances. In this example, each MAP is globally accessible by all of the processors for these purposes. In one configuration, each MAP can use Direct Memory Access (DMA) to access an associated memory 1008a-f, allowing it to execute tasks independently of, and asynchronously from the respective microprocessor 1002a-f. In this configuration, a MAP can feed results directly to another MAP for pipelining and parallel execution of algorithms.

The above computer architectures and systems are examples only, and a wide variety of other computer, cell phone, and personal data assistant architectures and systems can be used in connection with example instances, including systems using any combination of general processors, co-processors, FPGAs and other programmable logic devices, system on chips (SOCs), application specific integrated circuits (ASICs), and other processing and logic elements. In some instances, all or part of the computer system can be implemented in software or hardware. Any variety of data storage media can be used in connection with example instances, including random access memory, hard drives, flash memory, tape drives, disk arrays, Network Attached Storage (NAS) and other local or distributed data storage devices and systems.

In example instances, the computer system can be implemented using software modules executing on any of the above or other computer architectures and systems. In other instances, the functions of the system can be implemented partially or completely in firmware, programmable logic devices such as field programmable gate arrays (FPGAs) as referenced in FIG. 10, system on chips (SOCs), application specific integrated circuits (ASICs), or other processing and logic elements. For example, the Set Processor and Optimizer can be implemented with hardware acceleration through the use of a hardware accelerator card, such as accelerator card 722 illustrated in FIG. 7.

Other Embodiments

In some aspects, provided herein, is a method for synthesizing RNAs, comprising providing an RNA polymerase immobilized on a surface; and synthesizing a plurality of RNAs at a rate of extension of at least 50 nucleotides per hour, wherein each of the plurality of RNAs has a preselected sequence, and wherein the synthesizing comprises extending by a single base in an extension reaction. In some embodiments, each of the plurality of RNAs comprises a guide RNA (gRNA). In some embodiments, each of the plurality of RNAs is selected from the group consisting of a messenger RNA (mRNA), a small interfering RNA (siRNA), a short hairpin RNA (shRNA), a microRNA (miRNA), piwi-interacting RNA (piRNA), RNA aptamers, transfer RNA (tRNA), and antisense oligonucleotide (ASO). In some embodiments, the synthesizing is performed with a template DNA. In some embodiments, the template DNA is immobilized on the surface. In some embodiments, the template DNA is immobilized on the surface by a linker, a biotin, or a Streptavidin. In some embodiments, the template DNA comprises single-stranded DNA (ssDNA). In some embodiments, the template DNA comprises double-stranded DNA (dsDNA). In some embodiments, the template DNA comprises a secondary structure. In some embodiments, the secondary structure comprises a hairpin. In some embodiments, the template DNA comprises a promoter sequence. In some embodiments, the promoter sequence is a truncated promoter sequence. In some embodiments, the rate of extension is at least 50 nucleotides per minute. In some embodiments, the rate of extension is at least 50 nucleotides per second. In some embodiments, the RNA polymerase is selected from the group consisting of a phage RNA polymerase, a bacterial RNA polymerase, and a eukaryote RNA polymerase. In some embodiments, the RNA polymerase is immobilized on the surface by activating the surface with standard N-hydroxysuccinimide esters (NHS) functional group. In some embodiments, the RNA polymerase is immobilized on the surface by activating the surface with trifluoracetic anhydride (TFAA) functional group. In some embodiments, the RNA polymerase is immobilized on the surface by activating the surface with glutaraldehyde (GA) functional group. In some embodiments, the RNA polymerase is immobilized on the surface by a linker, a biotin, or a Streptavidin. In some embodiments, the surface is a solid surface. In some embodiments, the solid surface comprises a magnetic bead, an agarose bead, fused silica, sol-gel, silica polymer, silica monolith, cellulose, agar, acrylamide, a gold bead, or a gel matrix. In some embodiments, each of the plurality of RNAs has the same preselected sequence. In some embodiments, the plurality of RNAs comprises at least two RNAs comprising a different preselected sequence. In some embodiments, the plurality of RNAs comprises at least one gRNA with a chemical modification.

In some aspects, provided herein, is a method for synthesizing RNAs, comprising providing a fusion RNA polymerase or a functional fragment or a variant thereof and synthesizing a plurality of RNAs at a rate of extension of at least 50 nucleotides per hour, wherein each of the plurality of RNAs has a preselected sequence, and wherein the synthesizing comprises extending by a single base in an extension reaction. In some embodiments, the fusion RNA polymerase comprises an RNA polymerase or a functional fragment or a variant thereof and a DNA binding protein or a functional fragment or a variant thereof, wherein the RNA polymerase and the DNA binding protein are heterologous. In some embodiments, the fusion RNA polymerase further comprises a linker. In some embodiments, the RNA polymerase is selected from the group consisting of a phage RNA polymerase, a bacterial RNA polymerase, and a eukaryote RNA polymerase. In some embodiments, the DNA binding protein is fused to the N-terminus of the RNA polymerase. In some embodiments, the DNA binding protein is fused to the C-terminus of the RNA polymerase. In some embodiments, each of the plurality of RNAs comprises a guide RNA (gRNA). In some embodiments, each of the plurality of RNAs is selected from the group consisting of a messenger RNA (mRNA), a small interfering RNA (siRNA), a short hairpin RNA (shRNA), a microRNA (miRNA), piwi-interacting RNA (piRNA), RNA aptamers, transfer RNA (tRNA), and antisense oligonucleotide (ASO). In some embodiments, the synthesizing is performed with a template DNA. In some embodiments, the template DNA comprises single-stranded DNA (ssDNA). In some embodiments, the template DNA comprises double-stranded DNA (dsDNA). In some embodiments, the template DNA comprises a secondary structure. In some embodiments, the secondary structure comprises a hairpin. In some embodiments, the template DNA comprises a promoter sequence. In some embodiments, the promoter sequence is a truncated promoter sequence. In some embodiments, the rate of extension is at least 50 nucleotides per minute. In some embodiments, the rate of extension is at least 50 nucleotides per second. In some embodiments, each of the plurality of RNAs has the same preselected sequence. In some embodiments, the plurality of RNAs comprises at least two RNAs comprising a different preselected sequence. In some embodiments, the plurality of RNAs comprises at least one gRNA with a chemical modification.

In some aspects, provided herein, is a nucleic acid library, comprising a plurality of purified guide RNAs (gRNAs) and at least one single-stranded DNA (ssDNA) molecule encoding a truncated RNA polymerase promoter region. In some embodiments, each of the purified gRNAs comprises a sequence of at least 20 nucleotide in length. In some embodiments, each of the purified gRNAs comprises a sequence of at least 80 nucleotide in length. In some embodiments, the plurality of purified gRNAs comprises at least 100,000 purified gRNAs. In some embodiments, the truncated RNA polymerase promoter region comprises a sequence selected from the group consisting of SEQ ID NOs: 3-6. In some embodiments, the plurality of purified gRNAs comprises a modified nucleotide.

In some aspects, provided herein, is a nucleic acid library, comprising a plurality of purified guide RNAs (gRNAs) of at least 20 nucleotides in length; and at least one oligonucleotide of 2 to 10 nucleotides in length. In some embodiments, the plurality of purified guide RNAs (gRNAs) comprises at least 80 nucleotides in length. In some embodiments, the plurality of purified gRNAs comprises at least 100,000 purified gRNAs. In some embodiments, the at least one oligonucleotide is of 2, 3, 4, 5, 6, 7, 8, 9, or 10 nucleotides in length. In some embodiments, the at least one oligonucleotide comprises RNA. In some embodiments, the at least one oligonucleotide is 100% identical to 2, 3, 4, 5, 6, 7, 8, 9, or 10 consecutive nucleotides at or near the 5' end of a purified guide RNA. In some embodiments, the at least one oligonucleotide is 100% identical to 2, 3, 4, 5, 6, 7, 8, 9, or 10 consecutive nucleotides at or near the 3' end of a purified guide RNA.

In some embodiments, the plurality of purified gRNAs comprises at least one gRNA with a chemical modification. In some embodiments, the chemical modification comprises one or more 5' modifications selected from the group consisting of 5' triphosphate, 5' diphosphate, 5' mono-phosphate, and 5' hydroxyl. In some embodiments, the chemical modification comprises one or more ribose modifications selected from the group consisting of 2'-O-methylation (2'OMe), 2'-O-methoxy-ethyl (2'-MOE), 2'-fluoro (2'F), 2-deoxy-2'-thio, and 2'-azido. In some embodiments, the chemical modification comprises one or more internucleotide linkage modifications selected from the group consisting of phosphorothioate, methylphosphonate, phosphonocarboxylate, phosphonothiocarboxylate, boranophosphonate, alkylphosphonate, and alkylphosphonate. In some embodiments, the chemical modification comprises modified nucleotides comprising one or more heterocyclic modifications selected from the group consisting of 2,6-Diaminopurine, 2-Aminopurine, inosine, 2-aminoadenosine, N6-methyladenosine, N6,2'-O-dimethyladenosine, N1-methyladenosine, 2-amino-6-chloropurineriboside, 5-methylcytidine, 5-hydroxymethylcytidine, 8-oxo-7,8-dihydroguanosine, pseudouridine, N4-acetylcytidine, 5-bromo-uridine, 5-methyluridine, and 5-nitroindole. In some embodiments, the chemical modification comprises modified nucleotides comprising one or more 5' cap modifications selected from the group consisting of GpppG, 7-methylguanylate (m7GpppG), m2,2,7GpppG, and m7-3'-OGpppG (ARCA). In some embodiments, the chemical modification comprises modified nucleotides comprising one or more 5' cap modifications selected from the group consisting of an attachment chemistry, a dye, a cell targeting moiety, an active chemistry, and an amino modifier. In some embodiments, the attachment chemistry comprises biotin. In some embodiments, the dye comprises fluorescein. In some embodiments, the cell targeting moiety comprises digoxigenin. In some embodiments, the active chemistry comprises azides, acrydite, thiols, or alkynes. In some embodiments, the amino modifier comprises aminoallyl.

In some aspects, provided herein, is a method for making a nucleic acid library comprising at least 50 guide RNAs (gRNAs), the method comprising synthesizing at least 50 gRNAs using an RNA polymerase, wherein at least one of the at least 50 gRNAs comprises a spacer sequence complementary to a target sequence in a target gene, and wherein a 5' terminal nucleotide of the spacer sequence is complementary to a 3' terminal nucleotide of the target sequence. In some embodiments, each of the at least 50 gRNAs comprises a spacer sequence complementary to a target sequence in a target gene, and wherein a 5' terminal nucleotide of the spacer sequence is complementary to a 3' terminal nucleotide of the target sequence. In some embodiments, the RNA polymerase is selected from the group consisting of a phage RNA polymerase, a bacterial RNA polymerase, and a eukaryote RNA polymerase. In some embodiments, the RNA polymerase is a T7 RNA polymerase. In some embodiments, each of the at least 50 gRNAs exhibits enhanced editing efficiency of the target sequence compared to a gRNA comprising a 5' terminal nucleotide that is not complementary to a 3' terminal nucleotide of the target sequence. In some embodiments, each of the at least 50 gRNAs exhibits reduced off-target editing compared to a gRNA comprising a 5' terminal nucleotide that is not complementary to a 3' terminal nucleotide of the target sequence. In some embodiments, the at least 50 gRNAs comprise gRNA sequences lacking a 5' terminal guanine (G) nucleotide, wherein the gRNA sequences comprise at least 40 nucleotides in length, and wherein at least 3 consecutive nucleotides at the 5' terminus of the gRNA sequences are 100% identical to the 3' terminus of the target sequence in a genome. In some embodiments, each of the at least 50 gRNAs exhibits enhanced 5' terminal pairing with the target sequence compared to a gRNA comprising a gRNA sequence comprising a 5' terminal G nucleotide, wherein the 5' terminal G nucleotide is not present in the protospacer sequence. In some embodiments, each of the at least 50 gRNAs exhibits enhanced editing efficiency of a target sequence compared to a gRNA comprising a gRNA sequence comprising a spacer sequence, wherein the gRNA sequence comprises one or more G nucleotides at the 5' terminus of the spacer sequence, wherein the one or more G nucleotides at the 5' terminus of the spacer sequence are not complementary to one or more nucleotides at the 3' terminus of the target sequence in a genome. In some embodiments, each of the at least 50 gRNAs exhibits reduced off-target editing compared to a gRNA comprising a gRNA sequence comprising a spacer sequence, wherein the gRNA sequence comprises one or more G nucleotides at the 5' terminus of the spacer sequence, wherein the one or more G nucleotides at the 5' terminus of the spacer sequence are not complementary to one or more nucleotides at the 3' terminus of the target sequence in a genome. In some embodiments, the at least 50 gRNAs comprise gRNA sequences lacking a guanine (G) nucleotide in a 5' terminal codon, wherein the gRNA sequences comprise at least 40 nucleotides in length, and wherein at least 3 consecutive nucleotides at the 5' terminus of the gRNA sequences are 100% identical to the 3' terminus of the target sequence in a genome. In some embodiments, each of the at least 50 gRNAs exhibits enhanced 5' terminal pairing with the target sequence compared to a gRNA comprising a gRNA sequence comprising a G nucleotide in a 5' terminal codon, wherein the G nucleotide in the 5' terminal codon is not present in the protospacer sequence. In some embodiments, each of the at least 50 gRNAs exhibits enhanced editing efficiency of a target sequence compared to a gRNA comprising a gRNA sequence comprising a spacer sequence, wherein the gRNA sequence comprises one or more G nucleotides at the 5' terminus of the spacer sequence, wherein the one or more G nucleotides at the 5' terminus of the spacer sequence are not complementary to one or more nucleotides at the 3' terminus of the target sequence in a genome. In some embodiments, each of the at least 50 gRNAs exhibits reduced off-target editing compared to a gRNA comprising a gRNA sequence comprising a spacer sequence, wherein the gRNA sequence comprises one or more G nucleotides at the 5' terminus of the spacer sequence, wherein the one or more G nucleotides at the 5' terminus of the spacer sequence are not complementary to one or more nucleotides at the 3' terminus of the target sequence in a genome. In some embodiments, the at least 50 gRNAs comprise at least 100,000 purified gRNAs.

In some aspects, provided herein, is a nucleic acid library, comprising at least 50 purified guide RNAs (gRNAs), wherein the at least 50 purified gRNAs comprise gRNA sequences comprising a 5' terminal guanine (G) analog. In some embodiments, each of the at least 50 purified gRNAs exhibits enhanced editing efficiency of a target sequence compared to a gRNA comprising a gRNA sequence lacking a 5' terminal G analog. In some embodiments, each of the at least 50 purified gRNAs exhibits enhanced stability compared to a gRNA comprising a gRNA sequence lacking a 5' terminal G analog. In some embodiments, the at least 50 purified gRNAs comprise at least 100,000 purified gRNAs.

In some aspects, provided herein, is a nucleic acid library, wherein the nucleic acid library comprises at least 50 RNAs, wherein each of the at least 50 RNAs encodes a different guide RNA (gRNA) sequence, and wherein at least about 90% of the at least 50 RNAs are each present in the nucleic acid library in an amount within 1.5× of a mean frequency for the at least 50 RNAs in the library. In some embodiments, the nucleic acid library comprises at least 100, at least 500, at least 1,000, at least 5,000, at least 10,000, at least 50,000, or at least 100,000 RNAs, wherein at least about 90% of the at least 100, at least 500, at least 1,000, at least 5,000, at least 10,000, at least 50,000, or at least 100,000 RNAs are each present in the nucleic acid library in an amount within 1.5× of a mean frequency for the at least 100, at least 500, at least 1,000, at least 5,000, at least 10,000, at least 50,000, or at least 100,000 RNAs in the library. In some embodiments, the different gRNA sequence comprises at least 80 nucleotides in length. In some embodiments, the different gRNA sequence comprises at least 100 different gRNA sequences. In some embodiments, at least about 95% of the at least 50 RNAs are each present in the nucleic acid library in an amount within 1.5× of a mean frequency for each of the RNAs in the library. In some embodiments, at least about 99% of the at least 50 RNAs are each present in the nucleic acid library in an amount within 1.5× of a mean frequency for each of the RNAs in the library.

In some aspects, provided herein, is a modified polypeptide composition, wherein the modified polypeptide composition comprises a purified RNA polymerase or a functional fragment or a variant thereof and a purified nucleic acid binding protein, optionally a zinc finger containing protein, or a functional fragment or a variant thereof, wherein the purified RNA polymerase and the purified nucleic acid binding protein are heterologous, and wherein the purified RNA polymerase and the purified nucleic acid binding protein are linked. In some embodiments, the purified RNA polymerase and the purified nucleic acid binding protein are linked by conjugation. In some embodiments, the purified RNA polymerase and the purified nucleic acid binding protein are linked by fusion. In some embodiments, the purified nucleic acid binding protein is linked to the N-terminus of the purified RNA polymerase. In some embodiments, the purified nucleic acid binding protein is linked to the C-terminus of the purified RNA polymerase. In some embodiments, the purified RNA polymerase is a T7 RNA polymerase. In some embodiments, the purified nucleic acid binding protein comprises a zinc-finger domain, a leucine zipper, a helix-turn-helix (HTH) motif, a helix-loop-helix (HLH) motif, a winged helix (WH), a winged HTH (WHTH) motif, a high mobility group (HMG)-box, a White-Opaque Regulator 3 (Wor3) domain, an oligonucleotide/oligosaccharide-binding (OB)-fold domain, an immunoglobulin fold, a B3 domain, a Transcription Activator-Like Effector (TALE), a TALE-like protein, or a Clustered Regularly Interspaced Short Palindromic Repeats (CRISPR)-associated (Cas) protein. In some embodiments, the purified nucleic acid binding protein comprises a zinc finger domain.

In some aspects, provided herein, is a composition, comprising a fusion RNA polymerase or a functional fragment or a variant thereof, wherein the fusion RNA polymerase comprises (i) an RNA polymerase or a functional fragment or a variant thereof; and (ii) a DNA binding protein or a functional fragment or a variant thereof, wherein the RNA polymerase and the DNA binding protein are heterologous; and a DNA polynucleotide. In some embodiments, the DNA polynucleotide is a single-stranded DNA polynucleotide. In some embodiments, the DNA polynucleotide comprises a 3' secondary structure. In some embodiments, the 3' secondary structure comprises a hairpin.

In some aspects, provided herein, is a modified polypeptide, wherein the modified polypeptide comprises a variant T7 RNA polymerase or a functional fragment thereof, wherein the variant T7 RNA polymerase comprises at least four variations selected from the group consisting of K172L, P266L, H772R, N748X, R756M, Q758X, and E775V, wherein the position is determined by alignment with SEQ ID NO: 1, and wherein X is any amino acid different from the wild type amino acid. In some aspects, provided herein, is a modified polypeptide, wherein the modified polypeptide comprises a variant T7 RNA polymerase or a functional fragment thereof, wherein the variant T7 RNA polymerase comprises at least one variation selected from the group consisting of K172L, P266L, H772R, N748X, R756M, Q758X, and E775V, wherein the position is determined by alignment with SEQ ID NO: 1, wherein X is any amino acid different from the wild type amino acid, and wherein the modified poly-peptide is immobilized on a surface.

In some embodiments, the variant T7 RNA polymerase or the functional fragment thereof is linked to a DNA binding protein. In some embodiments, the variant T7 RNA polymerase or the functional fragment thereof is linked to the DNA binding protein by fusion. In some embodiments, the variant T7 RNA polymerase or the functional fragment thereof is linked to the DNA binding protein by conjugation. In some embodiments, the DNA binding protein is linked to the N-terminus of the T7 RNA polymerase. In some embodiments, the DNA binding protein is linked to the C-terminus of the T7 RNA polymerase. In some embodiments, the variant T7 RNA polymerase or the functional fragment thereof comprises a sequence that has at least 90% identity to SEQ ID NO: 1. In some embodiments, the variant T7 RNA polymerase or the functional fragment thereof exhibits increased stability during a transcription initiation and/or elongation process compared to a T7 RNA polymerase comprising a sequence according to SEQ ID NO: 1. In some embodiments, the variant T7 RNA polymerase or the functional fragment thereof exhibits reduced binding affinity to a T7 promoter sequence compared to a T7 RNA polymerase comprising a sequence according to SEQ ID NO: 1.

In some aspects, provided herein, is a device comprising a surface; a T7 RNA polymerase, or a functional fragment or a variant thereof; and a DNA template, wherein the DNA template comprises a truncated T7 promoter sequence; wherein the T7 RNA polymerase, a functional fragment or a variant thereof, or the DNA template is linked to the surface. In some embodiments, the device further comprises a nucleic acid binding protein, or a functional fragment or a variant thereof linked to the surface. In some embodiments, the surface is a solid surface. In some embodiments, the solid surface comprises a magnetic bead, an agarose bead, fused silica, sol-gel, silica polymer, silica monolith, cellulose, agar, acrylamide, or a gold bead. In some embodiments, the solid surface comprises a gel matrix for encapsulation or entrapment of the T7 RNA polymerase, the DNA template, or the nucleic acid binding protein. In some embodiments, the nucleic acid binding protein comprises a streptavidin tag. In some embodiments, the T7 RNA polymerase is immobilized. In some embodiments, the DNA template is immobilized. In some embodiments, the nucleic acid binding protein, or the functional fragment or the variant thereof comprises a zinc-finger domain, a leucine zipper, a helix-turn-helix (HTH) motif, a helix-loop-helix (HLH) motif, a winged helix (WH), a winged HTH (WHTH) motif, a high mobility group (HMG)-box, a White-Opaque Regulator 3 (Wor3) domain, an oligonucleotide/oligosaccharide-binding (OB)-fold domain, an immunoglobulin fold, a B3 domain, a Transcription Activator-Like Effector (TALE), a TALE-like protein, or a Clustered Regularly Inter-spaced Short Palindromic Repeats (CRISPR)-associated (Cas) protein. In some embodiments, the nucleic acid binding protein, or the functional fragment or the variant thereof binds to a nucleic acid through sequence specific binding. In some embodiments, the nucleic acid binding protein, or the functional fragment or the variant thereof binds to a nucleic acid through one or more chemical modifications on the nucleic acid. In some embodiments, the one or more chemical modifications comprise a biotin or an avidin. In some embodiments, the DNA binding protein comprises a zinc-finger domain, a leu-cine zipper, a helix-turn-helix (HTH) motif, a helix-loop-helix (HLH) motif, a winged helix (WH), a winged HTH (WHTH) motif, a high mobility group (HMG)-box, a White-Opaque Regulator 3 (Wor3) domain, an oligonucleotide/oligosaccharide-binding (OB)-fold domain, an immunoglobulin fold, a B3 domain, a Transcription Activator-Like Effector (TALE), a TALE-like protein, or a Clustered Regularly Interspaced Short Palindromic Repeats (CRISPR)-associated (Cas) protein. In some embodiments, the DNA template comprises a sequence comprising SEQ ID NO: 7. In some embodiments, the T7 RNA polymerase or the variant thereof comprises a sequence that has at least 90% identity to SEQ ID NO: 1. In some embodiments, the device further comprises a piezoelectric vibrator, a turning valve, a Peltier heater, a voltage controller, a syringe pump, a UV LED and sensor, or a vacuum pump.

```
Sequences
(WT T7 RNA polymerase protein sequence)
                                                          SEQ ID NO: 1
MNTINIAKNDFSDIELAAIPFNTLADHYGERLAREQLALEHESYEMGEARFRKMFERQLKAGEVADN

AAAKPLITTLLPKMIARINDWFEEVKAKRGKRPTAFQFLQEIKPEAVAYITIKTTLACLTSADNTTV

QAVASAIGRAIEDEARFGRIRDLEAKHFKKNVEEQLNKRVGHVYKKAFMQVVEADMLSKGLLGGEAW

SSWHKEDSIHVGVRCIEMLIESTGMVSLHRQNAGVVGQDSETIELAPEYAEAIATRAGALAGISPMF
```

-continued

QPCVVPPKPWTGITGGGYWANGRRPLALVRTHSKKALMRYEDVYMPEVYKAINIAQNTAWKINKKVL
AVANVITKWKHCPVEDIPAIEREELPMKPEDIDMNPEALTAWKRAAAAVYRKDKARKSRRISLEFML
EQANKFANHKAIWFPYNMDWRGRVYAVSMFNPQGNDMTKGLLTLAKGKPIGKEGYYWLKIHGANCAG
VDKVPFPERIKFIEENHENIMACAKSPLENTWWAEQDSPFCFLAFCFEYAGVQHHGLSYNCSLPLAF
DGSCSGIQHFSAMLRDEVGGRAVNLLPSETVQDIYGIVAKKVNEILQADAINGTDNEVVTVTDENTG
EISEKVKLGTKALAGQWLAYGVTRSVTKRSVMTLAYGSKEFGFRQQVLEDTIQPAIDSGKGLMFTQP
NQAAGYMAKLIWESVSVTVVAAVEAMNWLKSAAKLLAAEVKDKKTGEILRKRCAVHWVTPDGFPVWQ
EYKKPIQTRLNLMFLGQFRLQPTINTNKDSEIDAHKQESGIAPNFVHSQDGSHLRKTVVWAHEKYGI
ESFALIHDSFGT IPADAANLFKAVRETMVDTYESCDVLADFYDQFADQLHESQLDKMPALPAKGNLN
LRDILESDFAFA (WT T7 RNA polymerase DNA sequence)
SEQ ID NO: 2

ATGAACACGATTAACATCGCTAAGAACGACTTCTCTGACATCGAACTGGCTGCTATCCCGTTCAACA
CTCTGGCTGACCATTACGGTGAGCGTTTAGCTCGCGAACAGTTGGCCCTTGAGCATGAGTCTTACGA
GATGGGTGAAGCACGCTTCCGCAAGATGTTTGAGCGTCAACTTAAAGCTGGTGAGGTTGCGGATAAC
GCTGCCGCCAAGCCTCTCATCACTACCCTACTCCCTAAGATGATTGCACGCATCAACGACTGGTTTG
AGGAAGTGAAAGCTAAGCGCGGCAAGCGCCCGACAGCCTTCCAGTTCCTGCAAGAAATCAAGCCGGA
AGCCGTAGCGTACATCACCATTAAGACCACTCTGGCTTGCCTAACCAGTGCTGACAATACAACCGTT
CAGGCTGTAGCAAGCGCAATCGGTCGGGCCATTGAGGACGAGGCTCGCTTCGGTCGTATCCGTGACC
TTGAAGCTAAGCACTTCAAGAAAAACGTTGAGGAACAACTCAACAAGCGCGTAGGGCACGTCTACAA
GAAAGCATTTATGCAAGTTGTCGAGGCTGACATGCTCTCTAAGGGTCTACTCGGTGGCGAGGCGTGG
TCTTCGTGGCATAAGGAAGACTCTATTCATGTAGGAGTACGCTGCATCGAGATGCTCATTGAGTCAA
CCGGAATGGTTAGCTTACACCGCCAAAATGCTGGCGTAGTAGGTCAAGACTCTGAGACTATCGAACT
CGCACCTGAATACGCTGAGGCTATCGCAACCCGTGCAGGTGCGCTGGCTGGCATCTCTCCGATGTTC
CAACCTTGCGTAGTTCCTCCTAAGCCGTGGACTGGCATTACTGGTGGTGGCTATTGGGCTAACGGTC
GTCGTCCTCTGGCGCTGGTGCGTACTCACAGTAAGAAAGCACTGATGCGCTACGAAGACGTTTACAT
GCCTGAGGTGTACAAAGCGATTAACATTGCGCAAAACACCGCATGGAAAATCAACAAGAAAGTCCTA
GCGGTCGCCAACGTAATCACCAAGTGGAAGCATTGTCCGGTCGAGGACATCCCTGCGATTGAGCGTG
AAGAACTCCCCGATGAAACCGGAAGACATCGACATGAATCCTGAGGCTCTCACCGCGTGGAAACGTGC
TGCCGCTGCTGTGTACCGCAAGGACAAGGCTCGCAAGTCTCGCCGTATCAGCCTTGAGTTCATGCTT
GAGCAAGCCAATAAGTTTGCTAACCATAAGGCCATCTGGTTCCCTTACAACATGGACTGGCGCGGTC
GTGTTTACGCTGTGTCAATGTTCAACCCGCAAGGTAACGATATGACCAAAGGACTGCTTACGCTGGC
GAAAGGTAAACCAATCGGTAAGGAAGGTTACTACTGGCTGAAAATCCACGGTGCAAACTGTGCGGGT
GTCGATAAGGTTCCGTTCCCTGAGCGCATCAAGTTCATTGAGGAAAACCACGAGAACATCATGGCTT
GCGCTAAGTCTCCACTGGAGAACACTTGGTGGGCTGAGCAAGATTCTCCGTTCTGCTTCCTTGCGTT
CTGCTTTGAGTACGCTGGGGTACAGCACCACGGCCTGAGCTATAACTGCTCCCTTCCGCTGGCGTTT
GACGGGTCTTGCTCTGGCATCCAGCACTTCTCCGCGATGCTCCGAGATGAGGTAGGTGGTCGCGCGG
TTAACTTGCTTCCTAGTGAAACCGTTCAGGACATCTACGGGATTGTTGCTAAGAAAGTCAACGAGAT
TCTACAAGCAGACGCAATCAATGGGACCGATAACGAAGTAGTTACCGTGACCGATGAGAACACTGGT
GAAATCTCTGAGAAAGTCAAGCTGGGCACTAAGGCACTGGCTGGTCAATGGCTGGCTTACGGTGTTA
CTCGCAGTGTGACTAAGCGTTCAGTCATGACGCTGGCTTACGGGTCCAAAGAGTTCGGCTTCCGTCA

-continued

ACAAGTGCTGGAAGATACCATTCAGCCAGCTATTGATTCCGGCAAGGGTCTGATGTTCACTCAGCCG

AATCAGGCTGCTGGATACATGGCTAAGCTGATTTGGGAATCTGTGAGCGTGACGGTGGTAGCTGCGG

TTGAAGCAATGAACTGGCTTAAGTCTGCTGCTAAGCTGCTGGCTGCTGAGGTCAAAGATAAGAAGAC

TGGAGAGATTCTTCGCAAGCGTTGCGCTGTGCATTGGGTAACTCCTGATGGTTTCCCTGTGTGGCAG

GAATACAAGAAGCCTATTCAGACGCGCTTGAACCTGATGTTCCTCGGTCAGTTCCGCTTACAGCCTA

CCATTAACACCAACAAAGATAGCGAGATTGATGCACACAAACAGGAGTCTGGTATCGCTCCTAACTT

TGTACACAGCCAAGACGGTAGCCACCTTCGTAAGACTGTAGTGTGGGCACACGAGAAGTACGGAATC

GAATCTTTTGCACTGATTCACGACTCCTTCGGTACCATTCCGGCTGACGCTGCGAACCTGTTCAAAG

CAGTGCGCGAAACTATGGTTGACACATATGAGTCTTGTGATGTACTGGCTGATTTCTACGACCAGTT

CGCTGACCAGTTGCACGAGTCTCAATTGGACAAAATGCCAGCACTTCCGGCTAAAGGTAACTTGAAC

CTCCGTGACATCTTAGAGTCGGACTTCGCGTTCGCG (T7 RNA polymerase promoter sequence)
SEQ ID NO: 3
TTAAATTAATACGACTCACTATATATA (truncated T7 RNA polymerase promoter sequence)
SEQ ID NO: 4
TACGACTCACTATA (truncated T7 RNA polymerase promoter sequence)
SEQ ID NO: 5
AATACGACTCACTATA (truncated T7 RNA polymerase promoter sequence)
SEQ ID NO: 6
TTAATACGACTCACTATA (hairpin, full length (5'-3') template)
SEQ ID NO: 7
TATAGTGAGTCGTATTAATTTACAACAAAATTAATACGACTCA (ZFA)
SEQ ID NO: 8
NLISLFSGAGGLDLGFQKAGFRIICANEYDKSIWKTYESNHSAKLIKGDISKISSDEFPKCDGIIGG

PPCQSWSEGGSLRGIDDPRGKLFYEYIRILKQKKPIFFLAENVKGMMAQRHNKAVQEFIQEFDNAGY

DVHIILLNANDYGVAQDRKRVFYIGFRKELNINYLPPIPHLIKPTFKDVIWDLKDNPIPALDKNKTN

GNKCIYPNHEYFIGSYSTIFMSRNRVRQWNEPAFTVQASGRQCQLHPQAPVMLKVSKNLNKFVEGKE

HLYRRLTVRECARVQGFPDDFIFHYESLNDGYKMIGNAVPVNLAYEIAKTIKSALEICKGN (Rhizavidin, a monomeric Streptavidin)
SEQ ID NO: 9
FDASNFKDFSSIASASSSWQNQHGSTMIIQVDSFGNVSGQYVNRAEGTGCQNSPYPLTGRVNGTFID

FSVKWNNSTENCNSNTQWTGYAQVNGNNTEIVTRWNLKYEGGSGPAIWQGQDTFQYVPTTE (linker 1)
SEQ ID NO: 10
GSGGGGSGGGGSGGGGS (linker 2)
SEQ ID NO: 11
GSGGGGSGGGGS (linker 3)
SEQ ID NO: 12
GSGGGGSGGGGSGGGGSGGGGS (XTEN linker)
SEQ ID NO: 13
SGSETPGTSESATPES

EXAMPLES

These examples are provided for illustrative purposes only and not to limit the scope of the claims provided herein.

Example 1

Figure 11:
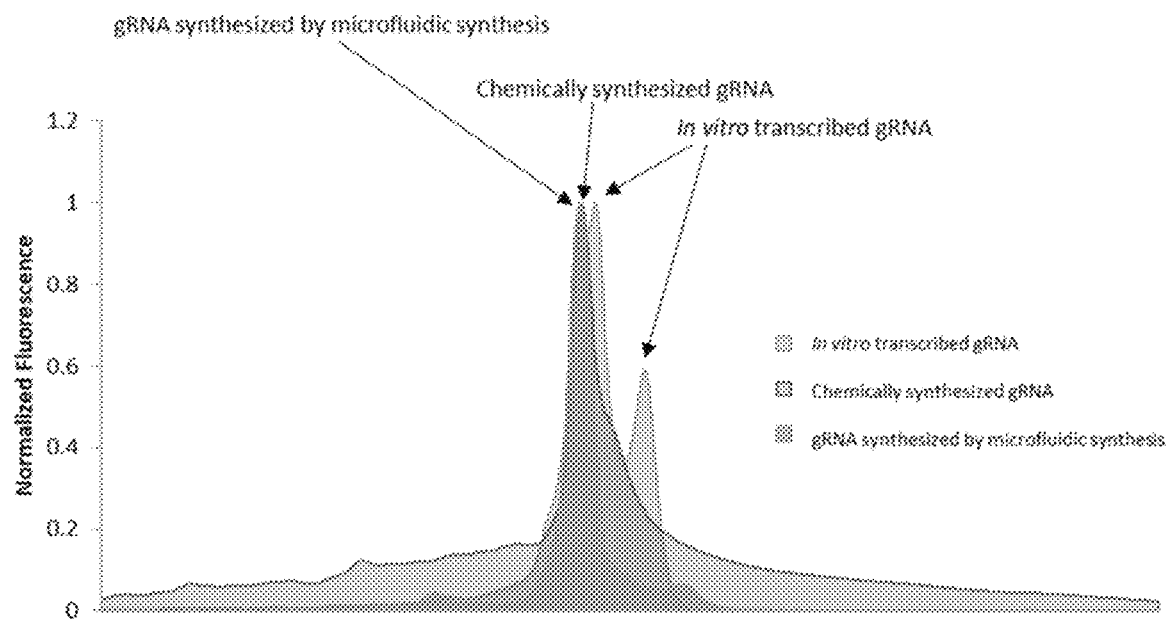
FIG. 11 depicts a plot comparing the purity of guide RNAs (gRNAs). Each graph represents gRNAs produced by microfluidic polynucleotide synthesis methods (orange), gRNAs produced by chemical synthesis (blue), or gRNAs produced by in vitro transcription (green). X-axis is elution time and Y-axis is normalized fluorescence units.
Figure 12:
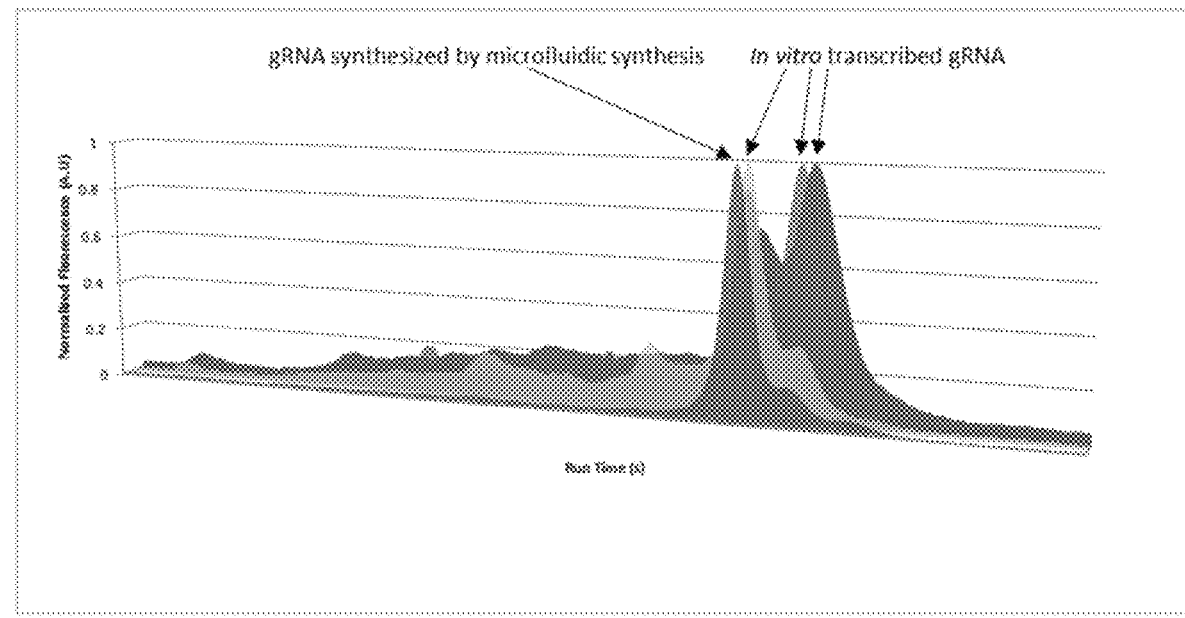
FIG. 12 depicts a plot comparing the purity of gRNAs. Each graph represents gRNAs produced by microfluidic polynucleotide synthesis methods (blue) or gRNAs produced by three different in vitro transcription (IVT) kits (green, red, and purple). X-axis is run time (seconds) and Y-axis is normalized fluorescence units.
Figure 13:
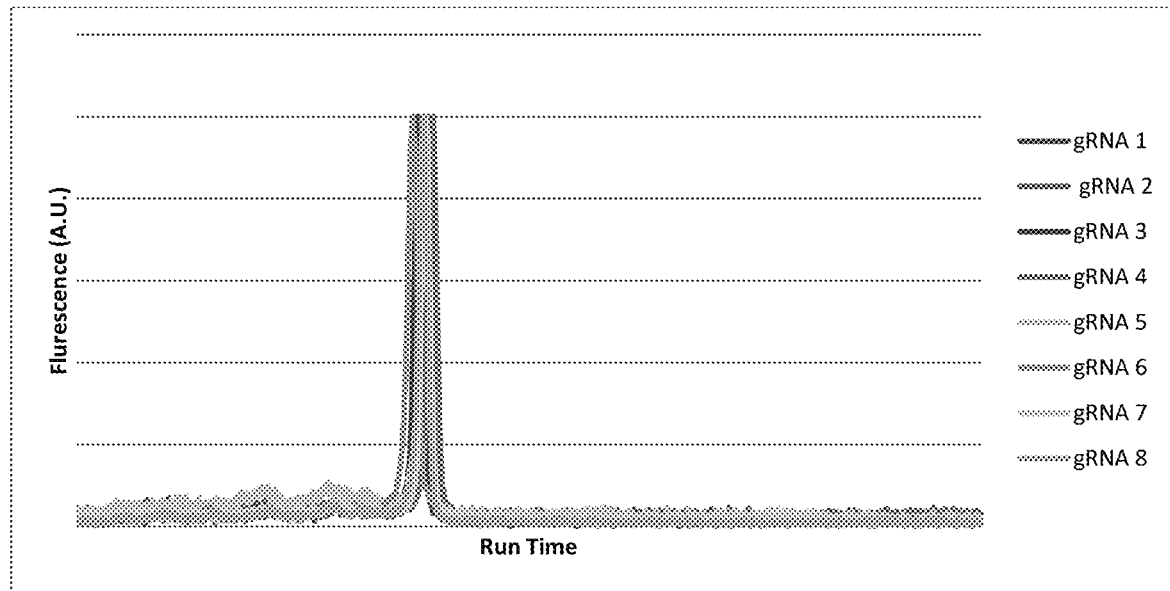
FIG. 13 depicts a plot comparing the purity of gRNAs. Each graph represents eight different gRNA samples produced by microfluidic polynucleotide synthesis methods. X-axis is run time (seconds) and Y-axis is normalized fluorescence units.

RNA Purification using Capillary Electrophoresis gRNAs were produced by in vitro transcription using a hairpin single-stranded DNA (ssDNA) template and assessed for purity using Capillary electrophoresis (CE). The microfluidic LabChip® capillary electrophoresis technology (PerkinElmer) was used according to the standard protocol (Small RNA Assay User Guide, 2020, PerkinElmer). CE analysis was used to compare the quality of gRNAs (see FIG. 11) that were in vitro transcribed (green), chemically synthesized (blue), and synthesized using microfluidic polynucleotide synthesis methods (orange). Peak amplitude represents nominal significance and a single cleanly resolved peak with little peak broadening is indicative of purity of gRNAs (FIG. 11, orange). Broader spectrum tails or multiple peaks are indicative of impurity (e.g., multiple gRNA products of different sizes) and low quality of gRNAs (FIG. 11, green and blue). The results of CE analysis comparing the quality of gRNAs synthesized using microfluidic polynucleotide synthesis methods (blue) to gRNAs synthesized by different in vitro transcription methods (green, red, and purple) are shown in FIG. 12. In addition, the quality of 8 different gRNA samples was compared using CE analysis (Table 1 and FIG. 13), which demonstrates that the high purity can be reproduced. As can be seen in Table 1, e.g., gRNAs about 100 nucleotides in length analyzed by CE have 100% purity.

TABLE 1 gRNA purity

| gRNA Sample Name | Size (base pair) | Concentration (ng/ul) | % Purity |
|---|---|---|---|
| 1 | 98 | 0.186684 | 100 |
| 2 | 97 | 0.205437 | 100 |
| 3 | 99 | 0.177009 | 100 |
| 4 | 95 | 0.311856 | 100 |
| 5 | 100 | 0.181547 | 100 |
| 6 | 96 | 0.163324 | 100 |
| 7 | 93 | 0.387597 | 100 |
| 8 | 98 | 0.253604 | 100 |

Example 2 gRNA Editing Efficiency

Cleavage Assay

Figure 14:
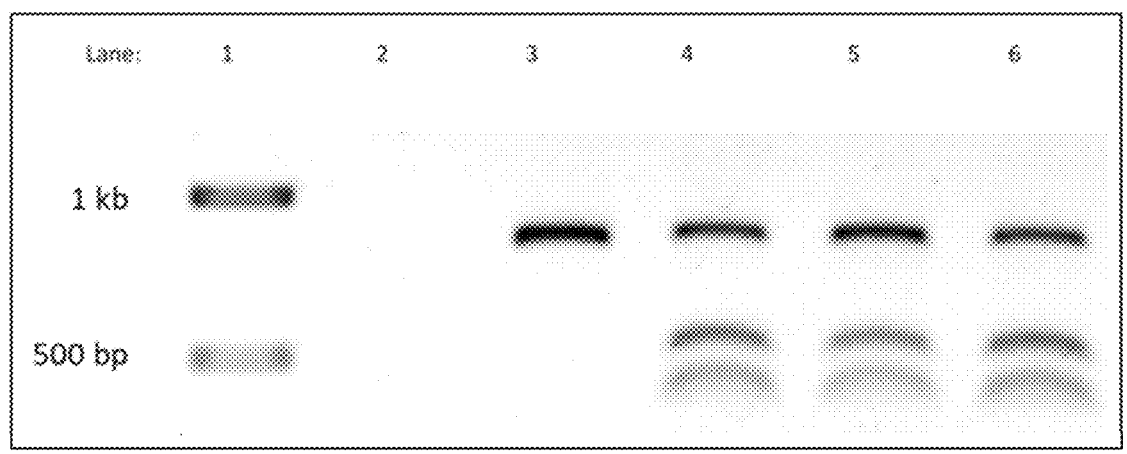
FIG. 14 depicts a DNA agarose gel electrophoresis analysis of an in vitro cleavage assay for CRISPR-Cas9 mediated cleavage of a target DNA at different time points. Lane 1: ladder, lane 2: blank, lane 3: gRNA produced by in vitro transcription using a hairpin DNA template taken at 0 minute, lane 4: commercially available in vitro transcribed gRNA 1 taken at 5 minutes, lane 5: commercially available chemically synthesized gRNA 2 taken at 5 minutes, lane 6: gRNA produced by in vitro transcription using a hairpin single-stranded DNA template taken at 5 minutes.

In vitro cleavage assay was performed to compare the nuclease activity of the *S. pyogenes* Cas9 on the DNA substrate comprising the target sequence using differently sourced gRNAs. Reaction mixture was prepared by mixing nuclease-free water, buffer, 300 nM gRNA, and 1 µM Cas9. 30 nM substrate DNA was added to the reaction mixture, which was then mixed and pulse-spun in a microfuge. A sample was taken out for 0 minute (FIG. 14, lane 3) and the rest of the reaction mixture was incubated at 37° C. for 5 minutes (FIG. 14, lanes 4-6). 1 µl of Proteinase K was added to each sample and mixed thoroughly. Samples were pulse-spun in a microfuge and incubated at room temperature for 10 minutes before proceeding with fragment analysis. As shown in FIG. 14, a 1 kb target DNA sequence was cleaved into two smaller (~500 bp) fragments by Cas9 with commercially available, in vitro transcribed or chemically synthesized gRNAs (lanes 4 and 5, respectively) and gRNA synthesized using a hairpin ssDNA template in vitro (lane 6).

In Vivo Nuclease Activity

Figure 15A:
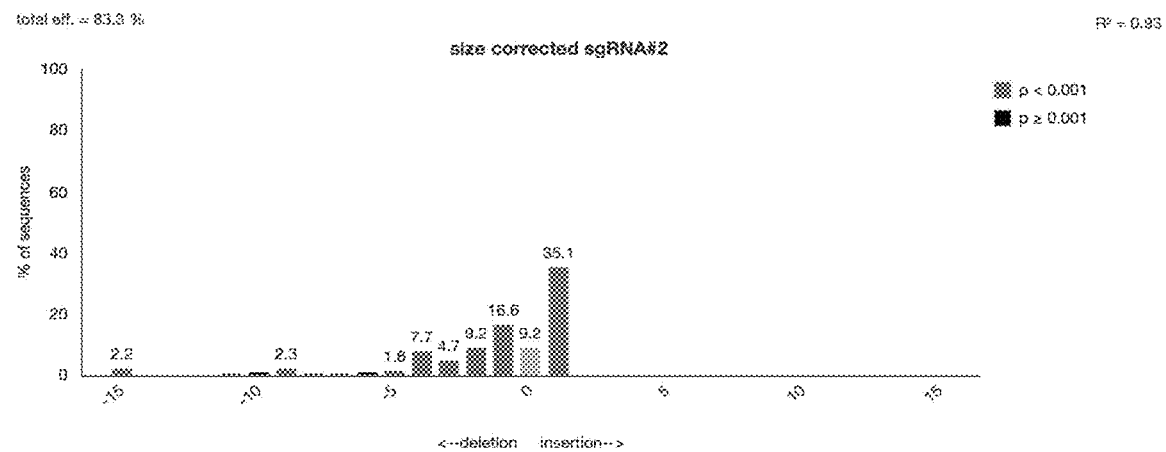
FIG. 15A depicts a tracking of indels by decomposition (TIDE) analysis for single guide RNA (sgRNA) showing spectrum of insertions and/or deletions (indels) and their frequencies. X-axis shows spectrum of indels and Y-axis is percentage (%) of sequences. Shown on the top left corner is total efficiency of editing (%) and shown on the top right corner is coefficient of determination ($r^2$).
Figure 15B:
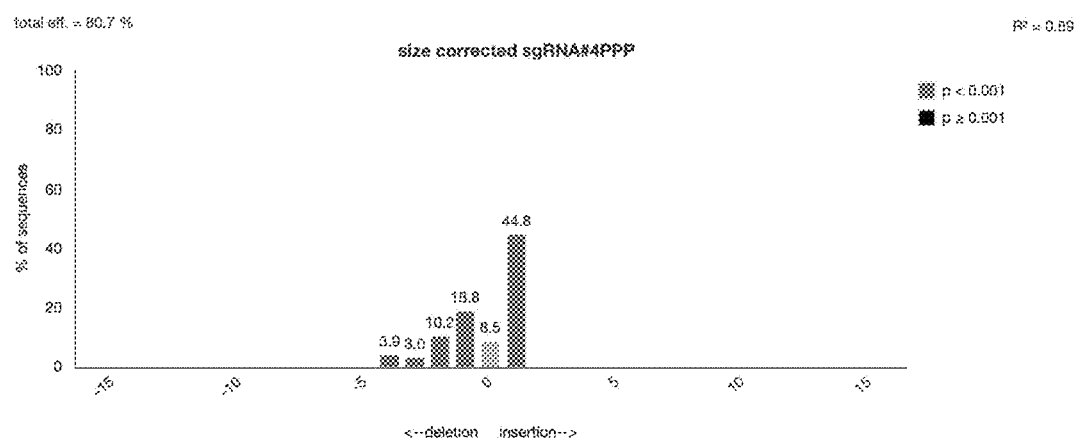
FIG. 15B depicts a tracking of indels by decomposition (TIDE) analysis for sgRNA showing spectrum of indels and their frequencies. X-axis shows spectrum of indels and Y-axis is percentage (%) of sequences. Shown on the top left corner is total efficiency of editing (%) and shown on the top right corner is coefficient of determination ($r^2$).

In vivo CRISPR-Cas9 mediated nuclease assay was performed according to the standard protocol (User Guide, Alt-R CRISPR-Cas9 System: Cationic lipid delivery of CRISPR ribonucleoprotein complexes into mammalian cells, Version 4, 2018, Integrated DNA Technologies and User Guide, Alt-R CRISPR-Cas9 System: Delivery of ribonucleoprotein complexes into HEK-293 cells using the Amaxa® Nucleofector® System, Version 3.1, 2019, Integrated DNA Technologies) to measure the efficacy of gRNA for Cas9 nuclease activity on a target DNA using two different single guide RNAs (sgRNAs). Briefly, the HEK-293 cells were freshly thawed and sub-cultured for a minimum of 2-3 days before electroporation while maintaining confluency to ≤90%. The Cas9 and sgRNAs were diluted in PBS and incubated at room temperature for 10-20 minutes for ribonucleoprotein (RNP) complex formation. The RNP complex was electroporated into the HEK-293 cells. The efficacy and the mutation spectrum were analyzed using Tracking of Indels (insertions and deletions) by Decomposition (TIDE) analysis, which quantifies the editing efficacy while simultaneously identifying the predominant types of indels in the targeted population of cells. TIDE analysis involves three simple steps using standard molecular biology reagents for PCR reactions: 1. One pair of standard PCR reactions, 2. One pair of standard capillary ("Sanger") sequencing reactions, and 3. Analysis of the two resulting raw sequencing files using the TIDE web tool. The TIDE web tool accurately reconstructs the spectrum of indels from the sequence traces using an algorithm and reports the identity of the detected indels and their frequencies. Both sgRNAs that were tested showed >80% editing efficiency as shown in FIGS. 15A and 15B (top left corner).

Example 3

Microfluidics Integration of RNA Synthesis

A microfluidic cartridge is designed to implement guide RNA (gRNA) synthesis and purification. Each microfluidic cartridge contains multiple reaction chambers and each reaction chamber can produce gRNAs with the same sequence or different sequences. The transcription complex including DNA templates and RNA polymerase enzymes are immobilized on the surface such as beads inside the reaction chamber using surface chemistry. The surface (e.g., beads such as magnetic beads) of each reaction chamber is functionalized using standard N-hydroxysuccinimide esters (NHS) reaction chemistry to support the attachment and synthesis of RNA. DNA binding proteins (e.g., strep, etc.) are added, and NHS reaction is then quenched. T7 RNA polymerases are added to bind the DNA binding proteins to form a stable complex. DNA template is added and is bound to the complex through binding to DNA binding protein.

A pneumatic peristaltic pumping system can be utilized for programmable fluid manipulation. Mixed bases and other transcription reagents are introduced to the reaction chamber through the fluid inlets. High purity RNA products are produced as the enzyme catalyze the reaction.

Example 4

RNA Synthesis

DNA templates, such as single-stranded DNA (ssDNA), are added to each reaction chamber of the microfluidic cartridge. Transcription reaction reagents including mixed RNA bases, optionally initiator and/or terminator oligonucleotides, are then injected to reaction chambers through the fluid inlets and flowed over the transcription complexes immobilized on the surface. A thermoelectric Peltier element heater is utilized to keep the temperature of the reaction chamber to 37° C. RNAs are produced and removed from reaction chambers in the order of seconds as controlled by the flow rate.

Example 5

RNA Purification using Isotachophoresis

Isotachophoresis (ITP) can be used for RNA purification according to Han, et al. (Lab Chip, 2019,19, 2741-2749). ITP is a robust electrophoretic separation and preconcentration technique that generates strong electric field gradients and enables selective focusing and separation of charged species based on their electrophoretic mobilities. ITP electrolyte chemistry can be controlled to purify RNA within the target size range.

Example 6

RNA Production by Fusion Enzyme and Promoter with Enzyme Binding Domain

Figure 16A:
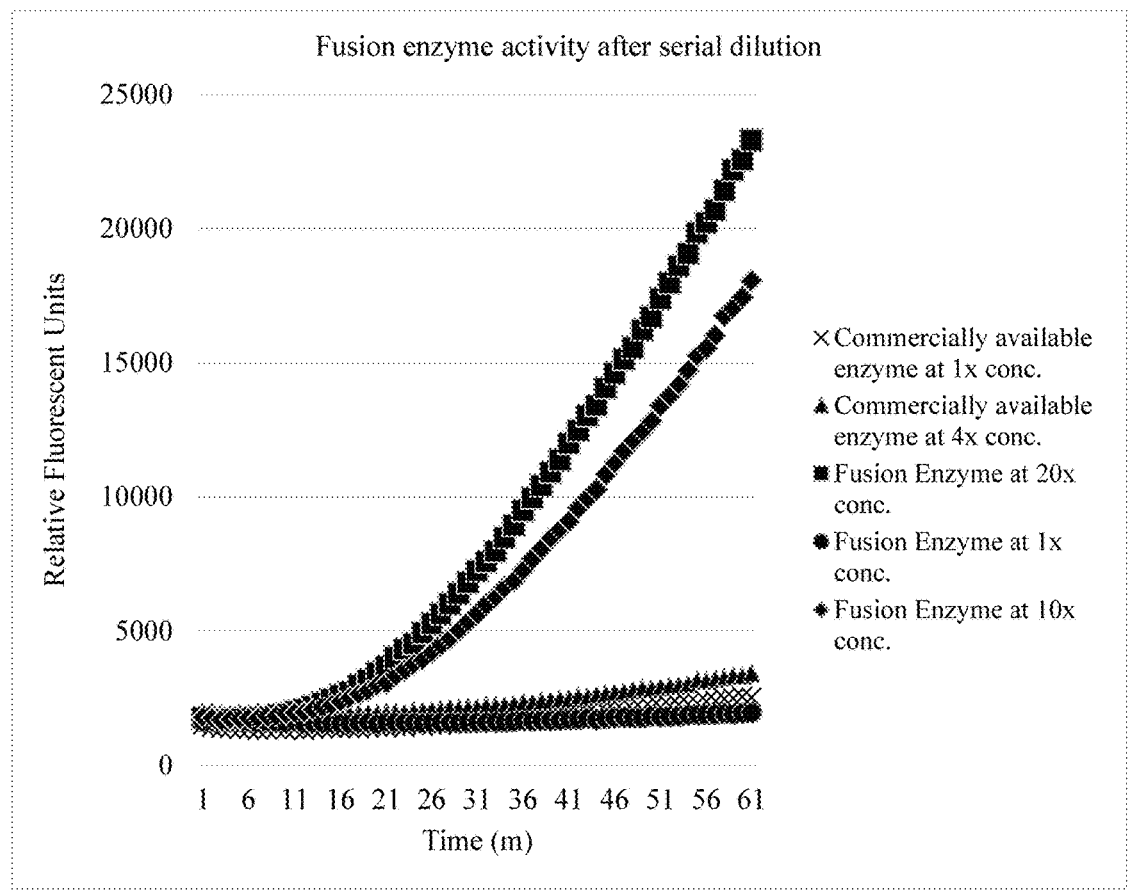
FIG. 16A depicts a plot of real time measurement of ribonucleotide transcriptional output comparing enzyme activity of a commercially available enzyme and a fusion enzyme containing a RNA polymerase domain and DNA binding domain. X-axis shows Time and Y-axis shows fluorescent readings in Relative Fluorescent Units (RFU).
Figure 16B:
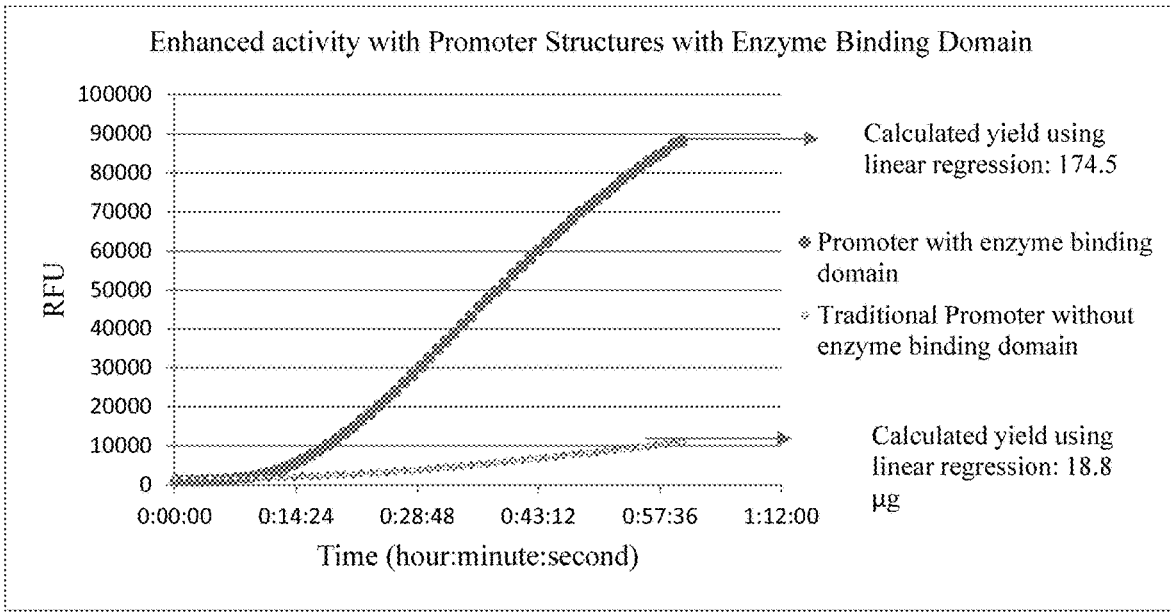
FIG. 16B depicts a plot of real time measurement of ribonucleotide transcriptional output. X-axis shows Time and Y-axis shows fluorescent readings in Relative Fluorescent Units (RFU).

T7 RNA polymerization activity assay was developed based on complex formation of DNA-transcribed RNA product and its fluorescent aptamer such as Broccoli-DFHBI-1T. Due to the fluorometric nature, this assay allows measuring RNA transcription products in a real-time manner. The double-stranded DNA (dsDNA) substrate was produced using an annealing protocol where equal molar amounts of template and non-template strands were mixed and heated for 2 minutes at 94° C. in a thermocycler before the mixture was cooled down. A continuous assay was initiated by adding T7 RNA polymerase enzyme into 20 µl of the reaction mixture containing 100 µM DFHBI-1T, 400 nM dsDNA Broccoli template (for fluorescence), 4 mM NTPs, 0.1 U inorganic pyrophosphatase and 1× transcription buffer. The reaction mixture was incubated for up to 1 hour at 37° C. while the enzyme activity was measured at 37° C. by fluorescence reads (excitation wavelength of 469 nm and emission wavelength of 501 nm) using Cytation 5 imaging reader (Biotek). The commercial T7 RNA polymerase was replaced with a fusion enzyme containing RNA polymerase and DNA binding domain described herein (e.g., Rhizavidin) to compare RNA production activity (FIG. 16A). In addition, promoter structures with enzyme binding domain were tested to compare RNA production activity with traditional promoters without enzyme binding domain (FIG. 16B).

Example 7

Stronger Promoter Binding Compared to Commercial RNA Polymerase

Figure 17A:
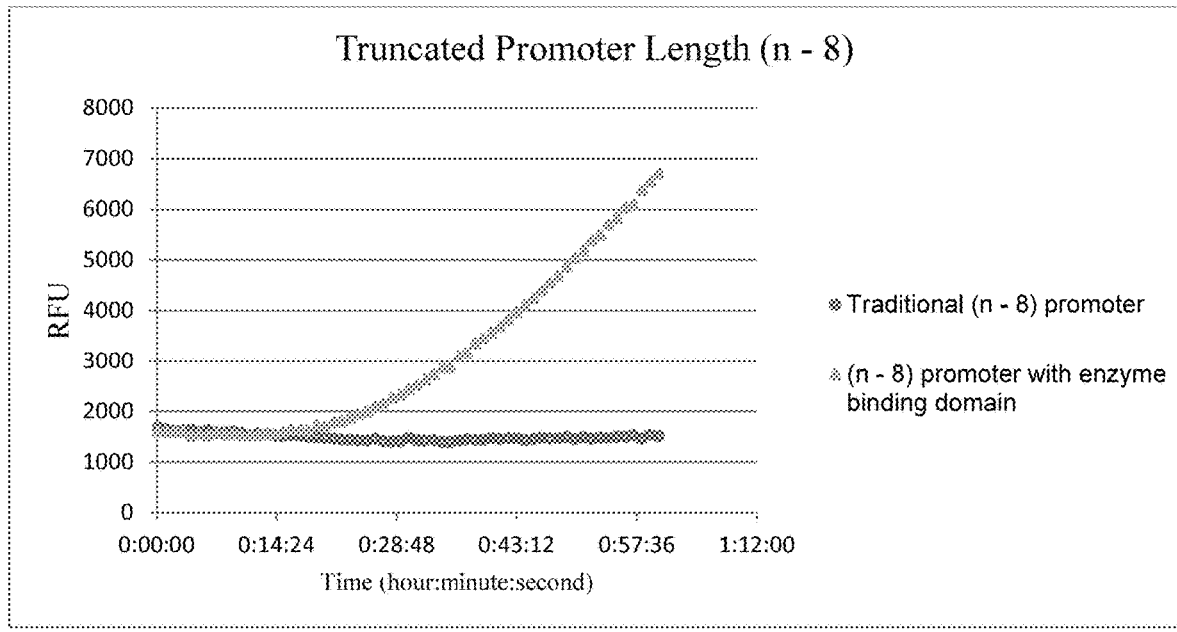
FIG. 17A depicts a plot of real time measurement of ribonucleotide transcriptional output. X-axis shows Time and Y-axis shows fluorescent readings in Relative Fluorescent Units (RFU).
Figure 17B:
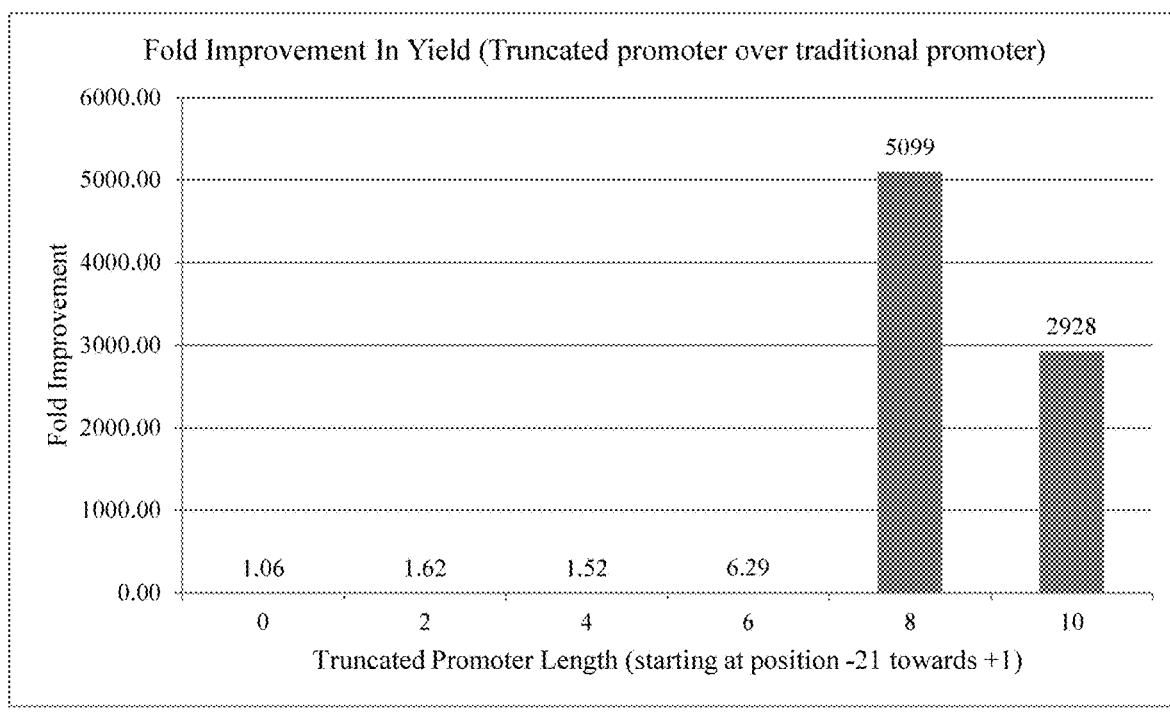
FIG. 17B depicts a plot of improvement in RNA yield comparing truncated and traditional promoters. X-axis shows the length of truncated promoter and Y-axis shows fold improvement.

To interrogate how T7 promoter sequence affects RNA polymerization activity, a series of Broccoli dsDNA substrates were synthesized with 0-10 upstream sequence deletion of the non-essential promoter region. To further dissect whether additional substrate binding to T7 RNA polymerase enzyme would make synergistic effect on promoter escape as well as facilitate RNA synthesis, DNA substrates conjugated with biotin at the 5' of the non-template strand in each pair were prepared. The real-time RNA polymerization assays were initiated by adding a fusion enzyme containing RNA polymerase and DNA binding domain described herein (e.g., Rhizavidin) into 20 µl of the reaction mixture containing 100 µM DFHBI-1T, 400 nM truncated dsDNA Broccoli templates, 4 mM NTPs, 0.1 U inorganic pyrophosphatase and 1× transcription buffer. The reaction mixture was incubated for up to 1 hour at 37° C. and the enzyme activity was measured by the same method described in Example 6. The sequences of Broccoli, essential T7 promoter, and non-essential T7 promoter are shown below:

(Broccoli sequence)
SEQ ID NO: 14
GAGCCCACACTCTACTCGACAGATACGAATATCTGGACCCGACCGTCTC (essential T7 promoter)
SEQ ID NO: 15
TATAGTGAGTC (non-essential T7 promoter)
SEQ ID NO: 16
GTATTAATTT The sequences of DNA templates are shown in Table 2. The results are shown in FIGS. 17A-17B.

TABLE 2

| | Sequences of DNA templates |
|---|---|
| DNA template | Sequence from 5' to 3' direction (5'biotin-Broccoli-promoter-3') |
| Full length (SEQ ID NO: 17) | AAGAGCCCACACTCTACTCGACAGATACGAATATCTGGACCCGACCGTCT CGATCCTATAGTGAGTCTATAGTGAGTCGTATTAATTT |
| N-2 (SEQ ID NO: 18) | AAGAGCCCACACTCTACTCGACAGATACGAATATCTGGACCCGACCGTCT CGATCCTATAGTGAGTCTATAGTGAGTCGTATTAAT*GG* |
| N-4 (SEQ ID NO: 19) | AAGAGCCCACACTCTACTCGACAGATACGAATATCTGGACCCGACCGTCT CGATCCTATAGTGAGTCTATAGTGAGTCGTATTA*GGCT* |
| N-6 (SEQ ID NO: 20) | AAGAGCCCACACTCTACTCGACAGATACGAATATCTGGACCCGACCGTCT CGATCCTATAGTGAGTCTATAGTGAGTCGTAT*GGCTAG* |

TABLE 2-continued

Sequences of DNA templates

| DNA template | Sequence from 5' to 3' direction (5'biotin-Broccoli-promoter-3') |
|---|---|
| N-8 (SEQ ID NO: 21) | AAGAGCCCACACTCTACTCGACAGATACGAATATCTGGACCCGACCGTCT CGATCCTATAGTGAGTCTATAGTGAGTC*GTGGCTAGCG* |
| N-10 (SEQ ID NO: 22) | AAGAGCCCACACTCTACTCGACAGATACGAATATCTGGACCCGACCGTCT CGATCCTATAGTGAGTC*GGCTAGCGAT* |

Bold: essential T7 promoter region;
italics and bold: non-essential T7 promoter region;
italics: replacement sequence The examples and embodiments described herein are for illustrative purposes only and various modifications or changes suggested to persons skilled in the art are to be included within the spirit and purview of this application and scope of the appended claims.

What is claimed is:

1. A composition comprising a modified polypeptide, wherein the modified polypeptide comprises:
 a purified T7 RNA polymerase, a functional fragment, or a functional variant thereof; and
 a purified nucleic acid binding protein,
 wherein the purified T7 RNA polymerase and the purified nucleic acid binding protein are heterologous,
 wherein the purified T7 RNA polymerase, the functional fragment, or the functional variant thereof, and the purified nucleic acid binding protein are linked,
 wherein the purified nucleic acid binding protein is an avidin, and
 wherein the purified nucleic acid binding protein is linked to the C-terminus or N-terminus of the purified RNA polymerase, the functional fragment, or the functional variant thereof by fusion.

2. The composition of claim 1, wherein the purified T7 RNA polymerase, the functional fragment, or the functional variant thereof, and/or the purified nucleic acid binding protein are capable of being immobilized on a surface.

3. The composition of claim 2, wherein the surface comprises a solid surface selected from the group consisting of a magnetic bead, an agarose bead, fused silica, sol-gel, silica polymer, silica monolith, cellulose, agar, acrylamide, a gold bead, and a gel matrix.

4. The composition of claim 3, wherein the solid surface is a magnetic bead.

5. The composition of claim 1, wherein the purified T7 RNA polymerase, the functional fragment, or the functional variant thereof, and the purified nucleic acid binding protein are linked via a linker, wherein the linker comprises a peptide linker.

6. The composition of claim 5, wherein the purified T7 RNA polymerase, the functional fragment, or the functional variant thereof, and the purified nucleic acid binding protein are covalently linked via a linker.

7. The composition of claim 5, wherein the linker comprises at least 14 amino acid residues in length.

8. The composition of claim 5, wherein the linker comprises an amino acid sequence selected from the group consisting of SEQ ID NOs: 10-12 and SEQ ID NOs: 23-32.

9. The composition of claim 1, wherein the purified T7 RNA polymerase, the functional fragment, or the functional variant thereof, and the purified nucleic acid binding protein are linked via a second purified nucleic acid binding protein, wherein the second purified nucleic acid binding protein comprises a zinc-finger domain, a leucine zipper, a helix-tum-helix (HTH) motif, a helix-loop-helix (HLH) motif, a winged helix (WH), a winged HTH (WHTH) motif, a high mobility group (HMG)-box, a White-Opaque Regulator 3 (Wor3) domain, an oligonucleotide/oligosaccharide-binding (OB)-fold domain, an immunoglobulin fold, a B3 domain, a Transcription Activator-Like Effector (TALE), a TALE-like protein, or a Clustered Regularly Interspaced Short Palindromic Repeats (CRISPR)-associated (Cas) protein.

10. The composition of claim 1, wherein the avidin comprises streptavidin, rhizavidin, or neutravidin.

11. The composition of claim 10, wherein the avidin is a rhizavidin.

12. The composition of claim 1, wherein the purified T7 RNA polymerase, the functional fragment thereof, or the functional variant thereof comprises at least one amino acid variation relative to a wild type T7 RNA polymerase.

13. The composition of claim 1, wherein the purified T7 RNA polymerase, the functional fragment thereof, or the functional variant thereof comprises at least one amino acid variation selected from the group consisting of KI 72L, P266L, H772R, N748X, R756M, Q758X, and E775V, relative to the sequence of SEQ ID NO: 1, wherein the position is determined by alignment with the sequence of SEQ ID NO: 1, and wherein X is any amino acid different from the wild type amino acid.

14. The composition of claim 1, wherein the purified T7 RNA polymerase, the functional fragment thereof, or the functional variant thereof comprises at least two amino acid variations selected from the group consisting of KI 72L, P266L, H772R, N748X, R756M, Q758X, and E775V, relative to the sequence of SEQ ID NO: 1, wherein the position is determined by alignment with the sequence of SEQ ID NO: 1, and wherein X is any amino acid different from the wild type amino acid.

15. The composition of claim 1, wherein the purified T7 RNA polymerase, the functional fragment thereof, or the functional variant thereof comprises a sequence that has at least 90% identity to the sequence of SEQ ID NO: 1.

* * * * *

UNITED STATES PATENT AND TRADEMARK OFFICE
CERTIFICATE OF CORRECTION

PATENT NO. : 12,091,698 B2
APPLICATION NO. : 18/302247
DATED : September 17, 2024
INVENTOR(S) : Hussey et al.

It is certified that error appears in the above-identified patent and that said Letters Patent is hereby corrected as shown below:

In the Claims

Claim 13, Column 68, Line 31:
KI 72L

Should be corrected to:
K172L

Claim 14, Column 68, Line 40:
KI 72L

Should be corrected to:
K172L

Signed and Sealed this
Twenty-ninth Day of October, 2024

Katherine Kelly Vidal
*Director of the United States Patent and Trademark Office*